(12) United States Patent
Navarro Acevedo et al.

(10) Patent No.: US 7,803,989 B1
(45) Date of Patent: Sep. 28, 2010

(54) ANTIMICROBIAL PEPTIDES AND METHODS OF USE

(75) Inventors: Pedro A. Navarro Acevedo, Ankeny, IA (US); Carl R. Simmons, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 41 days.

(21) Appl. No.: 12/112,190

(22) Filed: Apr. 30, 2008

Related U.S. Application Data

(62) Division of application No. 09/950,933, filed on Sep. 11, 2001, now Pat. No. 6,875,907.

(60) Provisional application No. 60/232,569, filed on Sep. 13, 2000.

(51) Int. Cl.
| | |
|---|---|
| A01H 1/00 | (2006.01) |
| C07H 21/04 | (2006.01) |
| C12N 15/29 | (2006.01) |
| C07K 14/415 | (2006.01) |

(52) U.S. Cl. .......................... 800/295; 435/6; 435/69.1; 435/468; 435/419; 435/252.3; 435/320.1; 530/370; 536/23.6; 800/278; 800/301

(58) Field of Classification Search .................. 435/6, 435/69.1, 468, 418, 320.1; 536/23.6; 800/279, 800/301, 295; 530/370
See application file for complete search history.

(56) References Cited

U.S. PATENT DOCUMENTS 5,932,713 A 8/1999 Kasukabe et al.

FOREIGN PATENT DOCUMENTS

| WO | WO 92/21699 | 12/1992 |
|---|---|---|
| WO | WO 94/11511 | 5/1994 |

OTHER PUBLICATIONS

Herzog, Michel et al., "GASA, a gibberellin-regulated gene family from *Arabidopsis thaliana* related to the tomato GAST1 gene", Plant Molecular Biology, 1995, pp. 743-752, vol. 27, No. 4-XP002217193.
Walbot V., "Maize ESTs from various cDNA libraries sequenced at Stanford University", 2000, Database Accession No. AW288976-XP002217194.
Walbot V., "Maize ESTs from various cDNA libraries sequenced at Stanford University", 2000, Database Accession No. BE552680-XP002228602.
Segura Ana et al., "Snakin-1, a peptide from potato that is active against plant pathogens.", Molecular Plant-Microbe Interactions, 1999, pp. 16-23, vol. 12, No. 1 XP008009348.
EMBL Database Report for Accession No. CAA44807, Apr. 28, 1992.
EMBL Database Report for Accession No. 24373, dated Sep. 15, 1992.
EMBL Database Report for Accession No. 24394, dated Sep. 15, 1992.
EMBL Database Report for Accession No. 24995, dated Nov. 9, 1992.
EMBL Database Report for Accession No. AAA20129, dated Jul. 27, 1994.
EMBL Database Report for Accession No. S60229, dated Oct. 27, 1994.
EMBL Database Report for Accession No. AAA74480, dated Aug. 21, 1995.
EMBL Database Report for Accession No. AAA98520, dated Apr. 27, 1996.
EMBL Database Report for Accession No. AAB06309, dated Aug. 20, 1996.
EMBL Database Report for Accession No. AAB06308, dated Aug. 20, 1996.
EMBL Database Report for Accession No. AAB06310, dated Aug. 20, 1996.
EMBL Database Report for Accession No. CAA60677, dated Feb. 10, 1997.
EMBL Database Report for Accession No. AAB62947, dated Jul. 14, 1997.
EMBL Database Report for Accession No. 2413796, dated Sep. 19, 1997.
EMBL Database Report for Accession No. AAB97006, dated Jan. 20, 1998.
EMBL Database Report for Accession No. CAA66909, dated Mar. 30, 1998.
EMBL Database Report for Accession No. AAC15460, dated Apr. 30, 1998.
EMBL Database Report for Accession No. AAC32128, dated Aug. 17, 1998.
EMBL Database Report for Accession No. AAC32170, dated Aug. 17, 1998.
EMBL Database Report for Accession No. 3857012, dated Nov. 7, 1998.
EMBL Database Report for Accession No. JE0159, dated Sep. 13, 1998.
EMBL Database Report for Accession No. 3858022, dated Nov. 7, 1998.
EMBL Database Report for Accession No. 3857529, dated Nov. 7, 1998.
EMBL Database Report for Accession No. 3986781, dated Dec. 7, 1998.
EMBL Database Report for Accession No. AAD01518, dated Jan. 5, 1999.
EMBL Database Report for Accession No. 4225761, dated Feb. 4, 1999.
EMBL Database Report for Accession No. CAA42224, dated Feb. 15, 1999.
EMBL Database Report for Accession No. 2146734, dated Sep. 24, 1999.

(Continued)

*Primary Examiner*—Phuong T Bui

(57) ABSTRACT

The invention provides isolated KCP-like nucleic acids and their encoded proteins. The present invention provides methods and compositions relating to altering KCP-like nucleic acid and/or protein concentration and/or composition of plants. The invention further provides recombinant expression cassettes, host cells, and transgenic plants.

8 Claims, No Drawings

OTHER PUBLICATIONS

EMBL Database Report for Accession No. AAC61287, dated Apr. 5, 2000.
EMBL Database Report for Accession No. AAC20716, dated Apr. 5, 2000.
EMBL Database Report for Accession No. AAC27845, dated Apr. 5, 2000.
Ben-Nissan, et al., GIP, a Petunia hybrida GA-induced cysteine-rich protein: a possible role in shoot elongation and transition to flowering, NCBI, (2004), Accession CAD10105.
NCBI (2005) Accession NP_566186.

SEQUENCE LISTING

```
<160> NUMBER OF SEQ ID NOS: 99

<210> SEQ ID NO 1
<211> LENGTH: 730
<212> TYPE: DNA
<213> ORGANISM: Zea mays
<220> FEATURE:
<221> NAME/KEY: CDS
<222> LOCATION: (97)...(441)

<400> SEQUENCE: 1
accggacgtc cctcgctccc aaatatctct ccccacctcc cctgagcttc tcccgacctt     60
tggtcaggca aaggaggcgg ccaacaagga cgagcg atg gtg acc aag gtc atc    114
                                        Met Val Thr Lys Val Ile
                                          1               5 tgc ttc ctg gtg ctc gca tcc gtg ctc ctc gcc gtc gct ttt ccc gtg    162
Cys Phe Leu Val Leu Ala Ser Val Leu Leu Ala Val Ala Phe Pro Val
            10                  15                  20 tct gct ctg cgg cag cag gtg aag aag ggc ggc ggc ggt gaa ggc gga    210
Ser Ala Leu Arg Gln Gln Val Lys Lys Gly Gly Gly Gly Glu Gly Gly
        25                  30                  35 ggc gga ggc agt gtt agc gga agc gga ggc ggc aac ctg aat ccc tgg    258
Gly Gly Gly Ser Val Ser Gly Ser Gly Gly Gly Asn Leu Asn Pro Trp
    40                  45                  50 gag tgc tcg ccc aag tgc ggg tcg cgg tgc tcc aag acg cag tac agg    306
Glu Cys Ser Pro Lys Cys Gly Ser Arg Cys Ser Lys Thr Gln Tyr Arg
55                  60                  65                  70 aag gcc tgc ctc acc tta tgc aac aag tgc tgc gcc aag tgc ctc tgc    354
Lys Ala Cys Leu Thr Leu Cys Asn Lys Cys Cys Ala Lys Cys Leu Cys
                75                  80                  85 gtg cca ccg ggg ttc tac ggc aac aag ggc gcc tgc ccc tgc tac aac    402
Val Pro Pro Gly Phe Tyr Gly Asn Lys Gly Ala Cys Pro Cys Tyr Asn
            90                  95                 100 aac tgg aaa acc aag gaa gga ggg ccc aag tgc ccc tag aagatccacc     451
Asn Trp Lys Thr Lys Glu Gly Gly Pro Lys Cys Pro *
           105                 110 gcagctcccg tccgccattg tccccccttc tccgaatctg gaacgtgttg ttcatcttcg    511
accaccccct aaggcttggc attttattac tagtataatg ctagtgtccg cccgttgctt    571
aatctggaat gctaccagcc agatctccat gctctcctgt gagccactcg gcagagtgag    631
gattactagg tagggtggca tgtcatgtgc tccaccctcc actggtacga gtcaatcaac    691
taaagctgaa aaaaaaaaaa aaaaaaaaaa aaaaaaaa                            730

<210> SEQ ID NO 2
<211> LENGTH: 549
<212> TYPE: DNA
<213> ORGANISM: Zea mays
<220> FEATURE:
<221> NAME/KEY: CDS
<222> LOCATION: (242)...(529)

<400> SEQUENCE: 2
```

```
tacacccaga gaggccagag cgagctagtg atgactgatg actgacgagt ctctatagca      60
tacagacacc gcgcgcggcg gagccaaagc caaggacggt ccggtggtat aaataagtat     120
cacccccacc agaaccccaa gccacaccag gcacgccagc ctcactcact ccccagacca     180
cctcacacgc acgaagcagc agagcagtgg actggactag ctaggtgcct aggtgggcaa     240 c atg aag ctt cag gcc acc gcc aga gtt gct ggc ctc ctc ttc ctc gtc    289
  Met Lys Leu Gln Ala Thr Ala Arg Val Ala Gly Leu Leu Phe Leu Val
    1               5                  10                  15 ctc ctc ctg gcg ctg cct tcc ctc cgc gtc tcc atg gct gga tca ggg       337
Leu Leu Leu Ala Leu Pro Ser Leu Arg Val Ser Met Ala Gly Ser Gly
            20                  25                  30 ttc tgc gac ggc aag tgc gcg gtg agg tgc tcc aag gcg agc cgg cac       385
Phe Cys Asp Gly Lys Cys Ala Val Arg Cys Ser Lys Ala Ser Arg His
        35                  40                  45 gac gac tgc ctc aag tac tgc ggg atc tgc tgc gcc acc tgc aac tgc       433
Asp Asp Cys Leu Lys Tyr Cys Gly Ile Cys Cys Ala Thr Cys Asn Cys
    50                  55                  60 gtg ccg tcc ggg aca gcg ggc aac aag gac gag tgc cca tgc tac cgc       481
Val Pro Ser Gly Thr Ala Gly Asn Lys Asp Glu Cys Pro Cys Tyr Arg
65                  70                  75                  80 gac atg acc acc gga cac ggc aac cgc acc agg ccc aag tgc ccc tga       529
Asp Met Thr Thr Gly His Gly Asn Arg Thr Arg Pro Lys Cys Pro  *
                85                  90                  95 tgatattcat tccttcgctc                                                 549

<210> SEQ ID NO 3
<211> LENGTH: 691
<212> TYPE: DNA
<213> ORGANISM: Zea mays
<220> FEATURE:
<221> NAME/KEY: CDS
<222> LOCATION: (157)...(504)

<400> SEQUENCE: 3
aggcgcgtta atacgactca ctatagggcg aattgggtac cgggccccccc ctcgtgccca      60 agaagaggcc cccagtcccc agccagtcca cagctctcca ctcgagaaac ctccagtcca     120
gctccaccct tcgtccagag gcacaacaca cacacc atg gct ccc agc aag ctt       174
                                        Met Ala Pro Ser Lys Leu
                                          1               5 gcg gtg gtc gtc gcc ttg gta gcg tcg ctc ctc ctg ctc acc acc agc       222
Ala Val Val Val Ala Leu Val Ala Ser Leu Leu Leu Leu Thr Thr Ser
            10                  15                  20 aac acc aag ctt ggc ctg ttc gtg ctc ggc cag gct gct ccg ggc gcc       270
Asn Thr Lys Leu Gly Leu Phe Val Leu Gly Gln Ala Ala Pro Gly Ala
        25                  30                  35 tac cca cca cgg gct cct ccg ccg cac cag atc gtc gac ctc gcc aaa       318
Tyr Pro Pro Arg Ala Pro Pro Pro His Gln Ile Val Asp Leu Ala Lys
    40                  45                  50 gac tgc ggg ggc gcg tgc gac gtg cgg tgc ggc gcg cac tcg cgc aag       366
Asp Cys Gly Gly Ala Cys Asp Val Arg Cys Gly Ala His Ser Arg Lys
55                  60                  65                  70 aac atc tgc acc cgg gcg tgc ctc aag tgc tgc ggc gtc tgc cgc tgc       414
Asn Ile Cys Thr Arg Ala Cys Leu Lys Cys Cys Gly Val Cys Arg Cys
                75                  80                  85 gtg ccg gcg ggc act gcc ggc aac cag cag acg tgc ggc aag tgc tac       462
Val Pro Ala Gly Thr Ala Gly Asn Gln Gln Thr Cys Gly Lys Cys Tyr
            90                  95                 100 acc gac tgg acc acg cac ggc aac aag acc aag tgc ccg tga               504
Thr Asp Trp Thr Thr His Gly Asn Lys Thr Lys Cys Pro  *
```

-continued

```
                     105                 110                 115
ctccttgtcc ttgacgagag cagcatgagt ccatgggccc actggcgcca cgttttgtat        564
gatccgaccc cgtcggcgta gatgtccgag cctgtagcta tctagcttag atgtacgagg        624
ttgatgtgct ctgctgtttg ttttttgcta gtacttctag tgtgtatctt tgtgttgaaa        684
aaaaaaa                                                                   691

<210> SEQ ID NO 4
<211> LENGTH: 831
<212> TYPE: DNA
<213> ORGANISM: Zea mays
<220> FEATURE:
<221> NAME/KEY: CDS
<222> LOCATION: (144)...(446)

<400> SEQUENCE: 4
ggtcgaccag gttcacgccg acgtccaggt gctcgtcgcg gcgcgcactg accttgtcaa         60
ccggctccag ggcctacggg agaagctcgc ctcactaagc caaagctgac agcagcatac        120
aagcaccagc agagctcttg ccg atg gcg gtg gcc aag ccc ccg ctt cag acg       173
                          Met Ala Val Ala Lys Pro Pro Leu Gln Thr
                           1               5                  10 gcc gcg gtc ctc ctc ctc ctc ctc ctg gtc gtc gcg gcc gcg tcg tgg         221
Ala Ala Val Leu Leu Leu Leu Leu Leu Val Val Ala Ala Ala Ser Trp
                15                  20                  25 ctc cag acc gtc gac gcc gct tca ggg ttc tgc tcg agc aag tgc agc         269
Leu Gln Thr Val Asp Ala Ala Ser Gly Phe Cys Ser Ser Lys Cys Ser
        30                  35                  40 gtc cgg tgc ggg cgg gcg gcg agc gcg cgg gcg cgg ggc gcg tgc atg         317
Val Arg Cys Gly Arg Ala Ala Ser Ala Arg Ala Arg Gly Ala Cys Met
    45                  50                  55 agg tcc tgc ggc ctc tgc tgc gag gag tgc aac tgc gtg ccc acg cgg         365
Arg Ser Cys Gly Leu Cys Cys Glu Glu Cys Asn Cys Val Pro Thr Arg
60                  65                  70 ccg ccg cgc gac gtc aac gag tgc ccc tgc tac cgc gac atg ctc acc         413
Pro Pro Arg Asp Val Asn Glu Cys Pro Cys Tyr Arg Asp Met Leu Thr
    75                  80                  85                  90 gcc ggc ccc agg aag agg ccc aag tgc ccc tga ggccggctca cacacggcgc       466
Ala Gly Pro Arg Lys Arg Pro Lys Cys Pro  *
            95                  100 aacccaagac acgtgctcca tgggactgcc actgctttgc ctgcaactgc gattcgatcc        526
atgctgatgg gccaaggcac cctgttatgc tatccctaac cttactacta cgtatttgtg        586
tacgtacgta tctttgtatg catcgcgcgc ccgtgtgatc tataatatat aatctgctac        646
caggtcccgt cagatgtact gttagtgata agctgagcga ctagagaggt actgaatcct        706
cagtagttgg tagaacgggc tgttcctcgg gacagtgtgt gtcatggtta ggctgcctgt        766
actaattaat gtacatgaac tattgtgcta tatatatata ttgtcataaa aaaaaaaaa         826 aaaaa                                                                    831

<210> SEQ ID NO 5
<211> LENGTH: 621
<212> TYPE: DNA
<213> ORGANISM: Zea mays
<220> FEATURE:
<221> NAME/KEY: CDS
<222> LOCATION: (137)...(523)

<400> SEQUENCE: 5
attacgccaa gctctaatac gactcactat agggaaagct ggtacgcctg caggtaccgg         60
```

```
tccggaattc ccgggtcgac ccacgcgtcc gcttcactca cgaaggcacc ctcccttgcc    120 actcctttc cttgag atg atg acg acg atg aag aag aag aag cag cag cag    172
              Met Met Thr Thr Met Lys Lys Lys Lys Gln Gln Gln
               1               5                  10 cag ctc ctc ctc ctt tct ctc atg ttt ctt gtt gct gtg aca gca gcc    220
Gln Leu Leu Leu Leu Ser Leu Met Phe Leu Val Ala Val Thr Ala Ala
        15                  20                  25 gct gtt gct gcc gat cca cat cca cag cag gtg cag gtg cag cag cag    268
Ala Val Ala Ala Asp Pro His Pro Gln Gln Val Gln Val Gln Gln Gln
    30                  35                  40 cag caa gca cag atg agg att aac agg gcc acc aga tcc ctt ctt cct    316
Gln Gln Ala Gln Met Arg Ile Asn Arg Ala Thr Arg Ser Leu Leu Pro
45                  50                  55                  60 cag ccg ccg ccg aaa cta gac tgc ccg tcc acc tgc tcc gtg cgc tgc    364
Gln Pro Pro Pro Lys Leu Asp Cys Pro Ser Thr Cys Ser Val Arg Cys
                65                  70                  75 ggc aac aac tgg aag aac cag atg tgc aac aag atg tgc aac gtc tgc    412
Gly Asn Asn Trp Lys Asn Gln Met Cys Asn Lys Met Cys Asn Val Cys
                80                  85                  90 tgc aac aag tgc agc tgc gtg ccg ccg ggg acc ggc cag gac acc cgc    460
Cys Asn Lys Cys Ser Cys Val Pro Pro Gly Thr Gly Gln Asp Thr Arg
            95                  100                 105 cac ctc tgc ccc tgc tac gac acc atg ctc aat cca cac acc ggc aag    508
His Leu Cys Pro Cys Tyr Asp Thr Met Leu Asn Pro His Thr Gly Lys
        110                 115                 120 ctt aag tgc ccc tag gccgtcgcca tcatgttat gtacaatgta ctatcatcac    563
Leu Lys Cys Pro *
125 ttcaataata ataaaaacaa cttctggttc caaaaaaaaa aaaaaaaaaa aaaaaaaa    621

<210> SEQ ID NO 6
<211> LENGTH: 648
<212> TYPE: DNA
<213> ORGANISM: Zea mays
<220> FEATURE:
<221> NAME/KEY: CDS
<222> LOCATION: (142)...(432)

<400> SEQUENCE: 6
ctcacaccga agcgcctca actctgaagg cgctacagca acgtcgccac ttcactcacg    60
attggagttt cacctcggca gcccagccag ccagtggttc ctcggctcgg aggaacaggc    120
gaacagcaag agcttctgaa g atg aag gcg atc ccc gtg gct ctc ctg ctc    171
                       Met Lys Ala Ile Pro Val Ala Leu Leu Leu
                        1               5                  10 ctc gtc ctg gtt gct gcc gcc tcc tcg ttc aag cat ctc gcc gag gca    219
Leu Val Leu Val Ala Ala Ala Ser Ser Phe Lys His Leu Ala Glu Ala
                15                  20                  25 gca gac ggc ggc gcg gtg ccg gac ggc gtg tgc gac ggc aag tgc cgc    267
Ala Asp Gly Gly Ala Val Pro Asp Gly Val Cys Asp Gly Lys Cys Arg
    30                  35                  40 agc cgg tgc tcg ctg aag aag gcc ggg cgg tgc atg ggc ctg tgc atg    315
Ser Arg Cys Ser Leu Lys Lys Ala Gly Arg Cys Met Gly Leu Cys Met
            45                  50                  55 atg tgc tgc ggc aag tgc cag ggc tgc gtg ccg tcg ggg ccg tac gcc    363
Met Cys Cys Gly Lys Cys Gln Gly Cys Val Pro Ser Gly Pro Tyr Ala
        60                  65                  70 agc aag gac gag tgc ccc tgc tac agg gac atg aag tcc ccc aag aac    411
Ser Lys Asp Glu Cys Pro Cys Tyr Arg Asp Met Lys Ser Pro Lys Asn
75                  80                  85                  90
```

```
cag cgc ccc aag tgc ccc tag gccctaccgc tctaagggag ggaggatgac      462
Gln Arg Pro Lys Cys Pro *
              95 ccaggatttc gctcgcgatc ctgcacagct tctagtcttg tactgctagt ttagcgcgcc  522 gagcgtcgga atgtcgcgac ggttccttcc gtgcttgtgt gctgtgtttc tcctcggacg  582 tgctttaacc tagaataata accaatgcac tgtatctgtg tgcttgtcaa aaaaaaaaa   642 aaaaaa                                                            648

<210> SEQ ID NO 7
<211> LENGTH: 806
<212> TYPE: DNA
<213> ORGANISM: Zea mays
<220> FEATURE:
<221> NAME/KEY: CDS
<222> LOCATION: (136)...(525)

<400> SEQUENCE: 7
ctccgacctc tctccattat tccatcccgg cggcggcggc ggcgcgcggc gtgcgtgtca   60
cactcactga tcagtatccc cgcgggccgt actccttccc ttgtccgttc cgctgcgcag  120
cagacggcgc acggc atg gcc agc agg aac aag gcg gcg gcg ctg ctc ctc  171
              Met Ala Ser Arg Asn Lys Ala Ala Ala Leu Leu Leu
               1               5                  10 tgc ttc ctg ttc ctg gcc gcg gtc gcc gcc tcc gcc gcc gag atg atc   219
Cys Phe Leu Phe Leu Ala Ala Val Ala Ala Ser Ala Ala Glu Met Ile
            15                  20                  25 gcc ggc agt ggg atc ggc gac ggc gaa ggt gaa gag ctg gac aag ggc   267
Ala Gly Ser Gly Ile Gly Asp Gly Glu Gly Glu Glu Leu Asp Lys Gly
        30                  35                  40 ggc ggc ggc ggc ggc ggc cac cac aag cac gag ggc tac aag aac aag   315
Gly Gly Gly Gly Gly Gly His His Lys His Glu Gly Tyr Lys Asn Lys
    45                  50                  55                  60 gat ggc aag gga aac ctg aag ccc tct cag tgc ggg ggg gag tgc cgg   363
Asp Gly Lys Gly Asn Leu Lys Pro Ser Gln Cys Gly Gly Glu Cys Arg
                65                  70                  75 cgg cgg tgc tcc aag acg cac cac aag aag ccg tgc ctc ttc ttc tgc   411
Arg Arg Cys Ser Lys Thr His His Lys Lys Pro Cys Leu Phe Phe Cys
            80                  85                  90 aac aag tgc tgc gcc aag tgc ctg tgc gtg ccg cct ggc acc tac ggc   459
Asn Lys Cys Cys Ala Lys Cys Leu Cys Val Pro Pro Gly Thr Tyr Gly
        95                  100                 105 aac aag gag acc tgc ccc tgc tac aac aac tgg aag acc aag aaa gga   507
Asn Lys Glu Thr Cys Pro Cys Tyr Asn Asn Trp Lys Thr Lys Lys Gly
    110                 115                 120 ggg ccc aag tgc ccg tga gtcgtgagaa gatggcggcc caatacgcgg          555
Gly Pro Lys Cys Pro *
125 ttttccggc ggctacgcgg gcgggccgcc ggcccatcgt aacctaccac cgtagttgga   615
agcgtcgtag gataggttag gaataaataa tagcctctct ttttttttt gccttgtttc   675 ggtgtttgtt tgggcgggc cggctgccgc ttctctggtc tctggtctaa aaagttcccg  735 aaaatatta tatatttaat aagaagaaga aggagggaa aaaaaaaaa aaaaaaaaa    795 aaaaaaaaa a                                                      806

<210> SEQ ID NO 8
<211> LENGTH: 720
<212> TYPE: DNA
<213> ORGANISM: Zea mays
```

<220> FEATURE:
<221> NAME/KEY: CDS
<222> LOCATION: (119)...(403)

<400> SEQUENCE: 8

```
ctcgcctctc tctcgcgcaa gccacagtag agcaaccaac cataccaccg gcccgtgtcg      60
atctctggcc tctctcgtgc aaggaattaa gcaggcaaga ggccaacctt cttccagc      118 atg gcc aag gcg agc agc agg ctg ctc ttc tcg ctc tcg ctc gtc gtc      166
Met Ala Lys Ala Ser Ser Arg Leu Leu Phe Ser Leu Ser Leu Val Val
 1               5                  10                  15 ctg ctg ctc ctc gtg gag acc act act tct ccc cat gga cag gct gac      214
Leu Leu Leu Leu Val Glu Thr Thr Thr Ser Pro His Gly Gln Ala Asp
             20                  25                  30 gcc atc gac tgc ggc gcg agc tgc tcg tac cgg tgc agc aag tcg gga      262
Ala Ile Asp Cys Gly Ala Ser Cys Ser Tyr Arg Cys Ser Lys Ser Gly
         35                  40                  45 cgg ccc aag atg tgc ctg agg gcg tgc ggc acc tgc tgc cag cgc tgc      310
Arg Pro Lys Met Cys Leu Arg Ala Cys Gly Thr Cys Cys Gln Arg Cys
     50                  55                  60 ggc tgc gtc ccg ccg ggc acc tcc ggc aac gag gac gtc tgc ccc tgc      358
Gly Cys Val Pro Pro Gly Thr Ser Gly Asn Glu Asp Val Cys Pro Cys
 65                  70                  75                  80 tac gcc aac atg aag acc cac gac ggc cag cac aag tgc ccg tga          403
Tyr Ala Asn Met Lys Thr His Asp Gly Gln His Lys Cys Pro *
                 85                  90 tccatccacc gtggttccca gcatcagcag ctttgccaaa aagacatgat acctacatat    463
atataagagt acctagctgc tgctgctcta ctaccttgtt ggttcattat attgtgcgcg    523
tgcatgcatg aataaataaa tgaacatatt agggcatgta caacccagat acggctgcac    583
ggtactccaa gtacaagata caactaaaac acaacacaat acagtggtca tgtctaaaac    643
atgtgtctta cgatattcat tgtaccaatc agagtattca ataaattaaa gtgaccaaaa    703
aaaaaaaaaa aaaaaaa                                                    720
```

<210> SEQ ID NO 9
<211> LENGTH: 754
<212> TYPE: DNA
<213> ORGANISM: Zea mays
<220> FEATURE:
<221> NAME/KEY: CDS
<222> LOCATION: (102)...(539)

<400> SEQUENCE: 9

```
gaattgtaat acgactcact atagggcgaa ttgggtaccg ggccccccct cgaggagtcg      60
aggttcaggt tccacggtgc ggcgagagct agctcgcagc c atg gag agc aag agc    116
                                              Met Glu Ser Lys Ser
                                               1               5 cca tgg tcg ctg cgg ctg cta att tgc tgc gcg gca atg gtg gcc atc      164
Pro Trp Ser Leu Arg Leu Leu Ile Cys Cys Ala Ala Met Val Ala Ile
             10                  15                  20 gcg ctt ctc ccc caa caa gga ggc cag gcc gct tgt ttc gtg ccg acg      212
Ala Leu Leu Pro Gln Gln Gly Gly Gln Ala Ala Cys Phe Val Pro Thr
         25                  30                  35 ccg ggt cca gct ccg gca ccg ccc ggc tcc tcc gcg acg aac acg aac      260
Pro Gly Pro Ala Pro Ala Pro Pro Gly Ser Ser Ala Thr Asn Thr Asn
     40                  45                  50 gcc tcc tcc gct gct cct cgg cca gcc aag ccc agc gca ttc ccg ccc      308
Ala Ser Ser Ala Ala Pro Arg Pro Ala Lys Pro Ser Ala Phe Pro Pro
 55                  60                  65
```

```
cca atg tac ggt ggt gtc acc ccc ggc acc ggc agc ctc cag ccc cac    356
Pro Met Tyr Gly Gly Val Thr Pro Gly Thr Gly Ser Leu Gln Pro His
 70              75                  80                  85 gag tgc ggc ggc cgg tgc gcg gag cgg tgc tcg gcg acg gcg tac cag    404
Glu Cys Gly Gly Arg Cys Ala Glu Arg Cys Ser Ala Thr Ala Tyr Gln
                 90                  95                 100 aag ccg tgc ctc ttc ttc tgc cgc aag tgc tgc gcg gcg tgc ctg tgc    452
Lys Pro Cys Leu Phe Phe Cys Arg Lys Cys Cys Ala Ala Cys Leu Cys
            105                 110                 115 gtg ccg ccg ggc acc tac ggc aac aag aac acc tgc ccc tgc tac aac    500
Val Pro Pro Gly Thr Tyr Gly Asn Lys Asn Thr Cys Pro Cys Tyr Asn
120                 125                 130 aac tgg aag acc aag cgg gga ggc ccc aag tgc ccc tag tagccctccc     549
Asn Trp Lys Thr Lys Arg Gly Gly Pro Lys Cys Pro  *
    135                 140                 145 tctcggtcta cttgatgaga tcttctgttc aaaaaatcaa aaggaataag aatctgttta  609
actatcttta gatttcacct cgtgccgaat tcctgcagcc cggggatcc acttagtttc   669 ttagagcggc ccgcccaccg cggttggagt tcccagcttt tgtttccctt tagtgagggt  729
taatttcgag cttggcgtaa tcctg                                        754

<210> SEQ ID NO 10
<211> LENGTH: 594
<212> TYPE: DNA
<213> ORGANISM: Triticum aestivum
<220> FEATURE:
<221> NAME/KEY: CDS
<222> LOCATION: (111)...(344)

<400> SEQUENCE: 10
gctcttaccc agccacacgc ggagaagaga cgcagcaagc gccatggcca agatctcctt   60
cctcctcgtg gcgctcctcg tcctcgccgt gccgtgccgt gcaggaggtg atg gga    116
                                                         Met Gly
                                                           1 ggc ggc aac ggc ggc gcc ggc ggc ggc ggc aag ctc aag cca tgg gag    164
Gly Gly Asn Gly Gly Ala Gly Gly Gly Gly Lys Leu Lys Pro Trp Glu
      5                  10                  15 tgc tcg tcc aag tgc tcg tcg cgg tgc tcg ggg acg cag tac aag aag    212
Cys Ser Ser Lys Cys Ser Ser Arg Cys Ser Gly Thr Gln Tyr Lys Lys
 20                  25                  30 gcg tgc ctg acc tac tgc aac aag tgc tgc gcc act tgc ctc tgc gtg    260
Ala Cys Leu Thr Tyr Cys Asn Lys Cys Cys Ala Thr Cys Leu Cys Val
 35                  40                  45                  50 ccg ccg ggc acc tac ggc aac aag ggc gcc tgc ccc tgc tac aac aac    308
Pro Pro Gly Thr Tyr Gly Asn Lys Gly Ala Cys Pro Cys Tyr Asn Asn
             55                  60                  65 tgg aag acc aag gag gga ggc ccc aag tgc ccc tag attcttgatt         354
Trp Lys Thr Lys Glu Gly Gly Pro Lys Cys Pro  *
         70                  75 ttctttcttc ttcttctggg gtgccagctt gcggttgatg gttattcact gctcggccat  414
caaaatgtac tacagtagat ctgaattatg tgatgggcat ttaatcagtg gcatgtgaat  474
tgccctccca gttacctgta tttctatcag taagatgtgg aaaactggag gcactccgcc  534
actcccacat gattatagtg ggccctaaaa aaaaaaaaa aaaaaaaaa aaaaaaaaa     594

<210> SEQ ID NO 11
<211> LENGTH: 677
<212> TYPE: DNA
<213> ORGANISM: Triticum aestivum
<220> FEATURE:
```

-continued

```
<221> NAME/KEY: CDS
<222> LOCATION: (80)...(364)

<400> SEQUENCE: 11
ctccagcctc ctcctatcgt caagctcaca ccaaccagca ggagggctct gccagagcga      60
agcaaccaag aacaccacg atg aag aag ctt cgc acc acc act ctg gct ctc     112
                     Met Lys Lys Leu Arg Thr Thr Thr Leu Ala Leu
                      1               5                   10 ctt ctc ctc ctc gtc ttc cta gca gcc tcg tcc ctc cgt gcc gcc atg      160
Leu Leu Leu Leu Val Phe Leu Ala Ala Ser Ser Leu Arg Ala Ala Met
            15                  20                  25 gct ggg tca gcg ttc tgc gac ggc aag tgc ggg gtg agg tgc tcc aag      208
Ala Gly Ser Ala Phe Cys Asp Gly Lys Cys Gly Val Arg Cys Ser Lys
    30                  35                  40 gcg agc cgg cac gac gac tgc ctc aag tac tgc ggg ata tgc tgc gcc      256
Ala Ser Arg His Asp Asp Cys Leu Lys Tyr Cys Gly Ile Cys Cys Ala
45                  50                  55 gag tgc aac tgc gtg ccg tcg ggg acc gcc ggc aac aag gac gag tgc      304
Glu Cys Asn Cys Val Pro Ser Gly Thr Ala Gly Asn Lys Asp Glu Cys
60                  65                  70                  75 ccc tgc tac cgc gac aag acc acc ggc cac ggc gcg cgc aag agg ccc      352
Pro Cys Tyr Arg Asp Lys Thr Thr Gly His Gly Ala Arg Lys Arg Pro
                80                  85                  90 aag tgc cca tga tccgccacca ctctccaggc atcgatcctc caccgcccat         404
Lys Cys Pro * ggcgtctaca caccatatgc ctgagcttca tgcatcccta tctatcatgt cgtaccatgt    464
cgcggatcac tactagtata tcttataagc gtgtaaacca tgatctgtag cgtctggtgc    524
atgatccgat tccgactata tgttgatgtg cataatgctg gcctagctac tggtatgccg    584
gccggtaaaa atgtcgctgt gctgtaataa tgaaccatga cgcatcagta aagtttgtcc    644
agtaatttcc ttgttaaaaa aaaaaaaaaa aaa                                 677

<210> SEQ ID NO 12
<211> LENGTH: 639
<212> TYPE: DNA
<213> ORGANISM: Triticum aestivum
<220> FEATURE:
<221> NAME/KEY: CDS
<222> LOCATION: (81)...(377)

<400> SEQUENCE: 12
tcaagctcac acggtcacac caaccagcag ggctctgcca ctgccagagc caagcaactc      60
aagaacagta gaacaccacg atg aag aag ctt cgc acc acc acc gcc acc acc    113
                     Met Lys Lys Leu Arg Thr Thr Thr Ala Thr Thr
                      1               5                   10 act ctg gct ctc att ctc ctc ctc gtc ctc ata gca gcc acg tcc ctc      161
Thr Leu Ala Leu Ile Leu Leu Leu Val Leu Ile Ala Ala Thr Ser Leu
            15                  20                  25 cgt gtc gcc atg gct gga tca gcg ttc tgc gac agc aag tgc ggg gtg      209
Arg Val Ala Met Ala Gly Ser Ala Phe Cys Asp Ser Lys Cys Gly Val
    30                  35                  40 agg tgc tcc aag gcg ggc cgg cac gac gac tgc ctc aag tac tgc ggg      257
Arg Cys Ser Lys Ala Gly Arg His Asp Asp Cys Leu Lys Tyr Cys Gly
45                  50                  55 ata tgc tgc gcc gag tgc aac tgc gtg ccg tcg ggg aca gcc ggc aac      305
Ile Cys Cys Ala Glu Cys Asn Cys Val Pro Ser Gly Thr Ala Gly Asn
60                  65                  70                  75 aag gac gag tgc ccc tgc tac cgc gac aaa acc acc ggc cac ggc gcg      353
Lys Asp Glu Cys Pro Cys Tyr Arg Asp Lys Thr Thr Gly His Gly Ala
```

|  |  | 80 |  |  | 85 |  |  | 90 |  |  |
|---|---|---|---|---|---|---|---|---|---|---|

```
cgc acg agg ccc aag tgc cca tga tccgccaccg cccatggcgc ctgcatagca      407
Arg Thr Arg Pro Lys Cys Pro *
                95 tgtacctgaa cttcatgcat ctttatcatg tcgtactatg tcgcgggtca ctactattat      467 attatactat atgtgtgtaa atcatgatct gaagcgtccg gtgcatgatc cgactgtatg      527 ttgataatgc gtaatgctgg cctactggta tgccggtaaa aatgtcgttg ttctgtaata      587 ataaactaca tgcattatta gagtcaaaaa aaaaaaaaaa aaaaaaaaaa aa             639

<210> SEQ ID NO 13
<211> LENGTH: 506
<212> TYPE: DNA
<213> ORGANISM: Triticum aestivum
<220> FEATURE:
<221> NAME/KEY: CDS
<222> LOCATION: (2)...(325)

<400> SEQUENCE: 13 g atg aag cct ctc ccg gtg acc ctg gct ctc ctg gcc ctc ttc ctc gtc      49
  Met Lys Pro Leu Pro Val Thr Leu Ala Leu Leu Ala Leu Phe Leu Val
   1               5                  10                  15 gcc tcg tac cag gac ctc acc gtg gcc gca gat gca gat gca gat gca      97
Ala Ser Tyr Gln Asp Leu Thr Val Ala Ala Asp Ala Asp Ala Asp Ala
           20                  25                  30 gct gga gct gga gat gtt ggc gcc gtt ccg gtt ccg gac agc gtg tgc      145
Ala Gly Ala Gly Asp Val Gly Ala Val Pro Val Pro Asp Ser Val Cys
       35                  40                  45 gag ggc aag tgc aag aac cgg tgc tcg cag aag gtg gcc ggg cgg tgc      193
Glu Gly Lys Cys Lys Asn Arg Cys Ser Gln Lys Val Ala Gly Arg Cys
   50                  55                  60 atg ggg ctg tgc atg atg tgc tgc ggc aag tgc gcc ggc tgc gtg ccg      241
Met Gly Leu Cys Met Met Cys Cys Gly Lys Cys Ala Gly Cys Val Pro
 65                  70                  75                  80 tcg ggg ccg ttg gcc ccc aag gac gag tgc ccc tgc tac cgc gac atg      289
Ser Gly Pro Leu Ala Pro Lys Asp Glu Cys Pro Cys Tyr Arg Asp Met
                 85                  90                  95 aaa tcc ccc aag agc ggc cgc ccc aaa tgc ccc tag gactagggcg           335
Lys Ser Pro Lys Ser Gly Arg Pro Lys Cys Pro *
               100                 105 cttcttttc tttcttgggt ggaatgggat cttgacgagc cgggtgcgtg ggatttaggg      395
gttccccttg tttgtaagct tgatttgttc gggataaaca acgcagatcc cggtttgagg     455 ggggcccgg tacccaattc gccctatagt gagtcgtatt acgcgcgctc c              506

<210> SEQ ID NO 14
<211> LENGTH: 506
<212> TYPE: DNA
<213> ORGANISM: Triticum aestivum
<220> FEATURE:
<221> NAME/KEY: CDS
<222> LOCATION: (79)...(372)
<221> NAME/KEY: misc_feature
<222> LOCATION: 55
<223> OTHER INFORMATION: n = a, t, c, or g
<221> NAME/KEY: misc_feature
<222> LOCATION: 270
<223> OTHER INFORMATION: n = a, t, c, or g
<221> NAME/KEY: misc_feature
<222> LOCATION: 303
<223> OTHER INFORMATION: n = a, t, c, or g
<221> NAME/KEY: misc_feature
<222> LOCATION: 425
<223> OTHER INFORMATION: n = a, t, c, or g
```

```
<221> NAME/KEY: misc_feature
<222> LOCATION: 432
<223> OTHER INFORMATION: n = a, t, c, or g
<221> NAME/KEY: misc_feature
<222> LOCATION: (442)...(442)
<223> OTHER INFORMATION: n = a, t, c, or g
<221> NAME/KEY: misc_feature
<222> LOCATION: (457)...(457)
<223> OTHER INFORMATION: n = a, t, c, or g
<221> NAME/KEY: misc_feature
<222> LOCATION: (465)...(465)
<223> OTHER INFORMATION: n = a, t, c, or g
<221> NAME/KEY: misc_feature
<222> LOCATION: (502)...(502)
<223> OTHER INFORMATION: n = a, t, c, or g

<400> SEQUENCE: 14
ccactctgcg accaccttat ctagctcctt ctgcaagctc ctgcatccat ctcanctgca      60
gctcgaagct cgaccagg atg agc aag cca tcg agg tgc agg gca gtg cag      111
                    Met Ser Lys Pro Ser Arg Cys Arg Ala Val Gln
                     1               5                  10 acg cag gtc gcc ctg ctc ctc ctc ttg ctc gtc gct gcc tcc ctg ctc      159
Thr Gln Val Ala Leu Leu Leu Leu Leu Leu Val Ala Ala Ser Leu Leu
             15                  20                  25 cag gcc ggc gac gct gct tca ggg ttc tgc gcg ggc aag tgc gcg gtc      207
Gln Ala Gly Asp Ala Ala Ser Gly Phe Cys Ala Gly Lys Cys Ala Val
         30                  35                  40 cgg tgc ggg cgg tcg cgc gca aag cgg ggg gcg tgc atg aag tac tgc      255
Arg Cys Gly Arg Ser Arg Ala Lys Arg Gly Ala Cys Met Lys Tyr Cys
     45                  50                  55 ggg ctg tgt tgc gan gag tgc gcc tgc gtg ccg acg ggg agg agc ggn      303
Gly Leu Cys Cys Xaa Glu Cys Ala Cys Val Pro Thr Gly Arg Ser Xaa
 60                  65                  70                  75 agc cgc gac gag tgc ccc tgc tac cgc gac atg ctc acc gcc ggg ccc      351
Ser Arg Asp Glu Cys Pro Cys Tyr Arg Asp Met Leu Thr Ala Gly Pro
                 80                  85                  90 agg aag agg cca aag tgc ccg tgatctcgtc ggtcgaacgt ctgaacggac         402
Arg Lys Arg Pro Lys Cys Pro
                 95 aaccggctta accccaacc tancgagtan cgacaaagan ttatggctgt ttganattgg      462 acnccccgtct taagtaactt cctgtgccgt ttcccgtgcn aaat                     506

<210> SEQ ID NO 15
<211> LENGTH: 769
<212> TYPE: DNA
<213> ORGANISM: Triticum aestivum
<220> FEATURE:
<221> NAME/KEY: CDS
<222> LOCATION: (56)...(400)

<400> SEQUENCE: 15
ctgagcttct cccgaccttt ggtcaggcaa aggaggcggc caacaaggac gagcg atg      58
                                                                Met
                                                                 1 gtg acc aag gtc atc tgc ttc ctg gtg ctc gca tcc gtg ctc ctc gcc      106
Val Thr Lys Val Ile Cys Phe Leu Val Leu Ala Ser Val Leu Leu Ala
             5                  10                  15 gtc gct ttt ccc gtg tct gct ctg cgg cag cag gtg aag aag ggc ggc      154
Val Ala Phe Pro Val Ser Ala Leu Arg Gln Gln Val Lys Lys Gly Gly
         20                  25                  30 ggc ggt gaa ggc gga ggc gga ggc agt gtt agc gga agc gga ggc ggc      202
Gly Gly Glu Gly Gly Gly Gly Gly Ser Val Ser Gly Ser Gly Gly Gly
     35                  40                  45
```

```
aac ctg aat ccc tgg gag tgc tcg ccc aag tgc ggg tcg cgg tgc tcc    250
Asn Leu Asn Pro Trp Glu Cys Ser Pro Lys Cys Gly Ser Arg Cys Ser
 50              55                  60                  65 aag acg cag tac agg aag gcc tgc ctc acc tta tgc aac aag tgc tgc    298
Lys Thr Gln Tyr Arg Lys Ala Cys Leu Thr Leu Cys Asn Lys Cys Cys
         70                  75                  80 gcc aag tgc ctc tgc gtg cca ccg ggg ttc tac ggc aac aag ggc gcc    346
Ala Lys Cys Leu Cys Val Pro Pro Gly Phe Tyr Gly Asn Lys Gly Ala
     85                  90                  95 tgc ccc tgc tac aac aac tgg aaa acc cgg gaa gga ggg ccc aag tgc    394
Cys Pro Cys Tyr Asn Asn Trp Lys Thr Arg Glu Gly Gly Pro Lys Cys
        100                 105                 110 ccc tag aagatccacc gcagctcccg tccgccattg tccccccttc tccgaatctg     450
Pro * gaacgtgttg ttcatcttcg accaccccct aggcttggca tttattact agtataatgc   510 tagtgtccgc ccgttgctta atctggaatg ctaccagcca gatctccatg ctctcctgtg  570
agccactcgg cagagtgagg attactaggt agggtggcat gtcatgtgct ccaccctcca  630
ctggtacgag tcaatcaact aaagctaccc ccggattgat gaggaacatc ccgcgcgatt  690
agtggggcat gtcattacat tcatcagctt ctatatataa actagataaa cttttttatca 750 aaaaaaaaaa aaaaaaaaa                                                769

<210> SEQ ID NO 16
<211> LENGTH: 692
<212> TYPE: DNA
<213> ORGANISM: Triticum aestivum
<220> FEATURE:
<221> NAME/KEY: CDS
<222> LOCATION: (137)...(448)

<400> SEQUENCE: 16
tcgcaaacca agcccctgcc acttgcaacg cacacttaca ccgcttgcag agctccagct   60
cgacctctag ctagcatcca tggcgcagcc tctcactcgc cgccgtctcc tccttcctcc  120
gcctctgctt ctgctg atg ctc ctc ctc gct ctc gcc gcc cac cat cag gcc  172
               Met Leu Leu Leu Ala Leu Ala Ala His His Gln Ala
                1               5                   10 gct tcc gac cca ccg gcg acc cac ggc ggc atg cga gcc agc ggc acc    220
Ala Ser Asp Pro Pro Ala Thr His Gly Gly Met Arg Ala Ser Gly Thr
         15                  20                  25 agg tcc ctg ctc cag cag cag ccg cct cct ccc agg cta gac tgc ccc    268
Arg Ser Leu Leu Gln Gln Gln Pro Pro Pro Pro Arg Leu Asp Cys Pro
 30                  35                  40 aag gtg tgc gcg ggc cgg tgc gcc aac aac tgg agg aag gag atg tgc    316
Lys Val Cys Ala Gly Arg Cys Ala Asn Asn Trp Arg Lys Glu Met Cys
 45                  50                  55                  60 aac gac aag tgc aac gtc tgc tgc cag cgc tgc aac tgc gtg ccc ccc    364
Asn Asp Lys Cys Asn Val Cys Cys Gln Arg Cys Asn Cys Val Pro Pro
             65                  70                  75 ggc acc ggc cag gac acc cgc cac atc tgc ccc tgc tac gcc acc atg    412
Gly Thr Gly Gln Asp Thr Arg His Ile Cys Pro Cys Tyr Ala Thr Met
         80                  85                  90 acc aac ccg cac aac ggc aag ctc aag tgc ccc tag gcatcacatc         458
Thr Asn Pro His Asn Gly Lys Leu Lys Cys Pro *
     95                 100 atcttcagag gcatatgctc cgcctcatgc gtctccctg ccatgttcta ctagctagct   518
ctagtactct agcatgtact atttgatgtg atcttcagct acattccata agctcacagt  578
gtcacactca cacatgtagt gttgagttgc attgcagcct cctcattctc actcaaccat  638
```

```
gatgatgatg atttcctgat aattaatttc ctgcatactt gttgatcaaa aaaa          692

<210> SEQ ID NO 17
<211> LENGTH: 685
<212> TYPE: DNA
<213> ORGANISM: Oryza sativa
<220> FEATURE:
<221> NAME/KEY: CDS
<222> LOCATION: (88)...(405)

<400> SEQUENCE: 17
atcaatcact caaggcccct cctcctctct ccatcaagag aagctctacc tcggcccgtc    60
ctcgcccgcc ggccggccgc cgtcgcc atg gct ccc ggc aag ctc gcg gtg ttc   114
                                Met Ala Pro Gly Lys Leu Ala Val Phe
                                  1               5 gcc ctc ctg gcg tct ctc ctc ctc ctc aac acc atc aag gcc gca gac    162
Ala Leu Leu Ala Ser Leu Leu Leu Leu Asn Thr Ile Lys Ala Ala Asp
 10              15                  20                  25 tac cct ccg gct cct ccc ctt ggg ccg cct ccc cac aag atc gta gac    210
Tyr Pro Pro Ala Pro Pro Leu Gly Pro Pro Pro His Lys Ile Val Asp
                 30                  35                  40 ccc ggc aaa gac tgc gtg ggg gcg tgc gac gcg cgg tgc agc gag cac    258
Pro Gly Lys Asp Cys Val Gly Ala Cys Asp Ala Arg Cys Ser Glu His
             45                  50                  55 tcg cac aag aag cgg tgc agc cgc tcc tgc ctc acg tgc tgc agc gcg    306
Ser His Lys Lys Arg Cys Ser Arg Ser Cys Leu Thr Cys Cys Ser Ala
         60                  65                  70 tgc cgc tgc gtc ccg gcg ggc acg gcc ggc aac cgg gag acc tgc ggc    354
Cys Arg Cys Val Pro Ala Gly Thr Ala Gly Asn Arg Glu Thr Cys Gly
     75                  80                  85 agg tgc tac acc gac tgg gtc tcg cac aac aac atg acc aag tgc ccg    402
Arg Cys Tyr Thr Asp Trp Val Ser His Asn Asn Met Thr Lys Cys Pro
 90                  95                 100                 105 tga gctaagcgcg cacgaatacg atccgtctgc ctgcctagat ctagcttaat          455
* ttagctttgc attgctccta gttgagtagt tggtgttgtc cgttgggttt ctgtctttcc    515
agagttatcc ttttttcttt ttctttttttt ttcttcctga gagaagagag ggtgttgacg   575
agctgttact gttagtattc tggacctcta gtatgttttg ttgtgtaaaa aaggactagt    635
gaaatccatc tcggcttgaa tcacgcttga taaaaaaaaa aaaaaaaaa                685

<210> SEQ ID NO 18
<211> LENGTH: 660
<212> TYPE: DNA
<213> ORGANISM: Oryza sativa
<220> FEATURE:
<221> NAME/KEY: CDS
<222> LOCATION: (76)...(330)

<400> SEQUENCE: 18
gcgtcctcca ccaagatccc cttcctcctc ctcgccgtcc tcctcctcct ttccatcgcc    60 ttccatcgg aggtg atg gca gga ggg cgc ggg cgc ggc ggc ggc ggc ggc    111
               Met Ala Gly Gly Arg Gly Arg Gly Gly Gly Gly Gly
                 1               5                  10 gga ggg gtg gcc ggc ggc ggg aac ctg agg ccg tgg gag tgc tcg ccc    159
Gly Gly Val Ala Gly Gly Gly Asn Leu Arg Pro Trp Glu Cys Ser Pro
         15                  20                  25 aag tgc gcg ggg agg tgc tcc aac acg cag tac aag aag gcg tgc ctg    207
Lys Cys Ala Gly Arg Cys Ser Asn Thr Gln Tyr Lys Lys Ala Cys Leu
     30                  35                  40
```

```
acg ttc tgc aac aag tgc tgc gcc aag tgc ctg tgc gtg ccg ccc ggc      255
Thr Phe Cys Asn Lys Cys Cys Ala Lys Cys Leu Cys Val Pro Pro Gly
 45                  50                  55                  60 acg tac ggc aac aag ggc gcc tgc ccc tgc tac aac aac tgg aag acc      303
Thr Tyr Gly Asn Lys Gly Ala Cys Pro Cys Tyr Asn Asn Trp Lys Thr
             65                  70                  75 aag gaa ggc ggc ccc aag tgc ccc taa gatgcatgcc ttttttttctt           350
Lys Glu Gly Gly Pro Lys Cys Pro *
         80 tcttctttt ttttttgtttt ttaccgtat gattaatacc tcctactagt tctactacat     410
tggtgtgtca ctgcctcact gacactggtt tagctcatgg atccggttga ttagttaatt    470
ggtggtgggt tttattgcta gatctgggct tataagtatt agtttatcct gttctagtaa    530
ggttgttggt tgggggaatg tgtgcgagag aggagagtga ggattcgtca aagctggtca    590
aaaacttgga tcccctctcc ctgtagtgat tgattgattt gctactactg gagtgtgctt    650
tgccggaaaa                                                           660

<210> SEQ ID NO 19
<211> LENGTH: 677
<212> TYPE: DNA
<213> ORGANISM: Glycine max
<220> FEATURE:
<221> NAME/KEY: CDS
<222> LOCATION: (145)...(411)

<400> SEQUENCE: 19
cctaaataag catcataaat tcatagtctt tcggtccttc cttccttcct ccgctctagt     60
gtatgccact ctggttaatt atcataccc cttctaggca tagttcttct ccctctgttc    120
tctattctac actgtgaaac caag atg aag gta gca ttt gta gct gtt cta      171
                           Met Lys Val Ala Phe Val Ala Val Leu
                            1               5 ctt att tgc ctt gtc cta agc tcc tcc ttg ttc gag gtg tca atg gcc     219
Leu Ile Cys Leu Val Leu Ser Ser Ser Leu Phe Glu Val Ser Met Ala
 10                  15                  20                  25 ggt tct gct ttc tgc tcc tcc aag tgc gcg aag agg tgt tct agg gct     267
Gly Ser Ala Phe Cys Ser Ser Lys Cys Ala Lys Arg Cys Ser Arg Ala
                 30                  35                  40 ggg atg aag gac agg tgc acg agg ttc tgc ggg att tgc tgc agc aag     315
Gly Met Lys Asp Arg Cys Thr Arg Phe Cys Gly Ile Cys Cys Ser Lys
             45                  50                  55 tgt agg tgt gtg cca tct ggg act tat ggg aac aag cac gag tgc cct     363
Cys Arg Cys Val Pro Ser Gly Thr Tyr Gly Asn Lys His Glu Cys Pro
         60                  65                  70 tgc tac aga gac atg aag aac tcc aag ggc aag ccc aaa tgc cct tga     411
Cys Tyr Arg Asp Met Lys Asn Ser Lys Gly Lys Pro Lys Cys Pro *
     75                  80                  85 ttgttaattt caccatgcat caacttcaat ctcaaacctt tgaatccttc actcttgcta    471
gctgattaag ttttctacct ttattattat tgtgtttgtg tatttatata aagagaaaaa    531
tttggtcact ttagttgaat cgggtatgca tgatatacat gagtgggaat aaatcgtggt    591
cttctttgtc cacctgtgaa tttggtctgt cttaataaaa gtgaattctc ctggttaaaa    651
aaaaaaaaaa aaaaaaaaaa aaaaaa                                         677

<210> SEQ ID NO 20
<211> LENGTH: 756
<212> TYPE: DNA
<213> ORGANISM: Glycine max
```

```
<220> FEATURE:
<221> NAME/KEY: CDS
<222> LOCATION: (147)...(413)

<400> SEQUENCE: 20
cctaaataag catcttaatt catagtctct tggtccttcc ttccttcttc tgctcaataa      60
gtgtgtgcca ctctaattaa ttaccacccc cttctagaca tagttcttct ccctctgttc     120
tctattctct acactgtgaa accaag atg aag gta gca ttt gca gct gtt cta     173
                            Met Lys Val Ala Phe Ala Ala Val Leu
                              1               5 ctt ata tgc ctt gtc ctc agc tcc tcc ttg ttc gag gtg tca atg gct     221
Leu Ile Cys Leu Val Leu Ser Ser Ser Leu Phe Glu Val Ser Met Ala
 10              15                  20                  25 ggt tct gct ttc tgt tcc tcc aag tgt tcg aag agg tgt tct aga gct     269
Gly Ser Ala Phe Cys Ser Ser Lys Cys Ser Lys Arg Cys Ser Arg Ala
                 30                  35                  40 ggg atg aag gac agg tgc atg aag ttc tgc ggg att tgc tgc agc aag     317
Gly Met Lys Asp Arg Cys Met Lys Phe Cys Gly Ile Cys Cys Ser Lys
             45                  50                  55 tgc aac tgt gtg cca tct ggg act tat ggg aac aag cat gag tgc cct     365
Cys Asn Cys Val Pro Ser Gly Thr Tyr Gly Asn Lys His Glu Cys Pro
         60                  65                  70 tgc tac aga gac atg aag aac tcc aag ggc aag gcc aaa tgc cct tga     413
Cys Tyr Arg Asp Met Lys Asn Ser Lys Gly Lys Ala Lys Cys Pro  *
     75                  80                  85 ttattttttt ttttcaccat ccacacatca acttcaagcc tttgattcag tcactaccgt     473
gcatgtatat ctccacctta gagatattcc accatggacc cttgctagct gattatgttt     533
actaccttta ttgttgtgtt tgtgtattac ataaagagaa aaatttggtc actttagttg     593
gatcggatat gcatgataca tgagagtgag aataaatcgg ggtcttcttt gtcctcgtgt     653
gaatttggtc tgtcttaatt aggctctatg gatagtaat aaaaatgaat tctccttttg     713
taaaaaaaaa aaaaaaaaa aaaaaaaaaa aaaaaaaaa aaa                         756

<210> SEQ ID NO 21
<211> LENGTH: 579
<212> TYPE: DNA
<213> ORGANISM: Glycine max
<220> FEATURE:
<221> NAME/KEY: CDS
<222> LOCATION: (83)...(349)

<400> SEQUENCE: 21
tagtaagctc ttttaaagtt ctggcccgaa ccctttcttt cgtcacaatc acaacttggt      60
aaaggtactc cgtgcaagaa ag atg aag ctc gag ttc gca aat gtg cta ctt     112
                         Met Lys Leu Glu Phe Ala Asn Val Leu Leu
                           1               5                  10 ctg tgc ctt gtc ctt agc tct tct ttc ttg gaa atc tca atg gct ggt     160
Leu Cys Leu Val Leu Ser Ser Ser Phe Leu Glu Ile Ser Met Ala Gly
                 15                  20                  25 tct cct ttc tgt gac tca aag tgc gcg cag agg tgt gcc aaa gct ggg     208
Ser Pro Phe Cys Asp Ser Lys Cys Ala Gln Arg Cys Ala Lys Ala Gly
             30                  35                  40 gtt cag gac aga tgc ttg agg ttt tgc ggg atc tgc tgc gag aag tgc     256
Val Gln Asp Arg Cys Leu Arg Phe Cys Gly Ile Cys Cys Glu Lys Cys
         45                  50                  55 aac tgt gtc cca tct ggg act tac gga aac aag gac gag tgc cct tgc     304
Asn Cys Val Pro Ser Gly Thr Tyr Gly Asn Lys Asp Glu Cys Pro Cys
     60                  65                  70
```

```
tac agg gac atg aag aac tcc aag ggc aag gac aaa tgc cct tga      349
Tyr Arg Asp Met Lys Asn Ser Lys Gly Lys Asp Lys Cys Pro *
 75                  80                  85 agaatatcta atttcatcat cacactccat tccaataaac taccttgtat tgtatcttca  409
gccttccttt tcagagtatt gcattatgcc acggatctat gtacctaccc ttcaacttaa  469
gtattccgtc tagttaatta gcatagctac ccttcaactt atgtgttccg acctagttaa  529
ttagcttatt aattatttac gagagtaaaa aaaaaaaaa aaaaaaaaa              579

<210> SEQ ID NO 22
<211> LENGTH: 509
<212> TYPE: DNA
<213> ORGANISM: Glycine max
<220> FEATURE:
<221> NAME/KEY: CDS
<222> LOCATION: (52)...(324)

<400> SEQUENCE: 22
gttgaaacac acctactaca attgctaaag tcctttcttg tcatagcaaa a atg aag   57
                                                        Met Lys
                                                          1 ctt gtc ttt gcc acc cta ctg tta tgt tct ctt ctt cta agc tcc tct  105
Leu Val Phe Ala Thr Leu Leu Leu Cys Ser Leu Leu Leu Ser Ser Ser
      5                  10                  15 ttc ttg gag cca gtc atc gcc tat gaa gac tcg tct tat tgc agc aac  153
Phe Leu Glu Pro Val Ile Ala Tyr Glu Asp Ser Ser Tyr Cys Ser Asn
 20                  25                  30 aag tgt tcg gac aga tgc tca tcg gca ggg gtt aag gat agg tgt ctg  201
Lys Cys Ser Asp Arg Cys Ser Ser Ala Gly Val Lys Asp Arg Cys Leu
 35                  40                  45                  50 agg tac tgt gga ata tgc tgt gct gag tgc aaa tgt gtt cct tct ggg  249
Arg Tyr Cys Gly Ile Cys Cys Ala Glu Cys Lys Cys Val Pro Ser Gly
              55                  60                  65 acc tat ggg aac aag cac cag tgt cct tgc tac agg gac aag ctc aac  297
Thr Tyr Gly Asn Lys His Gln Cys Pro Cys Tyr Arg Asp Lys Leu Asn
         70                  75                  80 aag aag ggc aag ccc aaa tgc cca tga agtcttgaac tcaaagacca         344
Lys Lys Gly Lys Pro Lys Cys Pro *
     85                  90 agtcacatag agacttaaga gaataagact ggtgtttgtg tttacaatta catcgtgaat  404
tcccaagcgt aatggttgga ctcttgtttc caatgtctgt tggatatatg ttagatctga  464
acgggaataa attacatatc ttggataaaa aaaaaaaaa aaaaa                   509

<210> SEQ ID NO 23
<211> LENGTH: 439
<212> TYPE: DNA
<213> ORGANISM: Glycine max
<220> FEATURE:
<221> NAME/KEY: CDS
<222> LOCATION: (17)...(289)

<400> SEQUENCE: 23
gtccttactt gcaaca atg aag ctt gtc ttt ggc acc cta cta tta tgt tct   52
               Met Lys Leu Val Phe Gly Thr Leu Leu Leu Cys Ser
                 1               5                  10 ctt ctt cta agc ttc tct ttc ttg gag cca gtc ata gcc tat gaa gac  100
Leu Leu Leu Ser Phe Ser Phe Leu Glu Pro Val Ile Ala Tyr Glu Asp
         15                  20                  25 tca tct tat tgc agc aac aag tgt gcg gac aga tgc tca tcg gca ggg  148
Ser Ser Tyr Cys Ser Asn Lys Cys Ala Asp Arg Cys Ser Ser Ala Gly
 30                  35                  40
```

```
gtt aag gat agg tgt gtg aag tac tgt gga ata tgc tgt gct gag tgc       196
Val Lys Asp Arg Cys Val Lys Tyr Cys Gly Ile Cys Cys Ala Glu Cys
 45                  50                  55                  60 aaa tgt gtt cct tct ggg acc tat ggg aac aag cac gag tgt cct tgc       244
Lys Cys Val Pro Ser Gly Thr Tyr Gly Asn Lys His Glu Cys Pro Cys
             65                  70                  75 tac agg gac aag ctc aac aag aag ggc aag ccc aaa tgc cct tga           289
Tyr Arg Asp Lys Leu Asn Lys Lys Gly Lys Pro Lys Cys Pro  *
                 80                  85                  90 acttcaactc aaacaccaag tcgaatagag acttaagagt agtagttttt gcatgtggtt     349
gtattcttgt tttcaatgtc tgttgggtat gttagatctg aacaggaata aattacacat     409
cctctctgtc tcaaaaaaaa aaaaaaaaa                                       439

<210> SEQ ID NO 24
<211> LENGTH: 783
<212> TYPE: DNA
<213> ORGANISM: Glycine max
<220> FEATURE:
<221> NAME/KEY: CDS
<222> LOCATION: (55)...(345)

<400> SEQUENCE: 24
tgtcactctc tctttgtctt aaaacctttg ttttgctttt gccactaatt aact atg        57
                                                            Met
                                                             1 gcc atc tca aaa agc aca gtg gtc gta gtt att ctc tgc ttc atc ctt       105
Ala Ile Ser Lys Ser Thr Val Val Val Ile Leu Cys Phe Ile Leu
             5                  10                  15 ata caa gag ttg ggg atc tat ggt gaa gat cca cac atg gat gct gcc       153
Ile Gln Glu Leu Gly Ile Tyr Gly Glu Asp Pro His Met Asp Ala Ala
         20                  25                  30 aag aag ata gat tgc ggt ggc aag tgc aat tcc agg tgc agt aag gct       201
Lys Lys Ile Asp Cys Gly Gly Lys Cys Asn Ser Arg Cys Ser Lys Ala
 35                  40                  45 agg agg caa aaa atg tgc att agg gca tgc aat agt tgc tgc aag aag       249
Arg Arg Gln Lys Met Cys Ile Arg Ala Cys Asn Ser Cys Cys Lys Lys
 50                  55                  60                  65 tgc agg tgc gtg cca ccc ggc act tct ggg aac cga gat ttg tgc cct       297
Cys Arg Cys Val Pro Pro Gly Thr Ser Gly Asn Arg Asp Leu Cys Pro
             70                  75                  80 tgc tat gct aga ctc acc aca cat gga gga aag ctc aag tgc cca tga       345
Cys Tyr Ala Arg Leu Thr Thr His Gly Gly Lys Leu Lys Cys Pro  *
         85                  90                  95 aatgatgact cgatcagaga cgtctagcta agactagcac catatgcatg catgcagtta     405
aataaatgca attaataata ttttgtctga acgtaactac gtggtaatat ggtcgtcgat     465
cgaggaatga ggcaccgagg aagaacata  gatagcacca aattaacgag ctccttggcc     525
agcaaagtgg gaaatggat  gactaagatc ttgatgttgt ttttaatttt tatgctgcac     585
tatatttcct ttatcatata tatatatata tatatgataa agcgaatgta                645
tgatgttaat ttgaggctta ataataatgt tagtcaatgt tagtactagt ttgcttcttt     705
aattagcata aaaatttcct ttatcatata tatatatata aataagtttg attttgtgca     765
aaaaaaaaaa aaaaaaaa                                                   783

<210> SEQ ID NO 25
<211> LENGTH: 607
<212> TYPE: DNA
<213> ORGANISM: Glycine max
```

```
<220> FEATURE:
<221> NAME/KEY: CDS
<222> LOCATION: (39)...(386)

<400> SEQUENCE: 25
caaacactct agaatttgca tgcactgttc ttcataca atg gca tta cgc gag ctt      56
                                         Met Ala Leu Arg Glu Leu
                                           1               5 ctt atg atg ggg ata ttg ctg ctg gta tgt ctt gct aag gtt tca tct      104
Leu Met Met Gly Ile Leu Leu Leu Val Cys Leu Ala Lys Val Ser Ser
         10                  15                  20 gat gtt aac atg caa aag gaa gaa gat gaa gaa ctt cgc ttt cct aat      152
Asp Val Asn Met Gln Lys Glu Glu Asp Glu Glu Leu Arg Phe Pro Asn
             25                  30                  35 cac cct ctt atc gtg aga gac ggg aac aga agg cta atg caa gac ata      200
His Pro Leu Ile Val Arg Asp Gly Asn Arg Arg Leu Met Gln Asp Ile
 40                  45                  50 gat tgc gga gga ttg tgc aag aca agg tgc agt gcc cat tcg agg cca      248
Asp Cys Gly Gly Leu Cys Lys Thr Arg Cys Ser Ala His Ser Arg Pro
 55                  60                  65                  70 aac gtg tgc aac agg gct tgt ggc acg tgt tgt gtg agg tgc aag tgt      296
Asn Val Cys Asn Arg Ala Cys Gly Thr Cys Cys Val Arg Cys Lys Cys
                 75                  80                  85 gtt ccc cca gga act tca ggc aac agg gag ctc tgt ggg acc tgc tat      344
Val Pro Pro Gly Thr Ser Gly Asn Arg Glu Leu Cys Gly Thr Cys Tyr
             90                  95                 100 act gat atg atc act cac ggc aac aag acc aag tgt ccg tag              386
Thr Asp Met Ile Thr His Gly Asn Lys Thr Lys Cys Pro  *
            105                 110                 115 agcccggccc attgaaggtc agccctatcc aattgggccc ttcacacacc gagttgatta    446
caccaagcaa agttagtcta gtttagtaaa taataaatat gggttatgta cacttttatg    506
gatttggatt ttgcatctta agatcgtgtt ctagttttta cctttgttat aatgtatcgt    566
attgttggag ccaagtttat aaaaaaaaaa aaaaaaaaa a                         607

<210> SEQ ID NO 26
<211> LENGTH: 788
<212> TYPE: DNA
<213> ORGANISM: Glycine max
<220> FEATURE:
<221> NAME/KEY: CDS
<222> LOCATION: (160)...(513)

<400> SEQUENCE: 26
ccagtgctgc attttctttc gtctatataa tgctgctatg ccagtaatgt gtgaactgtg     60
aagtgtattg gtcactgacc tatcttggaa gagttttgaa gtttaaacct tcaaaccctt    120
ttgcctttag attctgattc tgagtctctg ctgctatat atg gcg cca cgc gta      174
                                              Met Ala Pro Arg Val
                                                1               5 ttt ctt gtg ttg ggg atg ttg ctg atg gtg tgc ctt gtt aag gtt tcg      222
Phe Leu Val Leu Gly Met Leu Leu Met Val Cys Leu Val Lys Val Ser
             10                  15                  20 tct gat cca aag aga gaa gaa gaa ata ctg gaa gaa gaa cta cat ttt      270
Ser Asp Pro Lys Arg Glu Glu Glu Ile Leu Glu Glu Glu Leu His Phe
         25                  30                  35 ccc gat aac gag cca ctt att gtg aga gac ggg aac aga agg cta atg      318
Pro Asp Asn Glu Pro Leu Ile Val Arg Asp Gly Asn Arg Arg Leu Met
 40                  45                  50 caa gac ata gat tgt ggt ggg ttg tgc aag acg agg tgc agt gca cat      366
Gln Asp Ile Asp Cys Gly Gly Leu Cys Lys Thr Arg Cys Ser Ala His
 55                  60                  65
```

-continued

```
                55                  60                  65
tcg aga ccc aac ttg tgc act agg gcg tgt ggc acg tgt tgt gtg agg      414
Ser Arg Pro Asn Leu Cys Thr Arg Ala Cys Gly Thr Cys Cys Val Arg
 70                  75                  80                  85 tgt aag tgt gtc cca cct ggc aca tct gga aat agg gaa cta tgt gga      462
Cys Lys Cys Val Pro Pro Gly Thr Ser Gly Asn Arg Glu Leu Cys Gly
             90                  95                 100 act tgc tac act gat atg act acc cat ggc aac aag acc aag tgc cct      510
Thr Cys Tyr Thr Asp Met Thr Thr His Gly Asn Lys Thr Lys Cys Pro
            105                 110                 115 tag agaaaaaacc cattgggaaa tttgtgcttc attgattatg caccgaagtt           563
* caagtgtact agtatgtggt ggttcaattc tgtttactat agcgatgtgt gtgcactact    623
ttggctatat tattagacta atagtatgtt tatttagaat gtgtaagttc tagtttgtgt    683
ctgtattatt tcggtgatg ggtcatgtaa acttttgtgc ctttgtttgc ctgaacataa     743
agatagtagt acattacctt tttattaaaa aaaaaaaaaa aaaaa                    788

<210> SEQ ID NO 27
<211> LENGTH: 996
<212> TYPE: DNA
<213> ORGANISM: Glycine max
<220> FEATURE:
<221> NAME/KEY: CDS
<222> LOCATION: (314)...(673)

<400> SEQUENCE: 27
tttttttttt ttttagacaa gtggcagtaa aaccacaaaa acatttaaat gttcaaaagc     60
caccggaaga ggtttaccac aattaagttc aacaaaata aaaatagaaa aaacaaatga    120
catgctagtc accattaaga agaaaacagc aacaaggaat gtgacatcgg agtaaaataa    180
ccagagagct catgccatta tcttggcaga cctaacgtaa agactgtcca cgactttccc    240
aacatttgaa gtttaaacct tcaaattaat caaaccattt taatttgcct atagattctg    300
agtcactgct gct atg gcg cta cgc gta ctt ctt gtg ttg ggg atg ttg      349
                Met Ala Leu Arg Val Leu Leu Val Leu Gly Met Leu
                 1               5                  10 ctg atg ttg tgc ctt gtt aag gtt tca tct gat cca aag ata gaa gaa      397
Leu Met Leu Cys Leu Val Lys Val Ser Ser Asp Pro Lys Ile Glu Glu
        15                  20                  25 gaa ata ctg gaa gca gaa gaa gaa ctg cag ttt ccc gat aac gag cca      445
Glu Ile Leu Glu Ala Glu Glu Glu Leu Gln Phe Pro Asp Asn Glu Pro
     30                  35                  40 ctt atc gtg aga gac gcg aac aga agg cta atg caa gat atg gat tgt      493
Leu Ile Val Arg Asp Ala Asn Arg Arg Leu Met Gln Asp Met Asp Cys
 45                  50                  55                  60 ggt ggg ttg tgc aag acg agg tgc agt gca cat tcg agg ccc aac ttg      541
Gly Gly Leu Cys Lys Thr Arg Cys Ser Ala His Ser Arg Pro Asn Leu
             65                  70                  75 tgc act agg gcg tgt ggc acg tgt tgt gtg agg tgt aag tgt gtc cca      589
Cys Thr Arg Ala Cys Gly Thr Cys Cys Val Arg Cys Lys Cys Val Pro
        80                  85                  90 cct ggt aca tct gga aat agg gaa cta tgt gga act tgc tac act gat      637
Pro Gly Thr Ser Gly Asn Arg Glu Leu Cys Gly Thr Cys Tyr Thr Asp
     95                 100                 105 atg acc acc cat ggc aac aag acc aag tgc cct tag agaaacaaaa           683
Met Thr Thr His Gly Asn Lys Thr Lys Cys Pro *
            110                 115 agcttcatta gattggccaa tttgtgcttc gttcattatg catcaaagtt taagtgtact    743
```

```
cctatgtggg gtgcaattct gtttactata gcgatggatt tgtgtgcact actatggcta    803
tattaattga ctgttagtgt ttttatttag ggtgtgcctg tatgattgat gtgatgagct    863
agtcatgtaa actttgtgcc tttgtttgcg ttaatataaa atgtagtaca tcactgtacc    923
tttttatttc caaaaaaaaa aaaaaaaaaa aaaaaaaaaa aaaaaaaaaa aaaaaaaaaa    983
aaaaaaaaaa aaa                                                       996

<210> SEQ ID NO 28
<211> LENGTH: 615
<212> TYPE: DNA
<213> ORGANISM: Glycine max
<220> FEATURE:
<221> NAME/KEY: CDS
<222> LOCATION: (64)...(363)

<400> SEQUENCE: 28
aatcaaaaca ttcccaataa caataatata cacatcttca attaagctcc ttctcctata     60 gcc atg gct ctt tct aag ctt ata att gct tcc ctt ctt gcg tcg ctt     108
    Met Ala Leu Ser Lys Leu Ile Ile Ala Ser Leu Leu Ala Ser Leu
    1               5                  10                  15 ctc ctt ctt cat ttc gtt gat gct gat caa tcg gca cat gca caa acg     156
Leu Leu Leu His Phe Val Asp Ala Asp Gln Ser Ala His Ala Gln Thr
            20                  25                  30 cag ggg tct ctt ctt cag cag ata gat tgt aac gga gca tgt gct gcg     204
Gln Gly Ser Leu Leu Gln Gln Ile Asp Cys Asn Gly Ala Cys Ala Ala
        35                  40                  45 agg tgc cgt tta tca tct cgt cca cgc ctc tgc caa aga gct tgt gga     252
Arg Cys Arg Leu Ser Ser Arg Pro Arg Leu Cys Gln Arg Ala Cys Gly
    50                  55                  60 act tgt tgt aga cgc tgt aac tgc gtg cca cct ggc act gct gga aac     300
Thr Cys Cys Arg Arg Cys Asn Cys Val Pro Pro Gly Thr Ala Gly Asn
65                  70                  75 caa gaa gtg tgt ccc tgc tat gca agt ttg act act cat ggt ggc aaa     348
Gln Glu Val Cys Pro Cys Tyr Ala Ser Leu Thr Thr His Gly Gly Lys
 80                  85                  90                  95 cgc aag tgc cct tag acttaattgg accactatcc tatgcatgcc tttgatttat     403
Arg Lys Cys Pro  * attataaaat aaaataata ctatatataa catgttaatt gcttaatatg tgctttaaga    463
gtaaagaata acatcgtgaa atcaaattac ccctttttca atacgtgttg aatcatcgat    523
cttggtttgt aatttggttg tatattcaca aaattaataa gtatattgtg atgtgattaa    583
ttcccttctc aaaaaaaaaa aaaaaaaaaa aa                                  615

<210> SEQ ID NO 29
<211> LENGTH: 628
<212> TYPE: DNA
<213> ORGANISM: Zea mays
<220> FEATURE:
<221> NAME/KEY: CDS
<222> LOCATION: (49)...(396)

<400> SEQUENCE: 29
tcctcctcat atacagtaca aacttcagct ggtagatagt gcttccaa atg gag aag     57
                                                    Met Glu Lys
                                                      1 aaa agg aag act tta cta ttg ctg ctg ctc atg gct gca act ctc ttc    105
Lys Arg Lys Thr Leu Leu Leu Leu Leu Leu Met Ala Ala Thr Leu Phe
  5                  10                  15 tgc atg cca att gtg tcg tat gct gtt tct agt gtc aac att caa ggt    153
Cys Met Pro Ile Val Ser Tyr Ala Val Ser Ser Val Asn Ile Gln Gly
```

```
                Cys Met Pro Ile Val Ser Tyr Ala Val Ser Ser Val Asn Ile Gln Gly
                 20                  25                  30                  35 cat ctc acc cat tct gag ctg gta aaa ggt ccc aat aga agg ctt ttg              201
His Leu Thr His Ser Glu Leu Val Lys Gly Pro Asn Arg Arg Leu Leu
             40                  45                  50 cca ttt gtg gat tgt gga gcg agg tgc agg gtg agg tgc agt ttg cac              249
Pro Phe Val Asp Cys Gly Ala Arg Cys Arg Val Arg Cys Ser Leu His
         55                  60                  65 tca agg cca aaa att tgc tca aga gct tgc ggg aca tgc tgt ttc agg              297
Ser Arg Pro Lys Ile Cys Ser Arg Ala Cys Gly Thr Cys Cys Phe Arg
     70                  75                  80 tgc agg tgt gtt cct cca ggc act tac ggg aac aga gag atg tgt ggc              345
Cys Arg Cys Val Pro Pro Gly Thr Tyr Gly Asn Arg Glu Met Cys Gly
 85                  90                  95 aag tgt tac act gac atg atc act cat ggc aac aaa cct aag tgc ccc              393
Lys Cys Tyr Thr Asp Met Ile Thr His Gly Asn Lys Pro Lys Cys Pro
100                 105                 110                 115 taa acctgtgcat gcatgcccat gtgtgtctac acctatgat gtttatcact                    446
* agttaacaca aatttgaatt cccattttt tgttttttct accttaattt cttaatgcat             506
tgtgtttctc ataatttgta accatcagtt ttgtgttttt tttcttctga acatcatcag            566
ttttgtgtat tgctgcgatt taatgcatct atatataatg caaaaaaaaa aaaaaaaaaa            626
aa                                                                           628

<210> SEQ ID NO 30
<211> LENGTH: 1066
<212> TYPE: DNA
<213> ORGANISM: Glycine max
<220> FEATURE:
<221> NAME/KEY: CDS
<222> LOCATION: (189)...(764)

<400> SEQUENCE: 30
aggattacgc caagctcgaa attaaccctc actaagggga acaaaagctg gagctccacc             60
gcggtggcgg ccgctctaga actagtggat ccccccgggct gcaggtggaa ctaacacaca          120
ctgaagaata gcagcaagta gtagctcttg acccttcttt ccacctttc tggtccctcc            180 ctccagaa atg gct tct aat tcc att ctt ctt ctt tgt atc ttt ctt gtg            230
         Met Ala Ser Asn Ser Ile Leu Leu Leu Cys Ile Phe Leu Val
          1               5                  10 gtt gcc act aag gtt ttt tcc tat gat gaa gat ctc aag aca gtg gtt              278
Val Ala Thr Lys Val Phe Ser Tyr Asp Glu Asp Leu Lys Thr Val Val
 15                  20                  25                  30 cct gca cct gct cca cca gtg aag gca cca act ctt gcc cct cca gtg              326
Pro Ala Pro Ala Pro Pro Val Lys Ala Pro Thr Leu Ala Pro Pro Val
             35                  40                  45 aaa tca cca tct tac cct cca ggg cca gtg acc aca cca aca gtt cca              374
Lys Ser Pro Ser Tyr Pro Pro Gly Pro Val Thr Thr Pro Thr Val Pro
         50                  55                  60 aca ccc act gtt aag gta ccc cct ccc cct cag tct cca gta gtt aag              422
Thr Pro Thr Val Lys Val Pro Pro Pro Pro Gln Ser Pro Val Val Lys
     65                  70                  75 cca cca aca cca aca gtt cca cca ccc act gtt aag gta ccc cct ccc              470
Pro Pro Thr Pro Thr Val Pro Pro Pro Thr Val Lys Val Pro Pro Pro
 80                  85                  90 cct cag tct cca gta gta aag cca cca act cca aca cca act tcc cca              518
Pro Gln Ser Pro Val Val Lys Pro Pro Thr Pro Thr Pro Thr Ser Pro
 95                 100                 105                 110
```

-continued

| | | |
|---|---|---|
| gtg gtg tac cct cct cct gtt gct cca tct cca cca gct cct gta gtg<br>Val Val Tyr Pro Pro Pro Val Ala Pro Ser Pro Pro Ala Pro Val Val<br>              115                        120                    125 | 566 |
| aaa tca aac aag gat tgc att cca cta tgt gat tat agg tgc tca tta<br>Lys Ser Asn Lys Asp Cys Ile Pro Leu Cys Asp Tyr Arg Cys Ser Leu<br>          130                        135                        140 | 614 |
| cac tca agg aag aaa ttg tgc atg aga gca tgc ata acc tgt tgt gac<br>His Ser Arg Lys Lys Leu Cys Met Arg Ala Cys Ile Thr Cys Cys Asp<br>145                        150                        155 | 662 |
| cga tgc aaa tgt gtc cct cct gga act tat ggt aac agg gaa aag tgt<br>Arg Cys Lys Cys Val Pro Pro Gly Thr Tyr Gly Asn Arg Glu Lys Cys<br>      160                      165                        170 | 710 |
| ggc aag tgc tac act gac atg ctg act cac ggc aac aaa ttc aag tgc<br>Gly Lys Cys Tyr Thr Asp Met Leu Thr His Gly Asn Lys Phe Lys Cys<br>175                  180                        185                    190 | 758 |
| cca tag aagaagccta atatctagta acttacctaa gcttttttgt taatcaagtt<br>Pro  * | 814 |
| tgaatcatga gtaatgtggt ttgagttgct agtgtattta ataaccgaga gtgataatca | 874 |
| taattgtaca agctatcgtg ttaatcaaaa tagtcaacac tgtttgtgtt gtctatagga | 934 |
| tccatttgtg gtccatgaag aagtttatat tcataatgat taatataagg atgtattgct | 994 |
| gtacgaaatt cagaactata attaaatatg aatatgacct tgctaaattt gattcaaaaa | 1054 |
| aaaaaaaaaa aa | 1066 |

<210> SEQ ID NO 31
<211> LENGTH: 697
<212> TYPE: DNA
<213> ORGANISM: Glycine max
<220> FEATURE:
<221> NAME/KEY: CDS
<222> LOCATION: (110)...(433)

<400> SEQUENCE: 31

| | | |
|---|---|---|
| caaaactcaa gcattgcatc cctcttgatt tgtagtttgt tttgtgcttt agataaaagt | 60 |
| tctgccaaat caagagggt tttaagatca tagtgtgtgt tttgcaaca atg gct aag<br>                                                                           Met Ala Lys<br>                                                                           1 | 118 |
| ttc ttt gct gct atg atc ttg gca ctc ttt gcc att tcc ata ctt caa<br>Phe Phe Ala Ala Met Ile Leu Ala Leu Phe Ala Ile Ser Ile Leu Gln<br>     5                        10                        15 | 166 |
| aca gtg gta atg gct gct aat gaa caa gga ggc cac ttg tat gac aac<br>Thr Val Val Met Ala Ala Asn Glu Gln Gly Gly His Leu Tyr Asp Asn<br> 20                        25                        30                        35 | 214 |
| aag agc aaa tat gga agt gga agt gtc aag agt tac caa tgc cca tca<br>Lys Ser Lys Tyr Gly Ser Gly Ser Val Lys Ser Tyr Gln Cys Pro Ser<br>               40                        45                        50 | 262 |
| caa tgc tcg agg aga tgt agc cag acc caa tac cac aag ccc tgc atg<br>Gln Cys Ser Arg Arg Cys Ser Gln Thr Gln Tyr His Lys Pro Cys Met<br>          55                        60                        65 | 310 |
| ttt ttc tgt cag aag tgc tgc agg aca tgc ctg tgt gtg ccc ccg ggg<br>Phe Phe Cys Gln Lys Cys Cys Arg Thr Cys Leu Cys Val Pro Pro Gly<br>               70                        75                        80 | 358 |
| tat tat ggt aat aaa gct gtg tgc cct tgc tac aac aac tgg aag acc<br>Tyr Tyr Gly Asn Lys Ala Val Cys Pro Cys Tyr Asn Asn Trp Lys Thr<br>85                        90                        95 | 406 |
| aag gaa gga gga ccc aag tgc cct tga gcttcaactt gttcaacttc<br>Lys Glu Gly Gly Pro Lys Cys Pro  *<br>100                        105 | 453 |
| aattgtcgct ttcctacatt tttattgctt ccttccttgt gccaatttaa tgcactagct | 513 |

-continued

```
accaaatgct actagtccct tttggtggca ttctatgata ttatgttttt atgtatttg     573 gtgtatcact ccttgggcct tgtttgcctt taatgagagt ggcttattaa tatcaatata    633
tcacctacca aacttattgc tggcaaaaaa aaaaaaaaaa aaaaaaaaaa aaaaaaaaaa    693
aaaa                                                                 697
```

```
<210> SEQ ID NO 32
<211> LENGTH: 692
<212> TYPE: DNA
<213> ORGANISM: Glycine max
<220> FEATURE:
<221> NAME/KEY: CDS
<222> LOCATION: (114)...(437)

<400> SEQUENCE: 32
```

```
ctcaaacaca aacatccctc ttgatttgaa ggttgttttg tgcttataga taaaagttct     60
gccaaatcaa gagggttttt cagatcatag tgtgtgtgtg tgtgtgttaa aca atg      116
                                                              Met
                                                               1 gct aag ttc ttt gct gct atg atc ttg gca ctc att gcc att tcc atg    164
Ala Lys Phe Phe Ala Ala Met Ile Leu Ala Leu Ile Ala Ile Ser Met
         5                  10                  15 ctt caa aca gtg gtt atg gct gct aat gag caa gga ggc cac ttg tat    212
Leu Gln Thr Val Val Met Ala Ala Asn Glu Gln Gly Gly His Leu Tyr
    20                  25                  30 gac aac aag agc aaa tat gga agt ggg agt gtc aag aga tac caa tgc    260
Asp Asn Lys Ser Lys Tyr Gly Ser Gly Ser Val Lys Arg Tyr Gln Cys
 35                  40                  45 cca tca caa tgc tcg agg aga tgt agc cag acc caa tac cac aag ccc    308
Pro Ser Gln Cys Ser Arg Arg Cys Ser Gln Thr Gln Tyr His Lys Pro
 50                  55                  60                  65 tgc atg ttt ttc tgt cag aag tgc tgc agg aaa tgc ctg tgt gtg ccc    356
Cys Met Phe Phe Cys Gln Lys Cys Cys Arg Lys Cys Leu Cys Val Pro
                 70                  75                  80 ccg ggg tat tat ggt aat aaa gct gtg tgc cct tgc tac aac aac tgg    404
Pro Gly Tyr Tyr Gly Asn Lys Ala Val Cys Pro Cys Tyr Asn Asn Trp
             85                  90                  95 aag acc aag gaa gga gga ccc aag tgc cct tga acttcaactt catcaaattg   457
Lys Thr Lys Glu Gly Gly Pro Lys Cys Pro *
        100                 105 ttgcttttca ctatatttt atcatctccc ttgggccaat ttaatgcact agcttacttt    517
ccctactatt ttacccgtcc taaccaaatg ctccccttt ggtggcactc tacgatatat    577 gttttatgt attttggtgt atcctcctta ggccttgttt gcctttaatg agagtggtta    637
ttaatatcaa tatatcaact ataaaactta ttgctagcaa aaaaaaaaaa aaaaa        692
```

```
<210> SEQ ID NO 33
<211> LENGTH: 702
<212> TYPE: DNA
<213> ORGANISM: Glycine max
<220> FEATURE:
<221> NAME/KEY: CDS
<222> LOCATION: (87)...(419)

<400> SEQUENCE: 33
```

```
atctctcttt gataccctt tgttcttttt ggtgctttaa tttgcactag caaggggggtt    60 ggttttattt ctgtttgctt gcaaca atg gct gtg gct aat aag tta ctt tct   113
                              Met Ala Val Ala Asn Lys Leu Leu Ser
                               1               5
```

```
gtt ttg atc att gcc ctc att gcc att tcc atg ctt caa aca gtg gtt    161
Val Leu Ile Ile Ala Leu Ile Ala Ile Ser Met Leu Gln Thr Val Val
     10                  15                  20                  25 atg gca tct cat gga cat gga ggc cac cac tac aat gac aag aaa aaa    209
Met Ala Ser His Gly His Gly Gly His His Tyr Asn Asp Lys Lys Lys
                 30                  35                  40 tat gga cct ggc agt ctc aaa agc ttc caa tgc cca tca caa tgc tca    257
Tyr Gly Pro Gly Ser Leu Lys Ser Phe Gln Cys Pro Ser Gln Cys Ser
             45                  50                  55 agg agg tgt ggc aag acc cag tac cac aag ccc tgc atg ttt ttc tgt    305
Arg Arg Cys Gly Lys Thr Gln Tyr His Lys Pro Cys Met Phe Phe Cys
         60                  65                  70 cag aag tgt tgt agg aag tgc cta tgt gtg cca ccg ggg tat tat ggg    353
Gln Lys Cys Cys Arg Lys Cys Leu Cys Val Pro Pro Gly Tyr Tyr Gly
     75                  80                  85 aac aaa gca gtg tgc cct tgc tac aac aac tgg aag acc aag gaa gga    401
Asn Lys Ala Val Cys Pro Cys Tyr Asn Asn Trp Lys Thr Lys Glu Gly
 90                  95                 100                 105 gga ccc aaa tgc cct taa taaccttatg ctatgttctt catcaaatta           449
Gly Pro Lys Cys Pro *
                 110 acaaagatat aatatagctt taatttatta tatccatatc ataatttt cttggtcctt    509 tctatgtctt aattaaccaa aaatgtatg tccattttgg tcttagtaat actttgttgt    569 attgaagatg cctttggag atagtgtgtg tgtgggctcc tctgcatcat accactcctt    629 attatggcat tgttggcttt taaatgaagt gtgtctaata ctgttgctgt caaaaaaaaa    689 aaaaaaaaaa aaa                                                    702

<210> SEQ ID NO 34
<211> LENGTH: 783
<212> TYPE: DNA
<213> ORGANISM: Glycine max
<220> FEATURE:
<221> NAME/KEY: CDS
<222> LOCATION: (121)...(441)

<400> SEQUENCE: 34
atttaggctc tcttaaaaca aaggtccctc aaaccacttt ccccacactc tttagtgtgt     60 cattttttt tttgctcttt ccccacaaag aggtcttgga cccttcttct gtgtagtgca    120 atg gcc atg gct aag gtt ttc tgt gtt ctg ctt ctg gca ctc ctt ggc    168
Met Ala Met Ala Lys Val Phe Cys Val Leu Leu Leu Ala Leu Leu Gly
  1               5                  10                  15 att tcc atg atc aca act cag gtt atg gca aca gat tct gct tat cac    216
Ile Ser Met Ile Thr Thr Gln Val Met Ala Thr Asp Ser Ala Tyr His
             20                  25                  30 ttg gat gga agg aat tat gga cct ggg agt ctc aag agc tca cag tgc    264
Leu Asp Gly Arg Asn Tyr Gly Pro Gly Ser Leu Lys Ser Ser Gln Cys
         35                  40                  45 cct tct gaa tgc aca aga aga tgt agc cag aca cag tac cac aag ccc    312
Pro Ser Glu Cys Thr Arg Arg Cys Ser Gln Thr Gln Tyr His Lys Pro
     50                  55                  60 tgc atg gtc ttc tgc aaa caa tgc tgc aaa agg tgc ctt tgt gtt cct    360
Cys Met Val Phe Cys Lys Gln Cys Cys Lys Arg Cys Leu Cys Val Pro
 65                  70                  75                  80 cct ggc tac tat ggg aac aag tct gtg tgc ccc tgc tac aat aac tgg    408
Pro Gly Tyr Tyr Gly Asn Lys Ser Val Cys Pro Cys Tyr Asn Asn Trp
             85                  90                  95 aag acc aag cgt gga gga ccc aaa tgc ccc tga aaattgaaaa tataagcata   461
Lys Thr Lys Arg Gly Gly Pro Lys Cys Pro *
```

```
                   100              105
atttcaccta caatttcata tatactactc aaagtggaac tataaactat atatatatat    521
atatatatat ggccatttct atgttttggg cagcacctac tacagttggg ttgtcactag    581
actaatacca tcttgttctc taccatgaaa ttagttcaat tattaatttc atgaagaaac    641
ctatatgtta ctccctttcc taaacaggta tgagagtggt gttctactaa ttagtcaatt    701
atctttgtca ttgtactttt tttagtttta aaaaaaaaaa aaaaaaaaaa aaaaaaaaaa    761
aaaaaaaaaa aaaaaaaaaa aa                                             783

<210> SEQ ID NO 35
<211> LENGTH: 742
<212> TYPE: DNA
<213> ORGANISM: Glycine max
<220> FEATURE:
<221> NAME/KEY: CDS
<222> LOCATION: (207)...(578)

<400> SEQUENCE: 35
acgccaagct cgaaattaac cctcactaaa gggaacaaaa gctggagctc caccgcggtg     60
gcggccgctc tagaactagt ggatccccg ggctgcagga attcggcacg aggctaactt    120
ctctctattt cttcttttct ctgtgtgagg tccattttg agcaatggcg agaaaactaa     180
gcattgttgt actctgcctt gttcaa atg ctg ctt ctt ctc gtg gaa aac cat    233
                              Met Leu Leu Leu Leu Val Glu Asn His
                                1               5 gcc gag att gtt gtg tcc acc gtt gag gct tca gct ccg cag cct cac    281
Ala Glu Ile Val Val Ser Thr Val Glu Ala Ser Ala Pro Gln Pro His
 10              15                  20                  25 aag aac acc acc cac acc ctg tcc cac gct cca gct ccg cag cct cac    329
Lys Asn Thr Thr His Thr Leu Ser His Ala Pro Ala Pro Gln Pro His
             30                  35                  40 aaa aac acc aag tcc cct gtt ccc aat ttg cag cat ggc atc acc gaa    377
Lys Asn Thr Lys Ser Pro Val Pro Asn Leu Gln His Gly Ile Thr Glu
         45                  50                  55 ggc agt ctt aaa cca caa gaa tgt ggg cca cgt tgc acc gct aga tgc    425
Gly Ser Leu Lys Pro Gln Glu Cys Gly Pro Arg Cys Thr Ala Arg Cys
     60                  65                  70 tca aac aca caa tac aag aaa ccg tgc ctg ttc ttc tgc caa aag tgc    473
Ser Asn Thr Gln Tyr Lys Lys Pro Cys Leu Phe Phe Cys Gln Lys Cys
 75                  80                  85 tgt gcc aag tgc tta tgt gtg cct cct gga act tat ggc aac aag caa    521
Cys Ala Lys Cys Leu Cys Val Pro Pro Gly Thr Tyr Gly Asn Lys Gln
 90                  95                 100                 105 gtt tgc cct tgc tac aac aac tgg aag acc aaa agg gga ggg cca aaa    569
Val Cys Pro Cys Tyr Asn Asn Trp Lys Thr Lys Arg Gly Gly Pro Lys
             110                 115                 120 tgc ccc tga aactataaat tttacctatt aagtctctta attaatgcgt              618
Cys Pro * tgctagttgc taccagcact ccatgtattt atatatgtac ccaccagatt gaaattaagt    678
atcttaattt taatttgaaa aaaaaaaaaa aaaaaaaaaa aaaaaaaaaa aaaaaaaaaa    738
aaaa                                                                 742

<210> SEQ ID NO 36
<211> LENGTH: 652
<212> TYPE: DNA
<213> ORGANISM: Glycine max
<220> FEATURE:
<221> NAME/KEY: CDS
```

<222> LOCATION: (94)...(387)

<400> SEQUENCE: 36

```
tatatattca tctttctctt ttttagcttt tcttttcctc taaaagtgag tccttccttc          60
ttcgatcact tgttaaattc acatatcata gca atg gca gca cgt tcc tac agc         114
                                    Met Ala Ala Arg Ser Tyr Ser
                                      1               5 ccc atc atg gtt gcc ctc tct ttg ctt ctt ttg gtc aca ttc tct aat          162
Pro Ile Met Val Ala Leu Ser Leu Leu Leu Leu Val Thr Phe Ser Asn
         10                  15                  20 gta gct gag gct tat aca cgc agt gga aca ctt cgt cct tca gat tgt          210
Val Ala Glu Ala Tyr Thr Arg Ser Gly Thr Leu Arg Pro Ser Asp Cys
     25                  30                  35 aaa cca aag tgt act tac cgt tgc tct gca act tca cac aag aag cca          258
Lys Pro Lys Cys Thr Tyr Arg Cys Ser Ala Thr Ser His Lys Lys Pro
 40                  45                  50                  55 tgc atg ttt ttc tgc cag aag tgt tgt gct aaa tgc cta tgc gtt cct          306
Cys Met Phe Phe Cys Gln Lys Cys Cys Ala Lys Cys Leu Cys Val Pro
                 60                  65                  70 cct ggt aca tat ggc aac aag caa att tgc cct tgc tac aac agc tgg          354
Pro Gly Thr Tyr Gly Asn Lys Gln Ile Cys Pro Cys Tyr Asn Ser Trp
             75                  80                  85 aag acc aag gaa gga gga ccc aaa tgc cct taa accccttaat tgcctaatat        407
Lys Thr Lys Glu Gly Gly Pro Lys Cys Pro *
         90                  95 ataaataatt taataagcaa tgtaatccta tatgactctt catgagcaat ttttatctc         467 tacatagata agcaatgctc ttttaattgt ttagttgata gcacctgggg acacatttag        527
ttatgttccc ttcagttttc agagggaaaa cttttttttt agcaaattgt attttgtgtt        587
ggtatatatt atatatattg tttatatttt tttaaaaaaa aaaaaaaaaa aaaaaaaaaa        647
aaaaa                                                                    652
```

<210> SEQ ID NO 37
<211> LENGTH: 114
<212> TYPE: PRT
<213> ORGANISM: Zea mays

<400> SEQUENCE: 37

```
Met Val Thr Lys Val Ile Cys Phe Leu Val Leu Ala Ser Val Leu Leu
  1               5                  10                  15

Ala Val Ala Phe Pro Val Ser Ala Leu Arg Gln Gln Val Lys Lys Gly
             20                  25                  30

Gly Gly Gly Glu Gly Gly Gly Gly Ser Val Ser Gly Ser Gly Gly
         35                  40                  45

Gly Asn Leu Asn Pro Trp Glu Cys Ser Pro Lys Cys Gly Ser Arg Cys
 50                  55                  60

Ser Lys Thr Gln Tyr Arg Lys Ala Cys Leu Thr Leu Cys Asn Lys Cys
 65                  70                  75                  80

Cys Ala Lys Cys Leu Cys Val Pro Pro Gly Phe Tyr Gly Asn Lys Gly
                 85                  90                  95

Ala Cys Pro Cys Tyr Asn Asn Trp Lys Thr Lys Glu Gly Gly Pro Lys
                100                 105                 110

Cys Pro
```

<210> SEQ ID NO 38
<211> LENGTH: 95
<212> TYPE: PRT

<213> ORGANISM: Zea mays

<400> SEQUENCE: 38

```
Met Lys Leu Gln Ala Thr Ala Arg Val Ala Gly Leu Leu Phe Leu Val
 1               5                  10                  15

Leu Leu Leu Ala Leu Pro Ser Leu Arg Val Ser Met Ala Gly Ser Gly
             20                  25                  30

Phe Cys Asp Gly Lys Cys Ala Val Arg Cys Ser Lys Ala Ser Arg His
         35                  40                  45

Asp Asp Cys Leu Lys Tyr Cys Gly Ile Cys Cys Ala Thr Cys Asn Cys
 50                  55                  60

Val Pro Ser Gly Thr Ala Gly Asn Lys Asp Glu Cys Pro Cys Tyr Arg
 65                  70                  75                  80

Asp Met Thr Thr Gly His Gly Asn Arg Thr Arg Pro Lys Cys Pro
                 85                  90                  95
```

<210> SEQ ID NO 39
<211> LENGTH: 115
<212> TYPE: PRT
<213> ORGANISM: Zea mays

<400> SEQUENCE: 39

```
Met Ala Pro Ser Lys Leu Ala Val Val Ala Leu Val Ala Ser Leu
 1               5                  10                  15

Leu Leu Leu Thr Thr Ser Asn Thr Lys Leu Gly Leu Phe Val Leu Gly
             20                  25                  30

Gln Ala Ala Pro Gly Ala Tyr Pro Pro Arg Ala Pro Pro His Gln
         35                  40                  45

Ile Val Asp Leu Ala Lys Asp Cys Gly Ala Cys Asp Val Arg Cys
 50                  55                  60

Gly Ala His Ser Arg Lys Asn Ile Cys Thr Arg Ala Cys Leu Lys Cys
 65                  70                  75                  80

Cys Gly Val Cys Arg Cys Val Pro Ala Gly Thr Ala Gly Asn Gln Gln
                 85                  90                  95

Thr Cys Gly Lys Cys Tyr Thr Asp Trp Thr Thr His Gly Asn Lys Thr
             100                 105                 110

Lys Cys Pro
        115
```

<210> SEQ ID NO 40
<211> LENGTH: 100
<212> TYPE: PRT
<213> ORGANISM: Zea mays

<400> SEQUENCE: 40

```
Met Ala Val Ala Lys Pro Pro Leu Gln Thr Ala Ala Val Leu Leu Leu
 1               5                  10                  15

Leu Leu Leu Val Val Ala Ala Ser Trp Leu Gln Thr Val Asp Ala
             20                  25                  30

Ala Ser Gly Phe Cys Ser Ser Lys Cys Ser Val Arg Cys Gly Arg Ala
         35                  40                  45

Ala Ser Ala Arg Ala Arg Gly Ala Cys Met Arg Ser Cys Gly Leu Cys
 50                  55                  60

Cys Glu Glu Cys Asn Cys Val Pro Thr Arg Pro Pro Arg Asp Val Asn
 65                  70                  75                  80

Glu Cys Pro Cys Tyr Arg Asp Met Leu Thr Ala Gly Pro Arg Lys Arg
                 85                  90                  95
```

```
Pro Lys Cys Pro
            100

<210> SEQ ID NO 41
<211> LENGTH: 128
<212> TYPE: PRT
<213> ORGANISM: Zea mays

<400> SEQUENCE: 41

Met Met Thr Thr Met Lys Lys Lys Gln Gln Gln Gln Leu Leu Leu
1               5                   10                  15

Leu Ser Leu Met Phe Leu Val Ala Val Thr Ala Ala Val Ala Ala
                20                  25                  30

Asp Pro His Pro Gln Gln Val Gln Val Gln Gln Gln Gln Ala Gln
            35                  40                  45

Met Arg Ile Asn Arg Ala Thr Arg Ser Leu Leu Pro Gln Pro Pro
        50                  55                  60

Lys Leu Asp Cys Pro Ser Thr Cys Ser Val Arg Cys Gly Asn Asn Trp
65                  70                  75                  80

Lys Asn Gln Met Cys Asn Lys Met Cys Asn Val Cys Cys Asn Lys Cys
                85                  90                  95

Ser Cys Val Pro Pro Gly Thr Gly Gln Asp Thr Arg His Leu Cys Pro
            100                 105                 110

Cys Tyr Asp Thr Met Leu Asn Pro His Thr Gly Lys Leu Lys Cys Pro
            115                 120                 125

<210> SEQ ID NO 42
<211> LENGTH: 96
<212> TYPE: PRT
<213> ORGANISM: Zea mays

<400> SEQUENCE: 42

Met Lys Ala Ile Pro Val Ala Leu Leu Leu Val Leu Val Ala Ala
1               5                   10                  15

Ala Ser Ser Phe Lys His Leu Ala Glu Ala Ala Asp Gly Gly Ala Val
                20                  25                  30

Pro Asp Gly Val Cys Asp Gly Lys Cys Arg Ser Arg Cys Ser Leu Lys
            35                  40                  45

Lys Ala Gly Arg Cys Met Gly Leu Cys Met Met Cys Cys Gly Lys Cys
        50                  55                  60

Gln Gly Cys Val Pro Ser Gly Pro Tyr Ala Ser Lys Asp Glu Cys Pro
65                  70                  75                  80

Cys Tyr Arg Asp Met Lys Ser Pro Lys Asn Gln Arg Pro Lys Cys Pro
                85                  90                  95

<210> SEQ ID NO 43
<211> LENGTH: 129
<212> TYPE: PRT
<213> ORGANISM: Zea mays

<400> SEQUENCE: 43

Met Ala Ser Arg Asn Lys Ala Ala Ala Leu Leu Leu Cys Phe Leu Phe
1               5                   10                  15

Leu Ala Ala Val Ala Ala Ser Ala Ala Glu Met Ile Ala Gly Ser Gly
                20                  25                  30

Ile Gly Asp Gly Glu Gly Glu Glu Leu Asp Lys Gly Gly Gly Gly Gly
            35                  40                  45
```

```
Gly Gly His His Lys His Glu Gly Tyr Lys Asn Lys Asp Gly Lys Gly
    50                  55                  60

Asn Leu Lys Pro Ser Gln Cys Gly Gly Glu Cys Arg Arg Arg Cys Ser
 65                  70                  75                  80

Lys Thr His His Lys Lys Pro Cys Leu Phe Phe Cys Asn Lys Cys Cys
                 85                  90                  95

Ala Lys Cys Leu Cys Val Pro Pro Gly Thr Tyr Gly Asn Lys Glu Thr
                100                 105                 110

Cys Pro Cys Tyr Asn Asn Trp Lys Thr Lys Gly Gly Pro Lys Cys
            115                 120                 125

Pro

<210> SEQ ID NO 44
<211> LENGTH: 94
<212> TYPE: PRT
<213> ORGANISM: Zea mays

<400> SEQUENCE: 44

Met Ala Lys Ala Ser Ser Arg Leu Leu Phe Ser Leu Ser Leu Val Val
  1               5                  10                  15

Leu Leu Leu Leu Val Glu Thr Thr Thr Ser Pro His Gly Gln Ala Asp
                 20                  25                  30

Ala Ile Asp Cys Gly Ala Ser Cys Ser Tyr Arg Cys Ser Lys Ser Gly
                35                  40                  45

Arg Pro Lys Met Cys Leu Arg Ala Cys Gly Thr Cys Cys Gln Arg Cys
    50                  55                  60

Gly Cys Val Pro Pro Gly Thr Ser Gly Asn Glu Asp Val Cys Pro Cys
 65                  70                  75                  80

Tyr Ala Asn Met Lys Thr His Asp Gly Gln His Lys Cys Pro
                 85                  90

<210> SEQ ID NO 45
<211> LENGTH: 145
<212> TYPE: PRT
<213> ORGANISM: Zea mays

<400> SEQUENCE: 45

Met Glu Ser Lys Ser Pro Trp Ser Leu Arg Leu Leu Ile Cys Cys Ala
  1               5                  10                  15

Ala Met Val Ala Ile Ala Leu Leu Pro Gln Gln Gly Gly Gln Ala Ala
                 20                  25                  30

Cys Phe Val Pro Thr Pro Gly Pro Ala Pro Ala Pro Pro Gly Ser Ser
                 35                  40                  45

Ala Thr Asn Thr Asn Ala Ser Ser Ala Ala Pro Arg Pro Ala Lys Pro
     50                  55                  60

Ser Ala Phe Pro Pro Pro Met Tyr Gly Gly Val Thr Pro Gly Thr Gly
 65                  70                  75                  80

Ser Leu Gln Pro His Glu Cys Gly Gly Arg Cys Ala Glu Arg Cys Ser
                 85                  90                  95

Ala Thr Ala Tyr Gln Lys Pro Cys Leu Phe Phe Cys Arg Lys Cys Cys
                100                 105                 110

Ala Ala Cys Leu Cys Val Pro Pro Gly Thr Tyr Gly Asn Lys Asn Thr
                115                 120                 125

Cys Pro Cys Tyr Asn Asn Trp Lys Thr Lys Arg Gly Pro Lys Cys
            130                 135                 140

Pro
```

```
<210> SEQ ID NO 46
<211> LENGTH: 77
<212> TYPE: PRT
<213> ORGANISM: Triticum aestivum

<400> SEQUENCE: 46

Met Gly Gly Gly Asn Gly Gly Ala Gly Gly Gly Lys Leu Lys Pro
 1               5                   10                  15

Trp Glu Cys Ser Ser Lys Cys Ser Ser Arg Cys Ser Gly Thr Gln Tyr
                20                  25                  30

Lys Lys Ala Cys Leu Thr Tyr Cys Asn Lys Cys Cys Ala Thr Cys Leu
            35                  40                  45

Cys Val Pro Pro Gly Thr Tyr Gly Asn Lys Gly Ala Cys Pro Cys Tyr
        50                  55                  60

Asn Asn Trp Lys Thr Lys Glu Gly Gly Pro Lys Cys Pro
65                  70                  75

<210> SEQ ID NO 47
<211> LENGTH: 94
<212> TYPE: PRT
<213> ORGANISM: Triticum aestivum

<400> SEQUENCE: 47

Met Lys Lys Leu Arg Thr Thr Thr Leu Ala Leu Leu Leu Leu Val
 1               5                   10                  15

Phe Leu Ala Ala Ser Ser Leu Arg Ala Ala Met Ala Gly Ser Ala Phe
                20                  25                  30

Cys Asp Gly Lys Cys Gly Val Arg Cys Ser Lys Ala Ser Arg His Asp
            35                  40                  45

Asp Cys Leu Lys Tyr Cys Gly Ile Cys Cys Ala Glu Cys Asn Cys Val
        50                  55                  60

Pro Ser Gly Thr Ala Gly Asn Lys Asp Glu Cys Pro Cys Tyr Arg Asp
65                  70                  75                  80

Lys Thr Thr Gly His Gly Ala Arg Lys Arg Pro Lys Cys Pro
                85                  90

<210> SEQ ID NO 48
<211> LENGTH: 98
<212> TYPE: PRT
<213> ORGANISM: Triticum aestivum

<400> SEQUENCE: 48

Met Lys Lys Leu Arg Thr Thr Thr Ala Thr Thr Leu Ala Leu Ile
 1               5                   10                  15

Leu Leu Leu Val Leu Ile Ala Ala Thr Ser Leu Arg Val Ala Met Ala
                20                  25                  30

Gly Ser Ala Phe Cys Asp Ser Lys Cys Gly Val Arg Cys Ser Lys Ala
            35                  40                  45

Gly Arg His Asp Asp Cys Leu Lys Tyr Cys Gly Ile Cys Cys Ala Glu
        50                  55                  60

Cys Asn Cys Val Pro Ser Gly Thr Ala Gly Asn Lys Asp Glu Cys Pro
65                  70                  75                  80

Cys Tyr Arg Asp Lys Thr Thr Gly His Gly Ala Arg Thr Arg Pro Lys
                85                  90                  95

Cys Pro
```

```
<210> SEQ ID NO 49
<211> LENGTH: 107
<212> TYPE: PRT
<213> ORGANISM: Triticum aestivum

<400> SEQUENCE: 49

Met Lys Pro Leu Pro Val Thr Leu Ala Leu Ala Leu Phe Leu Val
 1               5                  10                  15

Ala Ser Tyr Gln Asp Leu Thr Val Ala Ala Asp Ala Asp Ala
            20                  25                  30

Ala Gly Ala Gly Asp Val Gly Ala Val Pro Val Pro Ser Val Cys
            35                  40                  45

Glu Gly Lys Cys Lys Asn Arg Cys Ser Gln Lys Val Ala Gly Arg Cys
 50                  55                  60

Met Gly Leu Cys Met Met Cys Cys Gly Lys Cys Ala Gly Cys Val Pro
 65                  70                  75                  80

Ser Gly Pro Leu Ala Pro Lys Asp Glu Cys Pro Cys Tyr Arg Asp Met
                85                  90                  95

Lys Ser Pro Lys Ser Gly Arg Pro Lys Cys Pro
                100                 105

<210> SEQ ID NO 50
<211> LENGTH: 98
<212> TYPE: PRT
<213> ORGANISM: Triticum aestivum
<220> FEATURE:
<221> NAME/KEY: VARIANT
<222> LOCATION: (64)...(64)
<223> OTHER INFORMATION: The amino acid at position 64 can be any amino
      acid

<400> SEQUENCE: 50

Met Ser Lys Pro Ser Arg Cys Arg Ala Val Gln Thr Gln Val Ala Leu
 1               5                  10                  15

Leu Leu Leu Leu Leu Val Ala Ala Ser Leu Leu Gln Ala Gly Asp Ala
                20                  25                  30

Ala Ser Gly Phe Cys Ala Gly Lys Cys Ala Val Arg Cys Gly Arg Ser
            35                  40                  45

Arg Ala Lys Arg Gly Ala Cys Met Lys Tyr Cys Gly Leu Cys Cys Xaa
 50                  55                  60

Glu Cys Ala Cys Val Pro Thr Gly Arg Ser Gly Ser Arg Asp Glu Cys
 65                  70                  75                  80

Pro Cys Tyr Arg Asp Met Leu Thr Ala Gly Pro Arg Lys Arg Pro Lys
                85                  90                  95

Cys Pro

<210> SEQ ID NO 51
<211> LENGTH: 114
<212> TYPE: PRT
<213> ORGANISM: Triticum aestivum

<400> SEQUENCE: 51

Met Val Thr Lys Val Ile Cys Phe Leu Val Leu Ala Ser Val Leu Leu
 1               5                  10                  15

Ala Val Ala Phe Pro Val Ser Ala Leu Arg Gln Gln Val Lys Lys Gly
                20                  25                  30

Gly Gly Gly Glu Gly Gly Gly Gly Ser Val Ser Gly Ser Gly Gly
            35                  40                  45
```

-continued

```
Gly Asn Leu Asn Pro Trp Glu Cys Ser Pro Lys Cys Gly Ser Arg Cys
 50                  55                  60

Ser Lys Thr Gln Tyr Arg Lys Ala Cys Leu Thr Leu Cys Asn Lys Cys
 65                  70                  75                  80

Cys Ala Lys Cys Leu Cys Val Pro Pro Gly Phe Tyr Gly Asn Lys Gly
                 85                  90                  95

Ala Cys Pro Cys Tyr Asn Asn Trp Lys Thr Arg Glu Gly Gly Pro Lys
            100                 105                 110

Cys Pro
```

<210> SEQ ID NO 52
<211> LENGTH: 103
<212> TYPE: PRT
<213> ORGANISM: Triticum aestivum

<400> SEQUENCE: 52

```
Met Leu Leu Leu Ala Leu Ala Ala His His Gln Ala Ala Ser Asp Pro
 1               5                  10                  15

Pro Ala Thr His Gly Gly Met Arg Ala Ser Gly Thr Arg Ser Leu Leu
                20                  25                  30

Gln Gln Gln Pro Pro Pro Arg Leu Asp Cys Pro Lys Val Cys Ala
            35                  40                  45

Gly Arg Cys Ala Asn Asn Trp Arg Lys Glu Met Cys Asn Asp Lys Cys
 50                  55                  60

Asn Val Cys Cys Gln Arg Cys Asn Cys Val Pro Pro Gly Thr Gly Gln
 65                  70                  75                  80

Asp Thr Arg His Ile Cys Pro Cys Tyr Ala Thr Met Thr Asn Pro His
                 85                  90                  95

Asn Gly Lys Leu Lys Cys Pro
            100
```

<210> SEQ ID NO 53
<211> LENGTH: 105
<212> TYPE: PRT
<213> ORGANISM: Triticum aestivum

<400> SEQUENCE: 53

```
Met Ala Pro Gly Lys Leu Ala Val Phe Ala Leu Leu Ala Ser Leu Leu
 1               5                  10                  15

Leu Leu Asn Thr Ile Lys Ala Ala Asp Tyr Pro Pro Ala Pro Pro Leu
                20                  25                  30

Gly Pro Pro Pro His Lys Ile Val Asp Pro Gly Lys Asp Cys Val Gly
            35                  40                  45

Ala Cys Asp Ala Arg Cys Ser Glu His Ser His Lys Lys Arg Cys Ser
 50                  55                  60

Arg Ser Cys Leu Thr Cys Cys Ser Ala Cys Arg Cys Val Pro Ala Gly
 65                  70                  75                  80

Thr Ala Gly Asn Arg Glu Thr Cys Gly Arg Cys Tyr Thr Asp Trp Val
                 85                  90                  95

Ser His Asn Asn Met Thr Lys Cys Pro
            100                 105
```

<210> SEQ ID NO 54
<211> LENGTH: 84
<212> TYPE: PRT
<213> ORGANISM: Triticum aestivum

<400> SEQUENCE: 54

```
Met Ala Gly Gly Arg Gly Arg Gly Gly Gly Gly Gly Val Ala
1               5                   10                  15

Gly Gly Gly Asn Leu Arg Pro Trp Glu Cys Ser Pro Lys Cys Ala Gly
            20                  25                  30

Arg Cys Ser Asn Thr Gln Tyr Lys Lys Ala Cys Leu Thr Phe Cys Asn
            35                  40                  45

Lys Cys Cys Ala Lys Cys Leu Cys Val Pro Pro Gly Thr Tyr Gly Asn
50                  55                  60

Lys Gly Ala Cys Pro Cys Tyr Asn Asn Trp Lys Thr Lys Glu Gly Gly
65                  70                  75                  80

Pro Lys Cys Pro

<210> SEQ ID NO 55
<211> LENGTH: 88
<212> TYPE: PRT
<213> ORGANISM: Glycine max

<400> SEQUENCE: 55

Met Lys Val Ala Phe Val Ala Val Leu Leu Ile Cys Leu Val Leu Ser
1               5                   10                  15

Ser Ser Leu Phe Glu Val Ser Met Ala Gly Ser Ala Phe Cys Ser Ser
            20                  25                  30

Lys Cys Ala Lys Arg Cys Ser Arg Ala Gly Met Lys Asp Arg Cys Thr
            35                  40                  45

Arg Phe Cys Gly Ile Cys Cys Ser Lys Cys Arg Cys Val Pro Ser Gly
50                  55                  60

Thr Tyr Gly Asn Lys His Glu Cys Pro Cys Tyr Arg Asp Met Lys Asn
65                  70                  75                  80

Ser Lys Gly Lys Pro Lys Cys Pro
                85

<210> SEQ ID NO 56
<211> LENGTH: 88
<212> TYPE: PRT
<213> ORGANISM: Glycine max

<400> SEQUENCE: 56

Met Lys Val Ala Phe Ala Val Leu Leu Ile Cys Leu Val Leu Ser
1               5                   10                  15

Ser Ser Leu Phe Glu Val Ser Met Ala Gly Ser Ala Phe Cys Ser Ser
            20                  25                  30

Lys Cys Ser Lys Arg Cys Ser Arg Ala Gly Met Lys Asp Arg Cys Met
            35                  40                  45

Lys Phe Cys Gly Ile Cys Cys Ser Lys Cys Asn Cys Val Pro Ser Gly
50                  55                  60

Thr Tyr Gly Asn Lys His Glu Cys Pro Cys Tyr Arg Asp Met Lys Asn
65                  70                  75                  80

Ser Lys Gly Lys Ala Lys Cys Pro
                85

<210> SEQ ID NO 57
<211> LENGTH: 88
<212> TYPE: PRT
<213> ORGANISM: Glycine max

<400> SEQUENCE: 57

Met Lys Leu Glu Phe Ala Asn Val Leu Leu Leu Cys Leu Val Leu Ser
```

```
              1               5                  10                 15
Ser Ser Phe Leu Glu Ile Ser Met Ala Gly Ser Pro Phe Cys Asp Ser
                20                 25                 30

Lys Cys Ala Gln Arg Cys Ala Lys Ala Gly Val Gln Asp Arg Cys Leu
                35                 40                 45

Arg Phe Cys Gly Ile Cys Cys Glu Lys Cys Asn Cys Val Pro Ser Gly
 50                 55                 60

Thr Tyr Gly Asn Lys Asp Glu Cys Pro Cys Tyr Arg Asp Met Lys Asn
 65                 70                 75                 80

Ser Lys Gly Lys Asp Lys Cys Pro
                85
```

<210> SEQ ID NO 58
<211> LENGTH: 90
<212> TYPE: PRT
<213> ORGANISM: Glycine max

<400> SEQUENCE: 58

```
Met Lys Leu Val Phe Ala Thr Leu Leu Cys Ser Leu Leu Leu Leu Ser
 1               5                  10                 15

Ser Ser Phe Leu Glu Pro Val Ile Ala Tyr Glu Asp Ser Ser Tyr Cys
                20                 25                 30

Ser Asn Lys Cys Ser Asp Arg Cys Ser Ser Ala Gly Val Lys Asp Arg
                35                 40                 45

Cys Leu Arg Tyr Cys Gly Ile Cys Cys Ala Glu Cys Lys Cys Val Pro
                50                 55                 60

Ser Gly Thr Tyr Gly Asn Lys His Gln Cys Pro Cys Tyr Arg Asp Lys
 65                 70                 75                 80

Leu Asn Lys Lys Gly Lys Pro Lys Cys Pro
                85                 90
```

<210> SEQ ID NO 59
<211> LENGTH: 90
<212> TYPE: PRT
<213> ORGANISM: Glycine max

<400> SEQUENCE: 59

```
Met Lys Leu Val Phe Gly Thr Leu Leu Cys Ser Leu Leu Leu Leu Ser
 1               5                  10                 15

Phe Ser Phe Leu Glu Pro Val Ile Ala Tyr Glu Asp Ser Ser Tyr Cys
                20                 25                 30

Ser Asn Lys Cys Ala Asp Arg Cys Ser Ser Ala Gly Val Lys Asp Arg
                35                 40                 45

Cys Val Lys Tyr Cys Gly Ile Cys Cys Ala Glu Cys Lys Cys Val Pro
                50                 55                 60

Ser Gly Thr Tyr Gly Asn Lys His Glu Cys Pro Cys Tyr Arg Asp Lys
 65                 70                 75                 80

Leu Asn Lys Lys Gly Lys Pro Lys Cys Pro
                85                 90
```

<210> SEQ ID NO 60
<211> LENGTH: 96
<212> TYPE: PRT
<213> ORGANISM: Glycine max

<400> SEQUENCE: 60

```
Met Ala Ile Ser Lys Ser Thr Val Val Val Ile Leu Cys Phe Ile
 1               5                  10                 15
```

Leu Ile Gln Glu Leu Gly Ile Tyr Gly Glu Asp Pro His Met Asp Ala
            20                  25                  30

Ala Lys Lys Ile Asp Cys Gly Gly Lys Cys Asn Ser Arg Cys Ser Lys
        35                  40                  45

Ala Arg Arg Gln Lys Met Cys Ile Arg Ala Cys Asn Ser Cys Cys Lys
    50                  55                  60

Lys Cys Arg Cys Val Pro Pro Gly Thr Ser Gly Asn Arg Asp Leu Cys
65                  70                  75                  80

Pro Cys Tyr Ala Arg Leu Thr Thr His Gly Gly Lys Leu Lys Cys Pro
                85                  90                  95

<210> SEQ ID NO 61
<211> LENGTH: 108
<212> TYPE: PRT
<213> ORGANISM: Glycine max

<400> SEQUENCE: 61

Met Met Gly Ile Leu Leu Val Cys Leu Ala Lys Val Ser Ser Asp
1               5                   10                  15

Val Asn Met Gln Lys Glu Glu Asp Glu Leu Arg Phe Pro Asn His
            20                  25                  30

Pro Leu Ile Val Arg Asp Gly Asn Arg Arg Leu Met Gln Asp Ile Asp
        35                  40                  45

Cys Gly Gly Leu Cys Lys Thr Arg Cys Ser Ala His Ser Arg Pro Asn
    50                  55                  60

Val Cys Asn Arg Ala Cys Gly Thr Cys Cys Val Arg Cys Lys Cys Val
65                  70                  75                  80

Pro Pro Gly Thr Ser Gly Asn Arg Glu Leu Cys Gly Thr Cys Tyr Thr
                85                  90                  95

Asp Met Ile Thr His Gly Asn Lys Thr Lys Cys Pro
                100                 105

<210> SEQ ID NO 62
<211> LENGTH: 117
<212> TYPE: PRT
<213> ORGANISM: Glycine max

<400> SEQUENCE: 62

Met Ala Pro Arg Val Phe Leu Val Leu Gly Met Leu Met Val Cys
1               5                   10                  15

Leu Val Lys Val Ser Ser Asp Pro Lys Arg Glu Glu Ile Leu Glu
            20                  25                  30

Glu Leu His Phe Pro Asp Asn Glu Pro Leu Ile Val Arg Asp Gly
        35                  40                  45

Asn Arg Arg Leu Met Gln Asp Ile Asp Cys Gly Gly Leu Cys Lys Thr
    50                  55                  60

Arg Cys Ser Ala His Ser Arg Pro Asn Leu Cys Thr Arg Ala Cys Gly
65                  70                  75                  80

Thr Cys Cys Val Arg Cys Lys Cys Val Pro Pro Gly Thr Ser Gly Asn
                85                  90                  95

Arg Glu Leu Cys Gly Thr Cys Tyr Thr Asp Met Thr Thr His Gly Asn
                100                 105                 110

Lys Thr Lys Cys Pro
        115

<210> SEQ ID NO 63

```
<211> LENGTH: 119
<212> TYPE: PRT
<213> ORGANISM: Glycine max

<400> SEQUENCE: 63

Met Ala Leu Arg Val Leu Leu Val Leu Gly Met Leu Leu Met Leu Cys
1               5                   10                  15

Leu Val Lys Val Ser Ser Asp Pro Lys Ile Glu Glu Ile Leu Glu
            20                  25                  30

Ala Glu Glu Glu Leu Gln Phe Pro Asp Asn Glu Pro Leu Ile Val Arg
            35                  40                  45

Asp Ala Asn Arg Arg Leu Met Gln Asp Met Asp Cys Gly Gly Leu Cys
        50                  55                  60

Lys Thr Arg Cys Ser Ala His Ser Arg Pro Asn Leu Cys Thr Arg Ala
65                  70                  75                  80

Cys Gly Thr Cys Val Arg Cys Lys Cys Val Pro Pro Gly Thr Ser
                85                  90                  95

Gly Asn Arg Glu Leu Cys Gly Thr Cys Tyr Thr Asp Met Thr Thr His
                100                 105                 110

Gly Asn Lys Thr Lys Cys Pro
            115

<210> SEQ ID NO 64
<211> LENGTH: 99
<212> TYPE: PRT
<213> ORGANISM: Glycine max

<400> SEQUENCE: 64

Met Ala Leu Ser Lys Leu Ile Ile Ala Ser Leu Leu Ala Ser Leu Leu
1               5                   10                  15

Leu Leu His Phe Val Asp Ala Asp Gln Ser Ala His Ala Gln Thr Gln
            20                  25                  30

Gly Ser Leu Leu Gln Gln Ile Asp Cys Asn Gly Ala Cys Ala Ala Arg
            35                  40                  45

Cys Arg Leu Ser Ser Arg Pro Arg Leu Cys Gln Arg Ala Cys Gly Thr
        50                  55                  60

Cys Cys Arg Arg Cys Asn Cys Val Pro Pro Gly Thr Ala Gly Asn Gln
65                  70                  75                  80

Glu Val Cys Pro Cys Tyr Ala Ser Leu Thr Thr His Gly Gly Lys Arg
                85                  90                  95

Lys Cys Pro

<210> SEQ ID NO 65
<211> LENGTH: 115
<212> TYPE: PRT
<213> ORGANISM: Glycine max

<400> SEQUENCE: 65

Met Glu Lys Lys Arg Lys Thr Leu Leu Leu Leu Leu Met Ala Ala
1               5                   10                  15

Thr Leu Phe Cys Met Pro Ile Val Ser Tyr Ala Val Ser Ser Val Asn
            20                  25                  30

Ile Gln Gly His Leu Thr His Ser Glu Leu Val Lys Gly Pro Asn Arg
            35                  40                  45

Arg Leu Leu Pro Phe Val Asp Cys Gly Ala Arg Cys Arg Val Arg Cys
        50                  55                  60

Ser Leu His Ser Arg Pro Lys Ile Cys Ser Arg Ala Cys Gly Thr Cys
```

```
                65                  70                  75                  80
Cys Phe Arg Cys Arg Cys Val Pro Pro Gly Thr Tyr Gly Asn Arg Glu
                    85                  90                  95

Met Cys Gly Lys Cys Tyr Thr Asp Met Ile Thr His Gly Asn Lys Pro
                100                 105                 110

Lys Cys Pro
        115

<210> SEQ ID NO 66
<211> LENGTH: 191
<212> TYPE: PRT
<213> ORGANISM: Glycine max
<220> FEATURE:
<221> NAME/KEY: VARIANT
<222> LOCATION: (1)...(48)
<223> OTHER INFORMATION: Xaa = Any Amino Acid

<400> SEQUENCE: 66

Met Ala Ser Asn Ser Ile Leu Leu Cys Ile Phe Leu Val Val Ala
 1               5                  10                  15

Thr Lys Val Phe Ser Tyr Asp Glu Asp Leu Lys Thr Val Val Pro Ala
                20                  25                  30

Pro Ala Pro Pro Val Lys Ala Pro Thr Leu Ala Pro Pro Val Lys Ser
                35                  40                  45

Pro Ser Tyr Pro Pro Gly Pro Val Thr Thr Pro Thr Val Pro Thr Pro
        50                  55                  60

Thr Val Lys Val Pro Pro Pro Gln Ser Pro Val Val Lys Pro Pro
65                  70                  75                  80

Thr Pro Thr Val Pro Pro Thr Val Lys Val Pro Pro Pro Gln
                85                  90                  95

Ser Pro Val Val Lys Pro Pro Thr Pro Thr Pro Thr Ser Pro Val Val
                100                 105                 110

Tyr Pro Pro Pro Val Ala Pro Ser Pro Pro Ala Pro Val Val Lys Ser
                115                 120                 125

Asn Lys Asp Cys Ile Pro Leu Cys Asp Tyr Arg Cys Ser Leu His Ser
        130                 135                 140

Arg Lys Lys Leu Cys Met Arg Ala Cys Ile Thr Cys Cys Asp Arg Cys
145                 150                 155                 160

Lys Cys Val Pro Pro Gly Thr Tyr Gly Asn Arg Glu Lys Cys Gly Lys
                165                 170                 175

Cys Tyr Thr Asp Met Leu Thr His Gly Asn Lys Phe Lys Cys Pro
                180                 185                 190

<210> SEQ ID NO 67
<211> LENGTH: 107
<212> TYPE: PRT
<213> ORGANISM: Glycine max

<400> SEQUENCE: 67

Met Ala Lys Phe Phe Ala Ala Met Ile Leu Ala Leu Phe Ala Ile Ser
 1               5                  10                  15

Ile Leu Gln Thr Val Val Met Ala Ala Asn Glu Gln Gly Gly His Leu
                20                  25                  30

Tyr Asp Asn Lys Ser Lys Tyr Gly Ser Gly Ser Val Lys Ser Tyr Gln
                35                  40                  45

Cys Pro Ser Gln Cys Ser Arg Arg Cys Ser Gln Thr Gln Tyr His Lys
        50                  55                  60
```

```
Pro Cys Met Phe Phe Cys Gln Lys Cys Cys Arg Thr Cys Leu Cys Val
65                  70                  75                  80

Pro Pro Gly Tyr Tyr Gly Asn Lys Ala Val Cys Pro Cys Tyr Asn Asn
                85                  90                  95

Trp Lys Thr Lys Glu Gly Gly Pro Lys Cys Pro
            100                 105
```

<210> SEQ ID NO 68
<211> LENGTH: 107
<212> TYPE: PRT
<213> ORGANISM: Glycine max

<400> SEQUENCE: 68

```
Met Ala Lys Phe Phe Ala Ala Met Ile Leu Ala Leu Ile Ala Ile Ser
1               5                   10                  15

Met Leu Gln Thr Val Val Met Ala Ala Asn Glu Gln Gly Gly His Leu
                20                  25                  30

Tyr Asp Asn Lys Ser Lys Tyr Gly Ser Gly Ser Val Lys Arg Tyr Gln
            35                  40                  45

Cys Pro Ser Gln Cys Ser Arg Arg Cys Ser Gln Thr Gln Tyr His Lys
        50                  55                  60

Pro Cys Met Phe Phe Cys Gln Lys Cys Cys Arg Lys Cys Leu Cys Val
65                  70                  75                  80

Pro Pro Gly Tyr Tyr Gly Asn Lys Ala Val Cys Pro Cys Tyr Asn Asn
                85                  90                  95

Trp Lys Thr Lys Glu Gly Gly Pro Lys Cys Pro
            100                 105
```

<210> SEQ ID NO 69
<211> LENGTH: 110
<212> TYPE: PRT
<213> ORGANISM: Glycine max

<400> SEQUENCE: 69

```
Met Ala Val Ala Asn Lys Leu Leu Ser Val Leu Ile Ile Ala Leu Ile
1               5                   10                  15

Ala Ile Ser Met Leu Gln Thr Val Val Met Ala Ser His Gly His Gly
                20                  25                  30

Gly His His Tyr Asn Asp Lys Lys Lys Tyr Gly Pro Gly Ser Leu Lys
            35                  40                  45

Ser Phe Gln Cys Pro Ser Gln Cys Ser Arg Arg Cys Gly Lys Thr Gln
        50                  55                  60

Tyr His Lys Pro Cys Met Phe Phe Cys Gln Lys Cys Cys Arg Lys Cys
65                  70                  75                  80

Leu Cys Val Pro Pro Gly Tyr Tyr Gly Asn Lys Ala Val Cys Pro Cys
                85                  90                  95

Tyr Asn Asn Trp Lys Thr Lys Glu Gly Gly Pro Lys Cys Pro
            100                 105                 110
```

<210> SEQ ID NO 70
<211> LENGTH: 106
<212> TYPE: PRT
<213> ORGANISM: Glycine max

<400> SEQUENCE: 70

```
Met Ala Met Ala Lys Val Phe Cys Val Leu Leu Leu Ala Leu Leu Gly
1               5                   10                  15

Ile Ser Met Ile Thr Thr Gln Val Met Ala Thr Asp Ser Ala Tyr His
```

-continued

```
                 20                   25                  30
Leu Asp Gly Arg Asn Tyr Gly Pro Gly Ser Leu Lys Ser Gln Cys
         35                  40                  45

Pro Ser Glu Cys Thr Arg Arg Cys Ser Gln Thr Gln Tyr His Lys Pro
     50                  55                  60

Cys Met Val Phe Cys Lys Gln Cys Cys Lys Arg Cys Leu Cys Val Pro
 65                  70                  75                  80

Pro Gly Tyr Tyr Gly Asn Lys Ser Val Cys Pro Cys Tyr Asn Asn Trp
                 85                  90                  95

Lys Thr Lys Arg Gly Gly Pro Lys Cys Pro
             100                 105
```

<210> SEQ ID NO 71
<211> LENGTH: 123
<212> TYPE: PRT
<213> ORGANISM: Glycine max

<400> SEQUENCE: 71

```
Met Leu Leu Leu Leu Val Glu Asn His Ala Glu Ile Val Val Ser Thr
 1               5                  10                  15

Val Glu Ala Ser Ala Pro Gln Pro His Lys Asn Thr Thr His Thr Leu
                 20                  25                  30

Ser His Ala Pro Ala Pro Gln Pro His Lys Asn Thr Lys Ser Pro Val
             35                  40                  45

Pro Asn Leu Gln His Gly Ile Thr Glu Gly Ser Leu Lys Pro Gln Glu
         50                  55                  60

Cys Gly Pro Arg Cys Thr Ala Arg Cys Ser Asn Thr Gln Tyr Lys Lys
 65                  70                  75                  80

Pro Cys Leu Phe Phe Cys Gln Lys Cys Cys Ala Lys Cys Leu Cys Val
                 85                  90                  95

Pro Pro Gly Thr Tyr Gly Asn Lys Gln Val Cys Pro Cys Tyr Asn Asn
             100                 105                 110

Trp Lys Thr Lys Arg Gly Gly Pro Lys Cys Pro
         115                 120
```

<210> SEQ ID NO 72
<211> LENGTH: 97
<212> TYPE: PRT
<213> ORGANISM: Glycine max

<400> SEQUENCE: 72

```
Met Ala Ala Arg Ser Tyr Ser Pro Ile Met Val Ala Leu Ser Leu Leu
 1               5                  10                  15

Leu Leu Val Thr Phe Ser Asn Val Ala Glu Ala Tyr Thr Arg Ser Gly
                 20                  25                  30

Thr Leu Arg Pro Ser Asp Cys Lys Pro Lys Cys Thr Tyr Arg Cys Ser
             35                  40                  45

Ala Thr Ser His Lys Lys Pro Cys Met Phe Phe Cys Gln Lys Cys Cys
         50                  55                  60

Ala Lys Cys Leu Cys Val Pro Pro Gly Thr Tyr Gly Asn Lys Gln Ile
 65                  70                  75                  80

Cys Pro Cys Tyr Asn Ser Trp Lys Thr Lys Glu Gly Gly Pro Lys Cys
                 85                  90                  95

Pro
```

<210> SEQ ID NO 73

```
<211> LENGTH: 66
<212> TYPE: PRT
<213> ORGANISM: Oryza sativa

<400> SEQUENCE: 73

His Glu Val Gln His Ile Asp Cys Asn Ala Ala Cys Ala Ala Arg Cys
1               5                   10                  15

Arg Leu Ala Ser Arg Gln Arg Met Cys His Arg Ala Cys Gly Thr Cys
            20                  25                  30

Cys Arg Arg Cys Asn Cys Val Pro Pro Gly Thr Ser Gly Asn Gln Glu
        35                  40                  45

Val Cys Pro Cys Tyr Ala Ser Leu Ala Thr His Gly Gly Arg Arg Lys
    50                  55                  60

Cys Pro
65

<210> SEQ ID NO 74
<211> LENGTH: 88
<212> TYPE: PRT
<213> ORGANISM: Solanum tuberosum

<400> SEQUENCE: 74

Met Lys Leu Phe Leu Leu Thr Leu Leu Leu Val Thr Leu Val Ile Thr
1               5                   10                  15

Pro Ser Leu Ile Gln Thr Thr Met Ala Gly Ser Asn Phe Cys Asp Ser
            20                  25                  30

Lys Cys Lys Leu Arg Cys Ser Lys Ala Gly Leu Ala Asp Arg Cys Leu
        35                  40                  45

Lys Tyr Cys Gly Val Cys Cys Glu Glu Cys Lys Cys Val Pro Ser Gly
    50                  55                  60

Thr Tyr Gly Asn Lys His Glu Cys Pro Cys Tyr Arg Asp Lys Lys Asn
65                  70                  75                  80

Ser Lys Gly Lys Ser Lys Cys Pro
                85

<210> SEQ ID NO 75
<211> LENGTH: 63
<212> TYPE: PRT
<213> ORGANISM: Gerbera hybrida

<400> SEQUENCE: 75

Ser Lys Ile Asn Cys Gly Ala Ala Cys Lys Ala Arg Cys Arg Leu Ser
1               5                   10                  15

Ser Arg Pro Asn Leu Cys His Arg Ala Cys Gly Thr Cys Cys Ala Arg
            20                  25                  30

Cys Arg Cys Val Pro Pro Gly Thr Ser Gly Asn Gln Lys Val Cys Pro
        35                  40                  45

Cys Tyr Tyr Asn Met Thr Thr His Gly Gly Arg Arg Lys Cys Pro
    50                  55                  60

<210> SEQ ID NO 76
<211> LENGTH: 63
<212> TYPE: PRT
<213> ORGANISM: Arabidopsis thaliana

<400> SEQUENCE: 76

Lys Ser Tyr Gln Cys Gly Gly Gln Cys Thr Arg Arg Cys Ser Asn Thr
1               5                   10                  15

Lys Tyr His Lys Pro Cys Met Phe Phe Cys Gln Lys Cys Cys Ala Lys
```

-continued

```
                 20                  25                  30
Cys Leu Cys Val Pro Gly Thr Tyr Gly Asn Lys Gln Val Cys Pro
             35                  40                  45
Cys Tyr Asn Asn Trp Lys Thr Gln Gln Gly Gly Pro Lys Cys Pro
 50                  55                  60

<210> SEQ ID NO 77
<211> LENGTH: 96
<212> TYPE: PRT
<213> ORGANISM: Solanum lycopersicum

<400> SEQUENCE: 77

Met Ala Lys Ser Gly Tyr Asn Ala Ser Phe Leu Leu Ile Ser Met
 1               5                  10                  15

Phe Leu Ile Leu Thr Phe Ser Asn Val Val Glu Gly Tyr Asn Lys
             20                  25                  30

Leu Arg Pro Thr Asp Cys Lys Pro Arg Cys Thr Tyr Arg Cys Ser Ala
             35                  40                  45

Thr Ser His Lys Lys Pro Cys Met Phe Phe Cys Gln Lys Cys Ala
 50                  55                  60

Thr Cys Leu Cys Val Pro Lys Gly Val Tyr Gly Asn Lys Gln Ser Cys
 65                  70                  75                  80

Pro Cys Tyr Asn Asn Trp Lys Thr Gln Glu Gly Lys Pro Lys Cys Pro
             85                  90                  95

<210> SEQ ID NO 78
<211> LENGTH: 106
<212> TYPE: PRT
<213> ORGANISM: Arabidopsis thaliana

<400> SEQUENCE: 78

Met Ala Lys Ser Tyr Gly Ala Ile Phe Leu Leu Thr Leu Ile Val Leu
 1               5                  10                  15

Phe Met Leu Gln Thr Met Val Met Ala Ser Ser Gly Ser Asn Val Lys
             20                  25                  30

Trp Ser Gln Lys Arg Tyr Gly Pro Gly Ser Leu Lys Arg Thr Gln Cys
             35                  40                  45

Pro Ser Glu Cys Asp Arg Arg Cys Lys Lys Thr Gln Tyr His Lys Ala
 50                  55                  60

Cys Ile Thr Phe Cys Asn Lys Cys Cys Arg Lys Cys Leu Cys Val Pro
 65                  70                  75                  80

Pro Gly Tyr Tyr Gly Asn Lys Gln Val Cys Ser Cys Tyr Asn Asn Trp
             85                  90                  95

Lys Thr Gln Glu Gly Gly Pro Lys Cys Pro
            100                 105

<210> SEQ ID NO 79
<211> LENGTH: 106
<212> TYPE: PRT
<213> ORGANISM: Arabidopsis thaliana

<400> SEQUENCE: 79

Met Ala Lys Ser Tyr Gly Ala Ile Phe Leu Leu Thr Leu Ile Val Leu
 1               5                  10                  15

Phe Met Leu Gln Thr Met Val Met Ala Ser Ser Gly Ser Asn Val Lys
             20                  25                  30

Trp Arg Gln Lys Arg Tyr Gly Pro Gly Ser Leu Lys Arg Thr Gln Cys
             35                  40                  45
```

```
Pro Ser Glu Cys Asp Arg Arg Cys Lys Lys Thr Gln Tyr His Lys Ala
    50                  55                  60

Cys Ile Thr Phe Cys Asn Lys Cys Arg Lys Cys Leu Cys Val Pro
 65                  70                  75                  80

Pro Gly Tyr Tyr Gly Asn Lys Gln Val Cys Ser Cys Tyr Asn Asn Trp
                 85                  90                  95

Lys Thr Gln Glu Gly Gly Pro Lys Cys Pro
            100                 105
```

<210> SEQ ID NO 80
<211> LENGTH: 97
<212> TYPE: PRT
<213> ORGANISM: Arabidopsis thaliana

<400> SEQUENCE: 80

```
Met Ala Asn Cys Ile Arg Arg Asn Ala Leu Phe Phe Leu Thr Leu Leu
  1               5                  10                  15

Phe Leu Leu Ser Val Ser Asn Leu Val Gln Ala Ala Arg Gly Gly Gly
                 20                  25                  30

Lys Leu Lys Pro Gln Gln Cys Asn Ser Lys Cys Ser Tyr Arg Cys Ser
             35                  40                  45

Ala Thr Ser His Lys Lys Pro Cys Met Phe Cys Leu Lys Cys Cys
     50                  55                  60

Lys Lys Cys Leu Cys Val Pro Pro Gly Thr Phe Gly Asn Lys Gln Thr
 65                  70                  75                  80

Cys Pro Cys Tyr Asn Asn Trp Lys Thr Lys Glu Gly Arg Pro Lys Cys
                 85                  90                  95

Pro
```

<210> SEQ ID NO 81
<211> LENGTH: 112
<212> TYPE: PRT
<213> ORGANISM: Lycopersicon esculentum

<400> SEQUENCE: 81

```
Met Ala Gly Lys Met Ser Ile Val Leu Phe Val Leu Val Val Phe
  1               5                  10                  15

Leu Thr Gln Asn Gln Val Ser Arg Ala Asn Ile Met Arg Asp Glu Gln
                 20                  25                  30

Gln Gln Gln Gln Arg Asn Asn Gln Leu Tyr Gly Val Ser Glu Gly Arg
             35                  40                  45

Leu His Pro Gln Asp Cys Gln Pro Lys Cys Thr Tyr Arg Cys Ser Lys
 50                  55                  60

Thr Ser Tyr Lys Lys Pro Cys Met Phe Phe Cys Gln Lys Cys Cys Ala
 65                  70                  75                  80

Lys Cys Leu Cys Val Pro Ala Gly Thr Tyr Gly Asn Lys Gln Ser Cys
                 85                  90                  95

Pro Cys Tyr Asn Asn Trp Lys Thr Lys Arg Gly Gly Pro Lys Cys Pro
            100                 105                 110
```

<210> SEQ ID NO 82
<211> LENGTH: 99
<212> TYPE: PRT
<213> ORGANISM: Arabidopsis thaliana

<400> SEQUENCE: 82

```
Met Ala Ile Phe Arg Ser Thr Leu Val Leu Leu Leu Ile Leu Phe Cys
```

```
                 1               5                  10                 15
Leu Thr Thr Phe Glu Leu His Val His Ala Ala Glu Asp Ser Gln Val
                20                  25                 30

Gly Glu Gly Val Val Lys Ile Asp Cys Gly Gly Arg Cys Lys Gly Arg
            35                  40                  45

Cys Ser Lys Ser Ser Arg Pro Asn Leu Cys Leu Arg Ala Cys Asn Ser
            50                  55                  60

Cys Cys Tyr Arg Cys Asn Cys Val Pro Pro Gly Thr Ala Gly Asn His
 65                 70                  75                  80

His Leu Cys Pro Cys Tyr Ala Ser Ile Thr Thr Arg Gly Gly Arg Leu
                85                  90                  95

Lys Cys Pro

<210> SEQ ID NO 83
<211> LENGTH: 99
<212> TYPE: PRT
<213> ORGANISM: Arabidopsis thaliana

<400> SEQUENCE: 83

Met Ala Val Phe Arg Ser Thr Leu Val Leu Leu Ile Ile Val Cys
 1               5                  10                 15

Leu Thr Thr Tyr Glu Leu His Val His Ala Ala Asp Gly Ala Lys Val
                20                  25                 30

Gly Glu Gly Val Val Lys Ile Asp Cys Gly Gly Arg Cys Lys Asp Arg
            35                  40                  45

Cys Ser Lys Ser Ser Arg Thr Lys Leu Cys Leu Arg Ala Cys Asn Ser
            50                  55                  60

Cys Cys Ser Arg Cys Asn Cys Val Pro Pro Gly Thr Ser Gly Asn Thr
 65                 70                  75                  80

His Leu Cys Pro Cys Tyr Ala Ser Ile Thr Thr His Gly Gly Arg Leu
                85                  90                  95

Lys Cys Pro

<210> SEQ ID NO 84
<211> LENGTH: 98
<212> TYPE: PRT
<213> ORGANISM: Arabidopsis thaliana

<400> SEQUENCE: 84

Met Ala Ile Ser Lys Ala Leu Ile Ala Ser Leu Leu Ile Ser Leu Leu
 1               5                  10                 15

Val Leu Gln Leu Val Gln Ala Asp Val Glu Ser Ser Gln Lys Lys Asn
                20                  25                 30

Gly Tyr Ala Lys Lys Ile Asp Cys Gly Ser Ala Cys Val Ala Arg Cys
            35                  40                  45

Arg Leu Ser Arg Arg Pro Arg Leu Cys His Arg Ala Cys Gly Thr Cys
            50                  55                  60

Cys Tyr Arg Cys Asn Cys Val Pro Pro Gly Thr Tyr Gly Asn Tyr Asp
 65                 70                  75                  80

Lys Cys Gln Cys Tyr Ala Ser Leu Thr Thr His Gly Gly Arg Arg Lys
                85                  90                  95

Cys Pro

<210> SEQ ID NO 85
<211> LENGTH: 112
<212> TYPE: PRT
```

<213> ORGANISM: Petunia x hybrida

<400> SEQUENCE: 85

```
Met Ala Gly Lys Leu Ser Ile Val Leu Phe Val Leu Val Val Leu
1               5                   10                  15

Leu Ala Gln Asn Gln Val Ser Arg Ala Lys Met Val Leu Asp Ser Lys
            20                  25                  30

Val Gln Arg Arg Gly Asn Asp Gln Ile Tyr Gly Val Ser Gln Gly Ser
        35                  40                  45

Leu His Pro Gln Asp Cys Gln Pro Lys Cys Thr Tyr Arg Cys Ser Lys
    50                  55                  60

Thr Ser Phe Lys Lys Pro Cys Met Phe Phe Cys Gln Lys Cys Cys Ala
65                  70                  75                  80

Lys Cys Leu Cys Val Pro Ala Gly Thr Tyr Gly Asn Lys Gln Thr Cys
                85                  90                  95

Pro Cys Tyr Asn Asn Trp Lys Thr Lys Glu Gly Pro Lys Cys Pro
            100                 105                 110
```

<210> SEQ ID NO 86
<211> LENGTH: 102
<212> TYPE: PRT
<213> ORGANISM: Lavatera thuringiaca

<400> SEQUENCE: 86

```
Met Ala Ile Ser Lys Ala Leu Ile Ala Ser Leu Leu Ile Ser Leu Leu
1               5                   10                  15

Ile Ile Gln Ile Val Glu Ala Asp His Gln Leu Val Thr Ser Ala Gly
            20                  25                  30

Lys Gly Asn Ser Ser Pro Lys Lys Ile Asp Cys Gly Gly Ala Cys Ala
        35                  40                  45

Ala Arg Cys Gln Leu Ser Ser Arg Pro His Leu Cys Lys Arg Ala Cys
    50                  55                  60

Gly Thr Cys Cys Ala Arg Cys Ala Cys Val Pro Pro Gly Thr Ala Gly
65                  70                  75                  80

Asn Gln Glu Met Cys Pro Lys Cys Tyr Ala Ser Leu Thr Thr His Gly
                85                  90                  95

Gly Lys Arg Lys Cys Pro
            100
```

<210> SEQ ID NO 87
<211> LENGTH: 91
<212> TYPE: PRT
<213> ORGANISM: Fragaria x ananassa

<400> SEQUENCE: 87

```
Met Met Met Ile Ser Leu Leu Val Phe Asn Pro Val Glu Ala Asp Gly
1               5                   10                  15

Val Val Val Asn Tyr Gly Gln His Ala Ser Leu Leu Ala Lys Ile Asp
            20                  25                  30

Cys Gly Gly Ala Cys Lys Ala Arg Cys Arg Leu Ser Ser Arg Pro His
        35                  40                  45

Leu Cys Lys Arg Ala Cys Gly Thr Cys Cys Gln Arg Cys Ser Cys Val
    50                  55                  60

Pro Pro Gly Thr Ala Gly Asn Tyr Asp Val Cys Pro Cys Tyr Ala Thr
65                  70                  75                  80

Leu Thr Thr His Gly Gly Lys Arg Lys Cys Pro
                85                  90
```

<210> SEQ ID NO 88
<211> LENGTH: 101
<212> TYPE: PRT
<213> ORGANISM: Lavatera thuringiaca

<400> SEQUENCE: 88

Met Ala Ile Ser Lys Ala Leu Ile Ala Ser Leu Leu Ile Ser Leu Leu
1               5                   10                  15

Ile Ile Gln Ile Val Glu Ala Asp His Gln Leu Val Thr Ser Ala Ser
            20                  25                  30

Lys Gly Ser Ser Phe Pro Lys Ile Asp Cys Gly Ala Cys Ala
        35                  40                  45

Ala Arg Cys Gln Leu Ser Ser Arg Pro His Leu Cys Lys Arg Ala Cys
    50                  55                  60

Gly Thr Cys Cys Ala Arg Ser Arg Cys Val Pro Pro Gly Thr Ala Gly
65                  70                  75                  80

Asn Gln Glu Met Cys Pro Cys Tyr Ala Ser Leu Thr Thr His Gly Gly
                85                  90                  95

Lys Arg Lys Cys Pro
            100

<210> SEQ ID NO 89
<211> LENGTH: 103
<212> TYPE: PRT
<213> ORGANISM: Arabidopsis thaliana

<400> SEQUENCE: 89

Met Ile Tyr Glu Phe Arg Glu Ile Lys Phe Phe Leu Cys Val Tyr
1               5                   10                  15

Val Gln Gly Asp Glu Leu Glu Ser Gln Ala Gln Ala Pro Ala Ile His
            20                  25                  30

Lys Asn Gly Gly Glu Gly Ser Leu Lys Pro Glu Cys Pro Lys Ala
        35                  40                  45

Cys Glu Tyr Arg Cys Ser Ala Thr Ser His Arg Lys Pro Cys Leu Phe
    50                  55                  60

Phe Cys Asn Lys Cys Cys Asn Lys Cys Leu Cys Val Pro Ser Gly Thr
65                  70                  75                  80

Tyr Gly His Lys Glu Glu Cys Pro Cys Tyr Asn Asn Trp Thr Thr Lys
                85                  90                  95

Glu Gly Gly Pro Lys Cys Pro
            100

<210> SEQ ID NO 90
<211> LENGTH: 87
<212> TYPE: PRT
<213> ORGANISM: Arabidopsis thaliana

<400> SEQUENCE: 90

Met Lys Leu Val Val Val Gln Phe Phe Ile Ile Ser Leu Leu Leu Thr
1               5                   10                  15

Ser Ser Phe Ser Val Leu Ser Ser Ala Asp Ser Ser Cys Gly Gly Lys
            20                  25                  30

Cys Asn Val Arg Cys Ser Lys Ala Gly Gln His Glu Gly Cys Leu Lys
        35                  40                  45

Tyr Cys Asn Ile Cys Cys Gln Lys Cys Asn Cys Val Pro Ser Gly Thr
    50                  55                  60

```
Phe Gly His Lys Asp Glu Cys Pro Cys Tyr Arg Asp Met Lys Asn Ser
 65                  70                  75                  80

Lys Gly Gly Ser Lys Cys Pro
                85

<210> SEQ ID NO 91
<211> LENGTH: 110
<212> TYPE: PRT
<213> ORGANISM: Picea mariana

<400> SEQUENCE: 91

Met Ala Arg Leu Gln Ser Phe Ala Val Leu Leu Ile Thr Ile Phe Ala
  1               5                  10                  15

Leu Phe Ile Trp Asn Ile Glu Ala Ala Leu Pro His Ser Asn Val Asp
                 20                  25                  30

Pro Phe Met Glu Gln Lys Gln Gly Gln Tyr Gly Glu Gly Ser Leu Arg
             35                  40                  45

Pro Ser Glu Cys Gly Gln Arg Cys Ser Tyr Arg Cys Ser Ala Thr Ser
         50                  55                  60

His Lys Lys Pro Cys Met Phe Phe Cys Gln Lys Cys Ala Lys Cys
 65                  70                  75                  80

Leu Cys Val Pro Pro Gly Thr Phe Gly Asn Lys Gln Val Cys Pro Cys
                 85                  90                  95

Tyr Asn Asn Trp Lys Thr Gln Gln Gly Gly Pro Lys Cys Pro
            100                 105                 110

<210> SEQ ID NO 92
<211> LENGTH: 108
<212> TYPE: PRT
<213> ORGANISM: Arabidopsis thaliana

<400> SEQUENCE: 92

Met Lys Ile Ile Val Ser Ile Leu Val Leu Ala Ser Leu Leu Leu Ile
  1               5                  10                  15

Ser Ser Ser Leu Ala Ser Ala Thr Ile Ser Asp Ala Phe Gly Ser Gly
                 20                  25                  30

Ala Val Ala Pro Ala Pro Gln Ser Lys Asp Gly Pro Ala Leu Glu Lys
             35                  40                  45

Trp Cys Gly Gln Lys Cys Glu Gly Arg Cys Lys Glu Ala Gly Met Lys
         50                  55                  60

Asp Arg Cys Leu Lys Tyr Cys Gly Ile Cys Cys Lys Asp Cys Gln Cys
 65                  70                  75                  80

Val Pro Ser Gly Thr Tyr Gly Asn Lys His Glu Cys Ala Cys Tyr Arg
                 85                  90                  95

Asp Lys Leu Ser Ser Lys Gly Thr Pro Lys Cys Pro
            100                 105

<210> SEQ ID NO 93
<211> LENGTH: 88
<212> TYPE: PRT
<213> ORGANISM: Arabidopsis thaliana

<400> SEQUENCE: 93

Met Ala Val Phe Arg Val Leu Leu Ala Ser Leu Leu Ile Ser Leu Leu
  1               5                  10                  15

Val Leu Asp Phe Val His Ala Asp Met Val Arg Cys Ser Leu Ser Ser
                 20                  25                  30

Arg Pro Asn Leu Cys His Arg Ala Cys Gly Thr Cys Cys Ala Arg Cys
```

```
                35                  40                  45
Asn Cys Val Ala Pro Gly Thr Ser Gly Asn Tyr Asp Lys Cys Pro Cys
             50                  55                  60

Tyr Gly Ser Leu Thr Thr His Gly Gly Arg Arg Lys Glu Val Lys Glu
 65                  70                  75                  80

Phe Ser Phe Phe Thr His Gly Ser
                 85

<210> SEQ ID NO 94
<211> LENGTH: 98
<212> TYPE: PRT
<213> ORGANISM: Arabidopsis thaliana

<400> SEQUENCE: 94

Met Ala Ile Ser Lys Ala Leu Ile Ala Ser Leu Leu Ile Ser Leu Leu
  1               5                  10                  15

Val Leu Gln Leu Val Gln Ala Asp Val Glu Asn Ser Gln Lys Lys Asn
                 20                  25                  30

Gly Tyr Ala Lys Lys Ile Asp Cys Gly Ser Ala Cys Val Ala Arg Cys
                 35                  40                  45

Arg Leu Ser Arg Arg Pro Arg Leu Cys His Arg Ala Cys Gly Thr Cys
             50                  55                  60

Cys Tyr Arg Cys Asn Cys Val Pro Pro Gly Thr Tyr Gly Asn Tyr Asp
 65                  70                  75                  80

Lys Cys Gln Cys Tyr Ala Ser Leu Thr Thr His Gly Gly Arg Arg Lys
                 85                  90                  95

Cys Pro

<210> SEQ ID NO 95
<211> LENGTH: 93
<212> TYPE: PRT
<213> ORGANISM: Oryza sativa

<400> SEQUENCE: 95

Met Lys Leu Asn Thr Thr Thr Thr Leu Ala Leu Leu Leu Leu Leu Leu
  1               5                  10                  15

Leu Ala Ser Ser Ser Leu Gln Val Ser Met Ala Gly Ser Asp Phe Cys
                 20                  25                  30

Asp Gly Lys Cys Lys Val Arg Cys Ser Lys Ala Ser Arg His Asp Asp
                 35                  40                  45

Cys Leu Lys Tyr Cys Gly Val Cys Cys Ala Ser Cys Asn Cys Val Pro
             50                  55                  60

Ser Gly Thr Ala Gly Asn Lys Asp Glu Cys Pro Cys Tyr Arg Asp Met
 65                  70                  75                  80

Thr Thr Gly His Gly Ala Arg Lys Arg Pro Lys Cys Pro
                 85                  90

<210> SEQ ID NO 96
<211> LENGTH: 106
<212> TYPE: PRT
<213> ORGANISM: Arabidopsis thaliana

<400> SEQUENCE: 96

Met Ala Lys Ser Tyr Gly Ala Ile Phe Leu Leu Thr Leu Ile Val Leu
  1               5                  10                  15

Phe Met Leu Gln Thr Met Tyr Met Ala Ser Ser Gly Ser Asn Val Lys
                 20                  25                  30
```

-continued

```
Trp Arg Gln Lys Arg Val Gly Pro Gly Ser Leu Lys Arg Thr Gln Cys
         35                  40                  45

Pro Ser Glu Cys Asp Arg Arg Cys Lys Lys Thr Gln Tyr His Lys Ala
     50                  55                  60

Cys Ile Thr Phe Cys Asn Lys Cys Arg Lys Cys Leu Cys Val Pro
 65                  70                  75                  80

Pro Gly Tyr Tyr Gly Asn Lys Gln Val Cys Ser Cys Tyr Asn Asn Trp
             85                  90                  95

Lys Thr Gln Glu Gly Gly Pro Lys Cys Pro
             100                 105
```

<210> SEQ ID NO 97
<211> LENGTH: 18
<212> TYPE: PRT
<213> ORGANISM: Artificial Sequence
<220> FEATURE:
<223> OTHER INFORMATION: consensus sequence
<221> NAME/KEY: VARIANT
<222> LOCATION: (2)...(2)
<223> OTHER INFORMATION: The amino acid at position 2 can be any amino
      acid.
<221> NAME/KEY: VARIANT
<222> LOCATION: (3)...(3)
<223> OTHER INFORMATION: The amino acid at position 3 can be any amino
      acid.
<221> NAME/KEY: VARIANT
<222> LOCATION: (6)...(6)
<223> OTHER INFORMATION: The amino acid at position 6 can be any amino
      acid.
<221> NAME/KEY: VARIANT
<222> LOCATION: (7)...(7)
<223> OTHER INFORMATION: The amino acid at position 7 can be any amino
      acid.
<221> NAME/KEY: VARIANT
<222> LOCATION: (8)...(8)
<223> OTHER INFORMATION: The amino acid at position 8 can be Cys or Ser.
<221> NAME/KEY: VARIANT
<222> LOCATION: (9)...(9)
<223> OTHER INFORMATION: The amino acid at position 9 can be any amino
      acid.
<221> NAME/KEY: VARIANT
<222> LOCATION: (10)...(10)
<223> OTHER INFORMATION: The amino acid at position 10 can be any amino
      acid, and can either be absent or present.
<221> NAME/KEY: VARIANT
<222> LOCATION: (14)...(14)
<223> OTHER INFORMATION: The amino acid at position 14 can be Pro, Ser,
      Ala, Thr, or Lys.
<221> NAME/KEY: VARIANT
<222> LOCATION: (15)...(15)
<223> OTHER INFORMATION: The amino acid at position 15 can be Gly or
      Arg.
<221> NAME/KEY: VARIANT
<222> LOCATION: (16)...(16)
<223> OTHER INFORMATION: The amino acid at position 16 can be any amino
      acid.
<221> NAME/KEY: VARIANT
<222> LOCATION: (17)...(17)
<223> OTHER INFORMATION: The amino acid at position 17 can be any amino
      acid.
<221> NAME/KEY: VARIANT
<222> LOCATION: (18)...(18)
<223> OTHER INFORMATION: The amino acid at position 18 can be Gly, Ala,
      Gln, or Arg.

<400> SEQUENCE: 97

```
Cys Xaa Xaa Cys Cys Xaa Xaa Xaa Xaa Xaa Cys Val Pro Xaa Xaa Xaa
 1               5                  10                  15

Xaa Xaa
```

<210> SEQ ID NO 98

```
<211> LENGTH: 20
<212> TYPE: PRT
<213> ORGANISM: Artificial Sequence
<220> FEATURE:
<223> OTHER INFORMATION: consensus sequence
<221> NAME/KEY: VARIANT
<222> LOCATION: (1)...(1)
<223> OTHER INFORMATION: The amino acid at position 1 can be Cys or Ser.
<221> NAME/KEY: VARIANT
<222> LOCATION: (2)...(2)
<223> OTHER INFORMATION: The amino acid at position 2 can be Pro, Ser,
      Gln, Ala, or Gly.
<221> NAME/KEY: VARIANT
<222> LOCATION: (3)...(3)
<223> OTHER INFORMATION: The amino acid at position 3 can be any amino
      acid, and can be absent or present.
<221> NAME/KEY: VARIANT
<222> LOCATION: (4)...(4)
<223> OTHER INFORMATION: The amino acid at position 4 can be any amino
      acid, and can be absent or present.
<221> NAME/KEY: VARIANT
<222> LOCATION: (7)...(7)
<223> OTHER INFORMATION: The amino acid at position 7 can be any amino
      acid.
<221> NAME/KEY: VARIANT
<222> LOCATION: (8)...(8)
<223> OTHER INFORMATION: The amino acid at position 8 can be any amino
      acid.
<221> NAME/KEY: VARIANT
<222> LOCATION: (9)...(9)
<223> OTHER INFORMATION: The amino acid at position 9 can be any amino
      acid.
<221> NAME/KEY: VARIANT
<222> LOCATION: (10)...(10)
<223> OTHER INFORMATION: The amino acid at position 10 can be any amino
      acid.
<221> NAME/KEY: VARIANT
<222> LOCATION: (11)...(11)
<223> OTHER INFORMATION: The amino acid at position 11 can be Thr, Asn,
      Ser, or Met.
<221> NAME/KEY: VARIANT
<222> LOCATION: (12)...(12)
<223> OTHER INFORMATION: The amino acid at position 12 can be any amino
      acid.
<221> NAME/KEY: VARIANT
<222> LOCATION: (13)...(13)
<223> OTHER INFORMATION: The amino acid at position 13 can be any amino
      acid.
<221> NAME/KEY: VARIANT
<222> LOCATION: (14)...(14)
<223> OTHER INFORMATION: The amino acid at position 14 can be any amino
      acid.
<221> NAME/KEY: VARIANT
<222> LOCATION: (15)...(15)
<223> OTHER INFORMATION: The amino acid at position 15 can be any amino
      acid.
<221> NAME/KEY: VARIANT
<222> LOCATION: (16)...(16)
<223> OTHER INFORMATION: The amino acid at position 16 can be any amino
      acid.
<221> NAME/KEY: VARIANT
<222> LOCATION: (17)...(17)
<223> OTHER INFORMATION: The amino acid at position 17 can be any amino
      acid, and can be absent or present.
<221> NAME/KEY: VARIANT
<222> LOCATION: (18)...(18)
<223> OTHER INFORMATION: The amino acid at position 18 can be any amino
      acid, and can be absent or present.
<221> NAME/KEY: VARIANT
<222> LOCATION: (19)...(19)
<223> OTHER INFORMATION: The amino acid at position 19 can be any amino
      acid, and can be absent or present.

<400> SEQUENCE: 98

Xaa Xaa Xaa Xaa Cys Tyr Xaa Xaa Xaa Xaa Xaa Xaa Xaa Xaa Xaa
1               5                   10                  15

Xaa Xaa Xaa Lys
```

```
<210> SEQ ID NO 99
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 99
tcgacccacg cgtccgaaaa aaaaaaaaaa aaaaaa                              36
```

ANTIMICROBIAL PEPTIDES AND METHODS OF USE

CROSS REFERENCE TO RELATED APPLICATIONS

This application is a divisional of U.S. patent application Ser. No. 09/950,933, filed Sep. 11, 2001, now U.S. Pat. No. 6,875,907, which claims priority to and benefit of U.S. Provisional Application No. 60/232,569 filed Sep. 13, 2000, both of which are herein incorporated by reference.

TECHNICAL FIELD

The present invention relates generally to plant molecular biology. More specifically, it relates to nucleic acids and methods for modulating their expression in plants and to transforming genes into plants in order to enhance disease resistance.

BACKGROUND OF THE INVENTION

Disease in plants results from biotic and abiotic causes. Biotic causes include fungi, viruses, insects, bacteria, and nematodes. Of these, fungi are the most frequent causative agents of disease in plants. Abiotic causes of disease in plants include extremes of temperature, water, oxygen, and soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

As noted, among the causative agents of infectious disease of crop plants, the phytopathogenic fungi play the dominant role. Phytopathogenic fungi cause devastating epidemics as well as significant annual crop yield losses. Pathogenic fungi attack all of the approximately 300,000 species of flowering plants. However, a single plant species can be host to only a few fungal species, and similarly, most fungi usually have a limited host range.

The antimicrobial peptide, snakin-1 has been isolated from potato tubers and found to be active against bacterial and fungal pathogens from potato and other plant species. Snakin-1 causes aggregation of both gram-positive and gram-negative bacteria. The protein is homologous to amino acid sequences deduced from cDNAs that encode gibberellin-inducible mRNAs. The protein also shares sequence motifs with kistrin and other hemotoxic snake venoms.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack.

SUMMARY OF THE INVENTION

Generally, it is the object of the present invention to provide nucleic acids and proteins relating to disease resistance, particularly antimicrobial and antifungal compositions. Such compositions are generally herein referred to as KCP-like (lysine- and cysteine-rich peptides or nucleic acids encoding these peptides). The present invention provides transgenic plants and seeds comprising the nucleic acids of the present invention, as well as transgenic plants and seeds modified to express a KCP-like polynucleotide. It is another object of the present invention to provide methods for modulating, in a transgenic plant, the expression of the nucleic acids of the present invention.

In one aspect, the present invention relates to an isolated nucleic acid molecule comprising a polynucleotide selected from the group consisting of: (a) a polynucleotide that encodes a polypeptide of SEQ ID NOS:37-72; (b) a polynucleotide comprising at least 20 contiguous bases of SEQ ID NOS:1-36; (c) a polynucleotide having at least 70% sequence identity to any of SEQ ID NOS:1-36, wherein said polynucleotide encodes a polypeptide having KCP-like activity; (d) a polynucleotide at least 25 nucleotides in length that hybridizes to a polynucleotide having the sequence set forth in SEQ ID NOS:1-36, wherein said polynucleotide encodes a polypeptide having KCP-like activity; (e) a polynucleotide comprising the sequence set forth in any of SEQ ID NOS:1-36; and, (f) a polynucleotide complementary to a polynucleotide of (a) through (e). The isolated nucleic acid can be DNA. The isolated nucleic acid can also be RNA.

In another aspect, the present invention relates to vectors comprising the polynucleotides of the present invention. Also the present invention relates to recombinant expression cassettes, comprising a nucleic acid of the present invention operably linked to a promoter.

In another aspect, the present invention is directed to a host cell into which has been introduced the recombinant expression cassette.

In yet another aspect, the present invention relates to a transgenic plant or plant cell comprising a recombinant expression cassette with a promoter operably linked to any of the isolated nucleic acids of the present invention. Plants containing the recombinant expression cassette of the present invention include but are not limited to maize, soybean, sunflower, sorghum, canola, wheat, alfalfa, cotton, rice barley, or millet. The present invention also provides transgenic seed from the transgenic plant.

In another aspect, the present invention relates to an isolated polypeptide comprising an amino acid sequence selected from the group consisting of: (a) an amino acid sequence comprising at least 25 contiguous amino acids of the sequence set forth in SEQ ID NOS:37-72; (b) an amino acid sequence having at least 75% sequence identity to the sequence set forth in SEQ ID NOS:37-72, wherein said polypeptide retains KCP-like activity; and, (c) an amino acid sequence comprising the sequences set forth in SEQ ID NOS: 37-72.

In a further aspect, the present invention relates to a method of modulating the level of protein in a plant by introducing into a plant cell a recombinant expression cassette comprising a polynucleotide of the present invention operably linked to a promoter, culturing the plant cell under plant growing conditions to produce a regenerated plant, and inducing expression of the polynucleotide for a time sufficient to modulate the protein of the present invention in the plant. Plants of the present invention include but are not limited to maize, soybean, sunflower, sorghum, canola, wheat, alfalfa, cotton, rice, barley, or millet. The level of protein in the plant can either be increased or decreased.

In yet another aspect, the present invention is directed to a method for identifying KCP-like proteins, said method comprising: (a) searching at least one protein database with a pattern selected from the group consisting of: i) a pattern representing a compound having the formula (SEQ ID NO:97) C-X(2)-C-C-X(2)-[CS]-X(1,2)-C-V-P-[PSATK]-[GR]-X(2)-[GAQR], wherein: C is cysteine; X(2) is any two amino acids selected independently from one another; [CS] is one amino acid selected from the group consisting of cysteine and serine; X(1,2) is X(1) or X(2) wherein X(1) is any one amino acid, and X(2) is any two amino acids selected independently from one another; V is valine; P is proline; [PSATK] is one amino acid selected from the group consisting of proline, serine, alanine, threonine, and lysine; [GR] is one amino acid selected from the group consisting of glycine and arginine; and [GAQR] is one amino acid selected from the group consisting of glycine, alanine, glutamine and arginine; and ii) a pattern for a compound having the formula (SEQ ID NO:98) [CS]-[PSQAG]-X(0,2)-C-Y-X(4)-[TNSM]-X(5,8)-K, wherein [CS] is one amino acid selected from the group consisting of cysteine and serine; [PSQAG] is one amino acid selected from the group consisting of proline, serine, glutamine, alanine, and glycine; X(0,2) is X(0) or X(1) or X(2) wherein X(0) is no amino acid, X(1) is any one amino acid, and X(2) is any two amino acids selected independently from one another; C is cysteine; Y is tyrosine; X(4) is any four amino acids selected independently from one another; [TNSM] is one amino acid selected from the group consisting of threonine, asparagine, serine, and methionine; X(5,8) is X(5) or X(6) or X(7) or X(8) wherein X(5) is any five amino acids selected independently from one another, X(6) is any six amino acids selected independently from one another, X(7) is any seven amino acids selected independently from one another, and X(8) is any eight amino acids selected independently from one another; and K is lysine; and, (b) selecting among retrieved proteins at least one protein comprising at least one amino acid sequence represented by at least one formula selected from said group. In one manifestation, searching is performed utilizing PHI-BLAST or PHI-PSI-BLAST under parameters comprising a default Expectation value (E) of 10, a gap opening cost with a default value of 11, and a gap extension cost with a default value of 1. In another manifestation, the PHI-BLAST or PHI-PSI-BLAST is further used with BLOSUM62 substitution matrix

DETAILED DESCRIPTION OF THE INVENTION

Overview

Novel nucleic acid molecules and polypeptide sequences from maize, rice, wheat, and soybean are provided. These polypeptides are related to the potato snakin antimicrobial protein and GASA4 or GASA5 or GAST1 homologs in plants, and are referred to as KCP-like (lysine- and cysteine-rich peptides or nucleic acids encoding these peptides). The KCP-like proteins of the invention are generally lysine- and cysteine-rich; and the last three amino acids, which are universally conserved in the proteins of the invention, are K, C, and P, in that order. Generally, the KCP-like polypeptides of the invention are natural plant protection proteins. The KCP-like polypeptides of the invention are "antimicrobial," by which is intended antibacterial, antiviral, and antifungal. Additionally, the polypeptides of the invention may enhance resistance to insects and nematodes. Consequently, the sequences of the invention are "anti-pathogenic: and therefore find use in the prevention and control of disease in plants. The invention provides ectopic constitutive or inducible expression of the nucleotide sequences to enhance disease resistance in plants. In this manner, expression of the protein can be controlled such that the protein is expressed in the tissue or developmental stages to encounter the pathogen where it is most likely to strike. The proteins also find use in controlling plant pathogens such as bacteria, fungi, insects, nematodes, and the like.

The KCP-like polypeptides of the invention can also be used for any application including coating surfaces to target microbes. In this manner, the target microbes include human pathogens or microorganisms. Surfaces that might be coated with the KCP-like polypeptides of the invention include carpets and sterile medical facilities. Polymer bound polypeptides of the invention may be used to coat surfaces. Methods for incorporating compositions with anti-microbial properties into polymers are known in the art. See U.S. Pat. No. 5,847,047, herein incorporated by reference.

Another embodiment involves the use of the compositions of the invention in the treatment and preservation of textiles. Insect pests devalue and destroy textiles and fabrics including, but not limited to, carpets, draperies, clothing, blankets, and bandages. The compositions of the invention may be applied to finished textile products or may be expressed in plants yielding fibers that are incorporated into fabrics. Insect pests that attack textiles include, but are not limited to, webbing clothes moths and carpet beetles.

Thirty six novel nucleotide sequences are provided, including nine maize sequences, nine wheat sequences, two rice sequences, and twenty-one soybean sequences. Also provided are the polypeptides encoded by these nucleotide sequences. Nine sequences from *Zea mays* are provided (designated "Zm").

Zm-KCP1 is a 730 nucleotide (nt) sequence (set forth in SEQ ID NO:1) that includes a 31 nt polyA tail (nt 700-730) and 699 nt exclusive of the polyA tail. Nucleotides 1-96 correspond to a 5' nontranslated leader, with the coding region (ATG-stop) at nt 97-441 and a 3' nontranslated region at nt 442-699. The predicted polypeptide sequence encoded by SEQ ID NO:1 is set forth in SEQ ID NO:37.

Zm-KCP2 is a 549 nucleotide sequence (set forth in SEQ ID NO:2). Nucleotides 1-241 correspond to a 5' nontranslated leader, with the coding region (ATG-stop) at nt 242-529 and a 3' nontranslated region at nt 530-549. The predicted polypeptide sequence encoded by SEQ ID NO:2 is set forth in SEQ ID NO:38.

Zm-KCP3 is a 691 nucleotide (nt) sequence (set forth in SEQ ID NO:3) including a 10 nt polyA tail (nt 682-691) and 681 nt exclusive of the polyA tail. Nucleotides 1-156 correspond to a 5' nontranslated leader, with the coding region (ATG-stop) at nt 157-504 and a 3' nontranslated region at nt 505-681. The predicted polypeptide sequence encoded by SEQ ID NO:3 is set forth in SEQ ID NO:39.

Zm-KCP4 is a 831 nucleotide sequence (set forth in SEQ ID NO:4) that includes an 18 nt polyA tail (nt 814-831) and 813 nt exclusive of the polyA tail. Nucleotides 1-143 correspond to a 5' nontranslated leader, with the coding region (ATG-stop) at nt 144-446 and a 3' nontranslated region at nt 447-813. The predicted polypeptide sequence encoded by SEQ ID NO:4 is set forth in SEQ ID NO:40.

Zm-KCP5 is a 621 nucleotide sequence (set forth in SEQ ID NO:5) that includes a 27 nt polyA tail (nt 595-621) and 594 nt exclusive of the polyA tail. Nucleotides 1-136 correspond to a 5' nontranslated leader, with the coding region (ATG-stop) at nt 137-523 and a 3' nontranslated region at nt 524-594. The predicted polypeptide sequence encoded by SEQ ID NO:5 is set forth in SEQ ID NO:41.

Zm-KCP6 is a 648 nucleotide sequence (set forth in SEQ ID NO:6) that includes an 18 nt polyA tail (nt 631-648) and 630 nt exclusive of the polyA tail. Nucleotides 1-141 correspond to a 5' nontranslated leader, with the coding region (ATG-stop) at nt 142-432 and a 3' nontranslated region at nt 433-630. The predicted polypeptide sequence encoded by SEQ ID NO:6 is set forth in SEQ ID NO:42.

Zm-KCP7 is an 806 nucleotide sequence (set forth in SEQ ID NO:7) that includes a 33 nt polyA tail (nt 774-806) and 773 nt exclusive of the polyA tail. Nucleotides 1-135 correspond to a 5' nontranslated leader, with the coding region (ATG-stop) at nt 136-525 and a 3' nontranslated region at nt 526-773. The predicted polypeptide sequence encoded by SEQ ID NO:7 is set forth in SEQ ID NO:43.

Zm-KCP8 is a 720 nucleotide sequence (set forth in SEQ ID NO:8) includes a 21 nt polyA tail (nt 700-720) and 699 nt exclusive of the polyA tail. Nucleotides 1-118 correspond to a 5' nontranslated leader, with the coding region (ATG-stop) at nt 119-403 and a 3' nontranslated region at nt 404-699. The predicted polypeptide sequence encoded by SEQ ID NO:8 is set forth in SEQ ID NO:44.

Zm-KCP9 is a 754 nucleotide (nt) sequence (set forth in SEQ ID NO:9). Nucleotides 1-101 correspond to a 5' nontranslated leader, with the coding region (ATG-stop) at nt 102-539 and a 3' nontranslated region at nt 540-754. The predicted polypeptide sequence encoded by SEQ ID NO:9 is set forth in SEQ ID NO:45.

Nine sequences from *Triticum aestivum* are provided (designated "Ta . . . ").

Ta-KCP1 is a 594 nucleotide (nt) sequence (set forth in SEQ ID NO:10) that includes a 34 nt polyA tail (nt 561-594) and 560 nt exclusive of the polyA tail. Nucleotides 1-110 correspond to a 5' nontranslated leader, with the coding region (ATG-stop) at nt 111-344 and a 3' nontranslated region at nt 345-560. The predicted polypeptide sequence encoded by SEQ ID NO:10 is set forth in SEQ ID NO:46.

Ta-KCP2 is a 677 nucleotide sequence (set forth in SEQ ID NO:11) including an 18 nt polyA tail (nt 660-677) and 659 nt exclusive of the polyA tail. Nucleotides 1-79 correspond to a 5' nontranslated leader, with the coding region (ATG-stop) at nt 80-364 and a 3' nontranslated region at nt 365-659. The predicted polypeptide sequence encoded by SEQ ID NO:11 is set forth in SEQ ID NO:47.

Ta-KCP3 is a 639 nucleotide sequence (set forth in SEQ ID NO:12) including a 27 nt polyA tail (nt 613-639) and 612 nt exclusive of the polyA tail. Nucleotides 1-80 correspond to a 5' nontranslated leader, with the coding region (ATG-stop) at nt 81-377 and a 3' nontranslated region at nt 378-612. The predicted polypeptide sequence encoded by SEQ ID NO:12 is set forth in SEQ ID NO:48.

Ta-KCP4 is a 506 nucleotide sequence (set forth in SEQ ID NO:13). Nucleotide 1 corresponds to a 5' nontranslated leader, with the coding region (ATG-stop) at nt 2-325 and a 3' nontranslated region at nt 326-506. The predicted polypeptide sequence encoded by SEQ ID NO:13 is set forth in SEQ ID NO:49.

Ta-KCP5 is a 506 nucleotide sequence (set forth in SEQ ID NO:14). Nucleotides 1-78 correspond to a 5' nontranslated leader, with the coding region (ATG-stop) at nt 79-375 and a 3' nontranslated region at nt 376-506. The predicted polypeptide sequence encoded by SEQ ID NO:14 is set forth in SEQ ID NO:50.

Ta-KCP6 is a 769 nucleotide sequence (set forth in SEQ ID NO:15) that includes a 20 nt polyA tail (nt 750-769) and 749 nt exclusive of the polyA tail. Nucleotides 1-55 correspond to a 5' nontranslated leader, with the coding region (ATG-stop) at nt 56-400 and a 3' nontranslated region at nt 401-749. The predicted polypeptide sequence encoded by SEQ ID NO:15 is set forth in SEQ ID NO:51.

Ta-KCP7 is a 692 nucleotide sequence (set forth in SEQ ID NO:16) that includes a 7 nt polyA tail (nt 686-692) and 685 nt exclusive of the polyA tail. Nucleotides 1-136 correspond to a 5' nontranslated leader, with the coding region (ATG-stop) at nt 137-448 and a 3' nontranslated region at nt 449-685. The predicted polypeptide sequence encoded by SEQ ID NO:16 is set forth in SEQ ID NO:52.

Two *Oryza sativa* sequences are provided (designated "Os . . . ").

Os-KCP3 is a 685 nucleotide sequence (set forth in SEQ ID NO:17). Nucleotides 1-87 correspond to a 5' nontranslated leader, with the coding region (ATG-stop) at nt 88-405, a 3' nontranslated region at nt 406-666, and a 19 nt polyA tail. The predicted polypeptide sequence encoded by SEQ ID NO:17 is set forth in SEQ ID NO:53.

Os-KCP4 is a 660 nucleotide sequence (set forth in SEQ ID NO:18) that includes a 4 nt polyA tail (nt 657-660) and 656 nt exclusive of the polyA tail. Nucleotides 1-75 correspond to a 5' nontranslated leader, with the coding region (ATG-stop) at nt 76-330 and a 3' nontranslated region at nt 331-656. The predicted polypeptide sequence encoded by SEQ ID NO:18 is set forth in SEQ ID NO:54.

Twenty-one *Glycine max* sequences are provided (designated "Gm . . . ").

Gm-KCP1 is a 677 nucleotide (nt) sequence (set forth in SEQ ID NO:19) that includes a 30 nt polyA tail (nt 648-677) and 647 nt exclusive of the polyA tail. Nucleotides 1-144 correspond to a 5' nontranslated leader, with the coding region (ATG-stop) at nt 145-411 and a 3' nontranslated region at nt 412-647. The predicted polypeptide sequence encoded by SEQ ID NO:19 is set forth in SEQ ID NO:55.

Gm-KCP2 is a 756 nucleotide sequence (set forth in SEQ ID NO:20) that includes a 42 nt polyA tail (nt 715-756) and 714 nt exclusive of the polyA tail. Nucleotides 1-146 correspond to a 5' nontranslated leader, with the coding region (ATG-stop) at nt 147-413 and a 3' nontranslated region at nt 414-714. The predicted polypeptide sequence encoded by SEQ ID NO:20 is set forth in SEQ ID NO:56.

Gm-KCP3 is a 579 nucleotide sequence (set forth in SEQ ID NO:21) that includes a 24 nt polyA tail (nt 556-579) and 555 nt exclusive of the polyA tail. Nucleotides 1-82 correspond to a 5' nontranslated leader, with the coding region (ATG-stop) at nt 83-349 and a 3' nontranslated region at nt 350-555. The predicted polypeptide sequence encoded by SEQ ID NO:21 is set forth in SEQ ID NO:57.

Gm-KCP4 is a 509 nucleotide sequence (set forth in SEQ ID NO:22) that includes a 19 nt polyA tail (nt 491-509) and 490 nt exclusive of the polyA tail. Nucleotides 1-51 correspond to a 5' nontranslated leader, with the coding region (ATG-stop) at nt 52-324 and a 3' nontranslated region at nt 325-490. The predicted polypeptide sequence encoded by SEQ ID NO:22 is set forth in SEQ ID NO:58.

Gm-KCP5 is a 439 nucleotide sequence (set forth in SEQ ID NO:23) that includes an 18 nt polyA tail (nt 422-439) and 421 nt exclusive of the polyA tail. Nucleotides 1-16 correspond to a 5' nontranslated leader, with the coding region (ATG-stop) at nt 17-289 and a 3' nontranslated region at nt 290-421. The predicted polypeptide sequence encoded by SEQ ID NO:23 is set forth in SEQ ID NO:59.

Gm-KCP6 is a 783 nucleotide sequence (set forth in SEQ ID NO:24) that includes a 19 nt polyA tail (nt 765-783) and 764 nt exclusive of the polyA tail. Nucleotides 1-54 correspond to a 5' nontranslated leader, with the coding region (ATG-stop) at nt 55-345 and a 3' nontranslated region at nt 346-764. The predicted polypeptide sequence encoded by SEQ ID NO:24 is set forth in SEQ ID NO:60.

Gm-KCP7 is a 607 nucleotide sequence (set forth in SEQ ID NO:25) that includes a 21 nt polyA tail (nt 587-607) and 586 nt exclusive of the polyA tail. Nucleotides 1-38 correspond to a 5' nontranslated leader, with the coding region (ATG-stop) at nt 39-386 and a 3' nontranslated region at nt 387-586. The predicted polypeptide sequence encoded by SEQ ID NO:25 is set forth in SEQ ID NO:61.

Gm-KCP8 is a 788 nucleotide sequence (set forth in SEQ ID NO:26) that includes a 19 nt polyA tail (nt 770-788) and 769 nt exclusive of the polyA tail. Nucleotides 1-159 correspond to a 5' nontranslated leader, with the coding region (ATG-stop) at nt 160-513 and a 3' nontranslated region at nt 514-769. The predicted polypeptide sequence encoded by SEQ ID NO:26 is set forth in SEQ ID NO:62.

Gm-KCP9 is a 996 nucleotide sequence (set forth in SEQ ID NO:27) that includes a 62 nt polyA tail (nt 935-996) and 934 nt exclusive of the polyA tail. Nucleotides 1-313 correspond to a 5' nontranslated leader, with the coding region (ATG-stop) at nt 314-673 and a 3' nontranslated region at nt 674-934. The predicted polypeptide sequence encoded by SEQ ID NO:27 is set forth in SEQ ID NO:63.

Gm-KCP10 is a 615 nucleotide sequence (set forth in SEQ ID NO:28) that includes a 22 nt polyA tail (nt 594-615) and 593 nt exclusive of the polyA tail. Nucleotides 1-63 correspond to a 5' nontranslated leader, with the coding region (ATG-stop) at nt 64-363 and a 3' nontranslated region at nt 364-593. The predicted polypeptide sequence encoded by SEQ ID NO:28 is set forth in SEQ ID NO:64.

Gm-KCP11 is a 628 nucleotide sequence (set forth in SEQ ID NO:29) that includes a 21 nt polyA tail (nt 608-628) and 607 nt exclusive of the polyA tail. Nucleotides 1-48 correspond to a 5' nontranslated leader, with the coding region (ATG-stop) at nt 49-396 and a 3' nontranslated region nt 397-607. The predicted polypeptide sequence encoded by SEQ ID NO:29 is set forth in SEQ ID NO:65.

Gm-KCP14 is a 1066 nucleotide sequence (set forth in SEQ ID NO:30) that includes a 17 nt polyA tail (nt 1050-1066) and 1049 nt exclusive of the polyA tail. Nucleotides 1-188 correspond to a 5' nontranslated leader, with the coding region (ATG-stop) at nt 189-764 and a 3' nontranslated region at nt 765-1049. The predicted polypeptide sequence encoded by SEQ ID NO:30 is set forth in SEQ ID NO:66.

Gm-KCP15 is a 697 nucleotide sequence (set forth in SEQ ID NO:31) that includes a 40 nt polyA tail (nt 658-697) and 657 nt exclusive of the polyA tail. Nucleotides 1-109 correspond to a 5' nontranslated leader, with the coding region (ATG-stop) at nt 110-433 and a 3' nontranslated region at nt 434-657. The predicted polypeptide sequence encoded by SEQ ID NO:31 is set forth in SEQ ID NO:67.

Gm-KCP16 is a 692 nucleotide sequence (set forth in SEQ ID NO:32) that includes a 17 nt polyA tail (nt 676-692) and 675 nt exclusive of the polyA tail. Nucleotides 1-113 correspond to a 5' nontranslated leader, with the coding region (ATG-stop) at nt 114-437 and a 3' nontranslated region at nt 438-675. The predicted polypeptide sequence encoded by SEQ ID NO:32 is set forth in SEQ ID NO:68.

Gm-KCP17 is a 702 nucleotide sequence (set forth in SEQ ID NO:33) that includes a 22 nt polyA tail (nt 681-702) and 680 nt exclusive of the polyA tail. Nucleotides 1-86 correspond to a 5' nontranslated leader, with the coding region (ATG-stop) at nt 87-419 and a 3' nontranslated region at nt 420-680. The predicted polypeptide sequence encoded by SEQ ID NO:33 is set forth in SEQ ID NO:69.

Gm-KCP18 is a 783 nucleotide sequence (set forth in SEQ ID NO:34) that includes a 53 nt polyA tail (nt 731-783) and 730 nt exclusive of the polyA tail. Nucleotides 1-120 correspond to a 5' nontranslated leader, with the coding region (ATG-stop) at nt 121-441 and a 3' nontranslated region at nt 442-730. The predicted polypeptide sequence encoded by SEQ ID NO:34 is set forth in SEQ ID NO:70.

Gm-KCP19 is a 742 nucleotide sequence (set forth in SEQ ID NO:35) including a 47 nt polyA tail (nt 696-742) and 695 nt exclusive of the polyA tail. Nucleotides 1-206 correspond to a 5' nontranslated leader, with the coding region (ATG-stop) at nt 207-578 and a 3' nontranslated region at nt 579-695. The predicted polypeptide sequence encoded by SEQ ID NO:35 is set forth in SEQ ID NO:71.

Gm-KCP20 is a 652 nucleotide sequence (set forth in SEQ ID NO:36) that includes a 32 nt polyA tail (nt 621-652) and 620 nt exclusive of the polyA tail. Nucleotides 1-93 correspond to a 5' nontranslated leader, with the coding region (ATG-stop) at nt 94-387 and a 3' nontranslated region at nt 388-620. The predicted polypeptide sequence encoded by SEQ ID NO:36 is set forth in SEQ ID NO:72.

The KCP-like family of sequences appear to be conserved among dicot and monocot plants. There is nearly as great diversity of genes within species as between species. There are multiple genes for the sequences within a single plant species. Garnier structure predictions indicate that the proteins are disposed towards Turn (T) structures, as expected of proteins having cysteine cross-linkages. The presence of signal or transit peptides was determined for all the KCP-like sequences. Most of the KCP-like proteins of the invention predict a transit peptide, indicating that the proteins are secreted and extracellular, although a few may be localized intracellularly.

Generally, the KCP-like proteins are small, averaging about 6979 Daltons and about 64 amino acids. All of the KCP-like proteins are about the same length in the mature peptide bioactive region. The cysteine content averages 18.2% (molar percent). This small variation reflects the slight differences in size; the conserved cysteines are present in all of the proteins. The KCP-like proteins are high in lysine, with an average lysine content of 10.8%. The few proteins with low lysine content all had very high arginine content, arginine being another positively charged amino acid (and thus a conservative amino acid change). All the proteins are basic with an average pI of 8.55, indicating that the proteins are cationic. Thus, the proteins are small cysteine-rich, lysine-rich and cationic, all characteristics of many known antimicrobial proteins. The KCP-like proteins of the invention can be used in combination with other antimicrobial proteins, such as defensin, thionin, chitinases, glucanases, and the like. Further, the activity of the polypeptides may be synergistic when used with such other antimicrobial proteins.

The present invention provides, among other things, compositions and methods for modulating (i.e., increasing or decreasing) the level of polynucleotides and polypeptides of the present invention in plants or any other host cell. In particular, the polynucleotides and polypeptides of the present invention can be expressed temporally or spatially, e.g., at developmental stages, in tissues, and/or in quantities, which are uncharacteristic of non-recombinantly engineered plants.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in compound screening assays, for detection of any number of allelic variants (polymorphisms), orthologs, or paralogs of the gene, or for site-directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents, which bind, intercalate, cleave and/ or crosslink to the isolated nucleic acids of the present invention can also be used to modulate transcription or translation. The present invention also provides isolated proteins comprising a polypeptide of the present invention (e.g., preproenzyme, proenzyme, or enzymes).

The isolated nucleic acids and proteins of the present invention can be used over a broad range of plant types, particularly monocots such as the species of the family Gramineae, including species of the genera *Sorghum* (e.g. *S. bicolor*), *Oryza, Avena, Hordeum, Secale, Triticum* and *Zea mays*, and dicots such as Glycine. The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Pisum, Phaseolus, Lolium,* and *Allium*.

Other examples of plant species of interest include, but are not limited to, *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The invention is drawn to compositions and methods for inducing resistance in plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959, and Cammue et al. (1992) *J. Biol. Chem.* 267: 2228-2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellaturn, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including *Heterodera* and *Glo-* bodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicomis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis* grandis, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

DEFINITIONS

Units, prefixes, and symbols may be denoted in their SI accepted form. Unless otherwise indicated, nucleic acids are written left to right in 5' to 3' orientation, and amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D H Persing et al., Ed., American Society for Microbiology, Washington, D.C. (1993). The product of amplification is termed an amplicon.

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

By "encoding" or "encoded," with respect to a specified nucleic acid is intended that the nucleic acid comprises the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons, as these preferences have been shown to differ (Murray et al. (1989) *Nucl. Acids Res.* 17: 477-498). Thus, the maize preferred codon for a particular amino acid might be derived from known gene sequences from maize. Maize codon usage for 28 genes from maize plants is listed in Table 4 of Murray et al., supra.

As used herein, "heterologous" in reference to a nucleic acid means a nucleic acid that originates from a foreign species, or, if from the same species, is substantially modified from its native form in composition and/or genomic locus by deliberate human intervention. For example, a promoter operably linked to a heterologous structural gene is from a species different from that species from which the structural gene was derived, or, if from the same species, one or both are substantially modified from their original form. A heterologous protein may originate from a foreign species, or, if from the same species, is substantially modified from its original form by deliberate human intervention.

By "host cell" is meant a cell which contains a vector and supports the replication and/or expression of the vector. Host cells may be prokaryotic cells such as *E. coli* or eukaryotic cells such as yeast, insect, amphibian, or mammalian cells. Preferably, host cells are monocotyledonous or dicotyledonous plant cells. A particularly preferred monocotyledonous host cell is a maize host cell.

The term "introduced" in the context of inserting a nucleic acid into a cell means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow one of skill in the art to follow the transmission of each of the chromosomes of that pair. Use of one or a plurality of markers may define a genotype.

As used herein, "nucleic acid" includes reference to a deoxyribonucleotide or ribonucleotide polymer in either single- or double-stranded form, and unless otherwise limited encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as: Berger and Kimmel, *Guide to Molecular Cloning Techniques, Methods in Enzymology*, Vol. 152, Academic Press, Inc., San Diego, Calif. (Berger); Sambrook et al. (1989) *Molecular Cloning—A Laboratory Manual*, $2^{nd}$ ed., Vol. 1-3; and *Current Protocols in Molecular Biology*, F. M. Ausubel et al., Eds., Current Protocols, a joint venture between Greene Publishing Associates, Inc. and John Wiley & Sons, Inc. (1994).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including among other things simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The essential nature of such analogues of naturally occurring amino acids is that when incorporated into a protein, that protein is specifically reactive to antibodies elicited to a protein having the same amino acid sequence but consisting entirely of naturally occurring amino acids. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well. Further, this invention contemplates the use of both the methionine-containing and the methionine-less amino terminal variants of the protein of the invention.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

As used herein, "operably linked" includes reference to a functional linkage between a promoter and a second sequence wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include but are not limited to those that are obtained from plants, plant viruses, and bacteria which comprise genes expressed in plant cells, such as *Agrobacterium* or *Rhizobium*. Examples of promoters under developmental control include promoters that preferentially initiate transcription in certain tissues, such as leaves, roots, or seeds. Such promoters are referred to as "tissue preferred." A "cell-type-preferred" promoter preferentially drives expression in certain cell types in one or more organs, for example, vascular cells in roots or leaves. An "inducible" or "repressible" promoter is a promoter which is under environmental control, or affected by environmental conditions. Examples of environmental conditions that may effect transcription by inducible promoters include anaerobic conditions or the presence of light. Tissue-preferred, cell-type-preferred, and inducible promoters constitute the class of "non-constitutive" promoters. A "constitutive" promoter is a promoter which is active under most environmental conditions.

As used herein, "recombinant" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed, or not expressed at all as a result of deliberate human intervention. The term "recombinant" as used herein does not encompass the alteration of the cell or vector by naturally occurring events (e.g., spontaneous mutation and natural transformation, transduction, or transposition), such as those occurring without deliberate human intervention.

As used herein, a "recombinant expression cassette" is a nucleic acid construct generated recombinantly or synthetically and having a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed and a promoter.

The term "residue" or "amino acid residue" or "amino acid" are used interchangeably herein to refer to an amino acid that is incorporated into a protein, polypeptide, or peptide (collectively, "protein"). The amino acid may be a naturally occurring amino acid and, unless otherwise limited, may encompass non-natural analogs of natural amino acids that can function in a manner similar to that of naturally occurring amino acids.

The term "selectively hybridizes" includes a reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementarity) with each other.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire KCP-like sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode a KCP-like polypeptide and which hybridize under stringent conditions to the sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR*

Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the KCP-like sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire KCP-like sequences disclosed herein, or one or more portions thereof, may be used as a probe capable of specifically hybridizing to corresponding KCP-like sequences and messenger RNAs. To achieve specific hybridization under a variety of conditions, such probes include sequences that are unique among KCP-like sequences and are preferably at least about 10 nucleotides in length, and most preferably at least about 20 nucleotides in length. Such probes may be used to amplify corresponding KCP-like sequences from a chosen plant or other organism by PCR. This technique may be used to isolate additional coding sequences from a desired plant or other organism or as a diagnostic assay to determine the presence of coding sequences in a plant or other organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

As used herein, the term "plant" includes reference to whole plants, plant organs (e.g., leaves, stems, roots, etc.), seeds, and plant cells and progeny of same. "Plant cell" as used herein includes without limitation seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. Preferred plants include but are not limited to maize, soybean, sunflower, sorghum, canola, wheat, alfalfa, cotton, rice, barley, and millet. A particularly preferred plant is maize (*Zea mays*).

As used herein, "transgenic plant" refers to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid. The term "transgenic" includes those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See, for example, web sites such as ncbi.nlm.nih.gov. Alignment may also be performed manually by inspection.

Unless otherwise stated, sequence identity/similarity values provided herein refer to the value obtained using GAP version 10 using the following parameters: identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of any of SEQ ID NOS:37-72, including exemplary polynucleotides of SEQ ID NOS:1-36;

(b) a polynucleotide which is the product of amplification from a *Zea mays* nucleic acid library using primer pairs which selectively hybridize under stringent conditions to loci within a polynucleotide selected from the group consisting of SEQ ID NOS:1-36;

(c) a polynucleotide which selectively hybridizes to a polynucleotide of (a) or (b);

(d) a polynucleotide having at least about 55%, 60%, 65%, 70%, 75%, 80%, 85%, 90%, 91%, 92%, 93%, 94%, 95%, 96%, 97%, 98%, 99%, or 100% sequence identity with polynucleotides of (a), (b), or (c);

(e) complementary sequences of polynucleotides of (a), (b), (c), or (d);

(f) a polynucleotide comprising at least 20, 25, 30, 35, 40, 45, 50, 55, 60, 65, or 70 contiguous nucleotides from a polynucleotide of (a), (b), (c), (d), or (e); and (g) an isolated polynucleotide made by the process of: 1) providing a full-length enriched nucleic acid library, 2) selectively hybridizing the polynucleotide to a polynucleotide of (a), (b), (c), (d), (e), (f), (g), or (h), thereby isolating the polynucleotide from the nucleic acid library.

The present invention provides, among other things, isolated nucleic acids of RNA, DNA, and analogs and/or chimeras thereof, comprising a polynucleotide of the present invention.

A. Polynucleotides Encoding a Polypeptide of the Present Invention

The present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid, which encodes a polypeptide of the present invention, is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

The present invention provides an isolated nucleic acid comprising a polynucleotide of the present invention, wherein the polynucleotides are amplified under nucleic acid amplification conditions from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat, or rice. The plant nucleic acid library can also be constructed from a dicot such as soybean. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama and Sugano (1994) *Gene* 138: 171-174), Biotinylated CAP Trapper (Carninci et al. (1996) *Genomics* 37: 327-336), and CAP Retention Procedure (Edery et al. (1995) *Molecular and Cellular Biology* 15: 3363-3371). Rapidly growing tissues or rapidly dividing cells are preferred for use as an mRNA source for construction of a cDNA library. Growth stages of corn is described in "How a Corn Plant Develops," Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, eds. (Academic Press, Inc., San Diego), pp. 28-38 (1990)); see also, U.S. Pat. No. 5,470,722, and *Current Protocols in Molecular Biology*, Unit 15.6, Ausubel, et al., Eds., Greene Publishing and Wiley-Interscience, New York (1995); Frohman and Martin, Techniques 1:165 (1989).

Optionally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the Send of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity), or verifying the presence of one or more linear epitopes, which are specific to a polypeptide of the present invention. Methods for protein synthesis from PCR derived templates are known in the art and available commercially. See, e.g., Amersham Life Sciences, Inc, Catalog '97, p. 354.

C. Polynucleotides that Selectively Hybridize to a Polynucleotide of (A) or (B)

The present invention provides isolated nucleic acids comprising polynucleotides of the present invention, wherein the polynucleotides selectively hybridize, under selective hybridization conditions, to a polynucleotide of section (A) or (B) as discussed above. Thus, the polynucleotides of this embodiment can be used for isolating, detecting, and/or quantifying nucleic acids comprising the polynucleotides of section (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley, and rice. The cDNA library comprises at least 50% to 95% full-length sequences (for example, at least 50%, 60%, 70%, 80%, 90%, or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity.

D. Polynucleotides Having a Specific Sequence Identity with the Polynucleotides of (A), (B) or (C)

The present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST or GAP algorithms as described elsewhere herein. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

E. Polynucleotides Encoding a Protein Having a Subsequence from a Prototype Polypeptide and Cross-Reactive to the Prototype Polypeptide The present invention provides isolated nucleic acids comprising polynucleotides of the present invention, wherein the polynucleotides encode a protein having a subsequence of contiguous amino acids from a prototype polypeptide of the present invention such as are provided in section (A), above. The subsequences of a nucleotide sequence may encode protein fragments that retain the biological activity of the native protein and hence KCP-like activity. Alternatively, subsequences of a nucleotide sequence that are useful as hybridization probes generally do not encode fragment proteins retaining biological activity. Thus, subsequences of a nucleotide sequence may range from at least about 20 nucleotides, about 50 nucleotides, about 100 nucleotides, and up to the full-length nucleotide sequence encoding the proteins of the invention.

The length of contiguous amino acids from the prototype polypeptide is selected from the group of integers consisting of from at least 10 to the number of amino acids within the prototype sequence. Thus, for example, the polynucleotide can encode a polypeptide having a biologically active subsequence having at least 10, 15, 20, 25, 30, 35, 40, 45, 50, 55, 60, 65, 70, 75 contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

Thus, a subsequence of a KCP-like nucleotide sequence may encode a biologically active portion of a KCP-like protein, or it may be a fragment that can be used as a hybridization probe or PCR primer using methods disclosed below. A biologically active portion of a KCP-like protein can be prepared by isolating a portion of one of the KCP-like nucleotide sequences of the invention, expressing the encoded portion of the KCP-like protein (e.g., by recombinant expression in vitro), and assessing the activity of the encoded portion of the KCP-like protein. Nucleic acid molecules that are subsequences of a KCP-like nucleotide sequence comprise at least 16, 20, 50, 75, 100, 150, 200, 250, 300, 350, or 400 nucleotides, or up to the number of nucleotides present in a full-length KCP-like nucleotide sequence disclosed herein (for example, 730 nucleotides for SEQ ID NO:1, 549 nucleotides for SEQ ID NO:2, 691 nucleotides for SEQ ID NO:3, 831 nucleotides for SEQ ID NO:4, 621 nucleotides for SEQ ID NO:5, 648 nucleotides for SEQ ID NO:6, 806 nucleotides for SEQ ID NO:7, 720 nucleotides for SEQ ID NO:8, 754 nucleotides for SEQ ID NO:9, 594 nucleotides for SEQ ID NO:10, 677 nucleotides for SEQ ID NO:11, 639 nucleotides for SEQ ID NO:12, 506 nucleotides for SEQ ID NO:13, 506 nucleotides for SEQ ID NO:14, 769 nucleotides for SEQ ID NO:15, 692 nucleotides for SEQ ID NO:16, 685 nucleotides for SEQ ID NO:17, 660 nucleotides for SEQ ID NO:18, 677 nucleotides for SEQ ID NO:19, 756 nucleotides for SEQ ID NO:20, 579 nucleotides for SEQ ID NO:21, 509 nucleotides for SEQ ID NO:22, 439 nucleotides for SEQ ID NO:23, 783 nucleotides for SEQ ID NO:24, 607 nucleotides for SEQ ID NO:25, 788 nucleotides for SEQ ID NO:26, 996 nucleotides for SEQ ID NO:27, 615 nucleotides for SEQ ID NO:28, 628 nucleotides for SEQ ID NO:29, 1066 nucleotides for SEQ ID NO:30, 697 nucleotides for SEQ ID NO:31, 692 nucleotides for SEQ ID NO:32, 702 nucleotides for SEQ ID NO:33, 783 nucleotides for SEQ ID NO:34, 742 nucleotides for SEQ ID NO:35, 652 nucleotides for SEQ ID NO:36, respectively).

In generating subsequences or fragments retaining biological activity, a variety of methods are contemplated for measuring the activity of such subsequences or fragments, including both in vivo and in silico methods. For example, biological activity of a subsequence or fragment may be determined using any of the variety of biological assays described elsewhere herein. Alternatively, or in addition, such subsequences or fragments may be generated using the guidance provided by methods known to the skilled artisan to predict protein regions of important functionality. For example, subsequences or fragments may be generated which preserve conserved regions of sequence, as identified using alignment programs or domain-identification programs known to the skilled artisan. Since conserved regions are important for biological activity, such in silico predictions provide guidance for producing subsequences or fragments with the requisite properties. Conserved regions may be identified using, for example, the information provided by the consensus sequences of the present invention. That is, regions which are likely to be important for biological activity are expected to include those identified using either SEQ ID NO:97 or SEQ ID NO:98, and it is therefore generally advantageous to conserve, or minimally vary, regions identified by methods using these sequences. For example, the Zm-KCP1 protein sequence (SEQ ID NO:37) contains the SEQ ID NO:97 consensus sequence at positions 77-93, and the SEQ ID NO:98 consensus sequence at positions 98-112. Thus it is generally advantageous to preserve, or minimally or conservatively vary these two regions in subsequences or fragments. The skilled artisan would know to identify regions corresponding to SEQ ID NO:97 or SEQ ID NO:98 in other protein sequences or corresponding nucleotide sequences of the present invention and preserve these regions in the same manner as just described.

The proteins encoded by polynucleotides of this embodiment, when presented as an immunogen, elicit the production of polyclonal antibodies which specifically bind to a prototype polypeptide such as (but not limited to) a polypeptide encoded by the polynucleotide of sections (A) or (B) above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 70%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)-(E)

The present invention provides isolated nucleic acids comprising polynucleotides complementary to the polynucleotides of sections A-E, above. As those of skill in the art will recognize, complementary sequences base pair throughout the entirety of their length with the polynucleotides of sections (A)-(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides that are Subsequences of the Polynucleotides of (A)-(F)

The present invention provides isolated nucleic acids comprising polynucleotides which comprise at least 15 contiguous bases from the polynucleotides of sections (A) (B), (C), (D), (E), or (F) (i.e., sections (A)-(F), as discussed above). A subsequence of a KCP-like nucleotide sequence may encode a biologically active portion of a KCP-like protein, or it may be a fragment that can be used as a hybridization probe or PCR primer using methods disclosed elsewhere herein. Subsequences of a KCP-like nucleotide sequence that are useful as hybridization probes or PCR primers generally need not encode a biologically active portion of a KCP-like protein.

The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 contiguous nucleotides in length from the polynucleotides of sections (A) through (F). Optionally, the number of such subsequences encoded by a polynucleotide of the instant embodiment can be any integer selected from the group consisting of from 1 to 1000, such as 2, 3, 4, or 5. The subsequences can be separated by any integer of nucleotides from 1 to the number of nucleotides in the sequence such as at least 5, 10, 15, 20, 25, 30, 35, 40, 45, 50, 75, 100, 200, 300, 400, 500, 600, 700, 800, 900, or 1000 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it is derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides that are Variants of the Polynucleotides of (A)-(G).

By "variants" is intended substantially similar sequences. For nucleotide sequences, conservative variants include those sequences that, because of the degeneracy of the genetic code, encode the amino acid sequence of one of the KCP-like polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis, but which still encode a protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

I. Polynucleotides from a Full-length Enriched cDNA Library having the Physico-Chemical Property of Selectively Hybridizing to a Polynucleotide of (A)-(H)

The present invention provides an isolated polynucleotide from a full-length enriched cDNA library having the physico-chemical property of selectively hybridizing to a polynucleotide of sections (A), (B), (C), (D), (E), (F), (G), or (H) as discussed above. Methods of constructing full-length enriched cDNA libraries are known in the art and discussed briefly below. The cDNA library comprises at least 50% to 95% full-length sequences (for example, at least 50%, 60%, 70%, 80%, 90%, or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley, and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 91%, 92%, 93%, 94%, 95%, 96%, 97%, 98%, 99%, up to 100% sequence identity over the length of the hybridized region. Full-length enriched cDNA libraries can be normalized to increase the representation of rare sequences.

J. Polynucleotide Products Made by a cDNA Isolation Process

The present invention provides an isolated polynucleotide made by the process of: 1) providing a full-length enriched nucleic acid library; and 2) selectively hybridizing the polynucleotide to a polynucleotide of sections (A), (B), (C), (D), (E), (F), (G), (H), or (I) as discussed above, and thereby isolating the polynucleotide from the nucleic acid library. Full-length enriched nucleic acid libraries are constructed and selective hybridization conditions are used, as discussed below. Such techniques, as well as nucleic acid purification procedures, are well known in the art. Purification can be conveniently accomplished using solid-phase methods; such methods are well known to those of skill in the art and kits are available from commercial suppliers such as Advanced Biotechnologies (Surrey, UK). For example, a polynucleotide of sections (A)-(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using standard recombinant methods, synthetic techniques, or combinations thereof. In some embodiments, the polynucleotides of the present invention will be cloned, amplified, or otherwise constructed from a monocot.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize under stringent conditions to the polynucleotides of the present invention are used to identify the desired sequence in a cDNA or genomic DNA library. Techniques for the isolation of RNA and construction of cDNA and genomic libraries are well known to those of ordinary skill in the art. See, e.g., *Plant Molecular Biology: A Laboratory Manual*, Clark, ed., Springer-Verlag, Berlin (1997), and *Current Protocols in Molecular Biology*, Ausubel, et al., eds., Greene Publishing and Wiley-Interscience, New York (1995).

A1. Full-length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al. (1996) *Genomics* 37:327-336. Other methods for producing full-length libraries are known in the art. See, e.g., Edery et al. (1995) *Mol. Cell. Biol.* 15(6):3363-3371 and PCT Application WO 96/34981.

A2. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko (1990) *Nucl. Acids. Res.* 18(19):5705-5711; Patanjali et al. (1991) *Proc. Natl. Acad. U.S.A.* 88:1943-1947; U.S. Pat. Nos. 5,482,685, 5,482, 845, and 5,637,685. In an exemplary method described by Soares et al. (1994) *Proc. Natl. Acad. Sci. USA* 91:9228-9232, normalization resulted in reduction of the abundance of clones from a range of four orders of magnitude to a narrow range of only 1 order of magnitude.

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in *Plant Molecular Biology: A Laboratory Manual*, Clark, Ed., Springer-Verlag, Berlin (1997); Kho and Zarbl (1991) *Technique* 3(2):58-63; Sive and St. John (1988) *Nucl. Acids Res.* 16(22):1 0937; *Current Protocols in Molecular Biology*, Ausubel, et al., eds., Greene Publishing and Wiley-Interscience, New York (1995); and, Swaroop et al. (1991) *Nucl. Acids Res.*, 19(17):4725-4730. cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al. (1989) *Molecular Cloning: A Laboratory Manual*, 2nd Ed., Cold Spring Harbor Laboratory Vols. 1-3, Methods in Enzymology, Vol. 152: *Guide to Molecular Cloning Techniques*, Berger and Kimmel, eds., San Diego: Academic Press, Inc. (1987), *Current Protocols in Molecular Biology*, Ausubel, et al., eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either or both of the hybridization and the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. (1997) *BioTechniques* 22(3):481-486 describe a PCR-based method in which the longest cDNA is identified in the first step so that incomplete clones can be eliminated from study. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetra. Lett.* 22:1859-1862; the solid phase phosphoramidite triester method described by Beaucage and Caruthers (1981) *Tetra. Letts.* 22:1859-1862, e.g., using an automated synthesizer, e.g., as described in Needham-VanDevanter et al. (1984) *Nucleic Acids Res.* 12: 6159-6168; and the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The KCP-like sequences of the invention are provided in expression cassettes for expression in the plant of interest. The cassette will include 5' and 3' regulatory sequences operably linked to a KCP-like sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the KCP-like sequence to be under the transcriptional regulation of the regulatory regions. The expression cassette may additionally contain selectable marker genes.

The expression cassette will include in the 5'-3' direction of transcription, a transcriptional and translational initiation region, a KCP-like sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of KCP-like polypeptides in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-selective/preferred expression), a transcription initiation start site, a ribosome binding site, an RNA processing signal, a transcription termination site, and/or a polyadenylation signal.

A number of promoters can be used in the practice of the invention. In one embodiment, a plant promoter fragment can be employed which will direct expression of a polynucleotide of the present invention in all tissues of a regenerated plant. Such promoters are referred to herein as "constitutive" promoters and are active under most environmental conditions and stated of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter (Christensen et al. (1992) *Plant iMol Biol* 18:675-689; Bruce et al. (1989) *Proc Natl Acad Sci USA* 86:9692-9696), the Smas promoter, the cinnamyl alcohol dehydrogenase promoter (U.S. Pat. No. 5,683,439), the Nos promoter, the pEmu promoter, the Rubisco promoter, the GRP1-8 promoter, the maize constitutive promoters described in PCT Publication No. WO 99/43797 which include the histone H2B, metallothionein, alpha-tubulin 3, elongation factor efla, ribosomal protein rps8, chlorophyll a/b binding protein, and glyceraldehyde-3-phosphate dehydrogenase promoters, and other transcription initiation regions from various plant genes known to those of skill.

Where low level expression is desired, weak promoters will be used. It is recognized that weak inducible promoters may be used. Additionally, either a weak constitutive or a weak tissue specific promoter may be used. Generally, by "weak promoter" is intended a promoter that drives expression of a coding sequence at a low level. By low level is intended at levels of about $\frac{1}{1000}$ transcripts to about $\frac{1}{100,000}$ transcripts to about $\frac{1}{500,000}$ transcripts. Alternatively, it is recognized that weak promoters also encompass promoters that are expresses in only a few cells and not in others to give a total low level of expression. Such weak constitutive promoters include, for example, the core promoter of the Rsyn7 (PCT Publication No. WO 97/44756), the core 35S CaMV promoter, and the like. Where a promoter is expressed at unacceptably high levels, portions of the promoter sequence can be deleted or modified to decrease expression levels. Additionally, to obtain a varied series in the level of expression, one can also make a set of transgenic plants containing the polynucleotides of the present invention with a strong constitutive promoter, and then rank the transgenic plants according to the observed level of expression. The transgenic plants will show a variety in performance, from high expression to low expression. Factors such as chromosomal position effect, cosuppression, and the like will affect the expression of the polynucleotide.

Alternatively, the plant promoter can direct expression of a polynucleotide of the present invention under environmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi et al. (1983) *Meth J. Plant Pathol.* 89:245-254; Uknes et al. (1992) *The Plant Cell* 4:645-656; Van Loon (1985) *Plant Mol. Virol.* 4:111-116; PCT Publication No. WO 99/43819.

Of interest are promoters that are expressed locally at or near the site of pathogen infection. See, for example, Marineau et al. (1987) *Plant Mol. Biol.* 9:335-342; Matton et al. (1987) *Molecular Plant-Microbe Interactions* 2:325-342; Somssich et al. (1986) *Proc. Natl. Acad. Sci. USA* 83:2427-2430; Somssich et al. (1988) *Mol. Gen. Genetics* 2:93-98; Yang (1996) *Proc. Natl. Acad. Sci. USA* 93:14972-14977. See also, Chen, et al. (1996) *Plant J.* 10:955-966; Zhang and Sing (1994) *Proc. Natl. Acad. Sci. USA* 91:2507-2511; Warner et al. (1993) *Plant J.* 3:191-201, and Siebertz et al. (1989) *Plant Cell* 1:961-968, all of which are herein incorporated by reference. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200, herein incorporated by reference).

Additionally, as pathogens find entry into plants through wounds or insect damage, a wound-inducible promoter may be used in the constructs of the invention. Such wound-inducible promoter include potato proteinase inhibitor (pin II) gene (Ryan (1990) *Annu Rev Phytopath* 28:425-449; Duan et al. (1996) *Nat Biotech* 14:494-498); wun1 and wun 2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol Biol* 22:783-792; Eckelkamp et al. (1993) *FEB Letters* 323:73-76); MPI gene (Cordero et al. (1994) *The Plant J.* 6(2):141-150); and the like, herein incorporated by reference.

Examples of promoters under developmental control include promoters that initiate transcription only or preferentially in certain tissues, such as leaves, roots, fruit, seeds, or flowers. Exemplary promoters include the anther-specific promoter 5126 (U.S. Pat. Nos. 5,689,049 and 5,689,051), glob-1 promoter, and gamma-zein promoter. An exemplary promoter for leaf- and stalk-preferred expression is MS8-15 (PCT Publication No. WO 98/00533). Examples of seed-preferred promoters include, but are not limited to, 27 kD gamma zein promoter and waxy promoter (Boronat et al. (1986) *Plant Sci.* 47:95-102; Reina et al. (1990) Nucleic Acids Res. 18(21):6426; and Kloesgen et al. (1986) *Mol. Gen. Genet.* 203:237-244). Promoters that express in the embryo, pericarp, and endosperm are disclosed in U.S. Application Nos. 60/097,233 (filed Aug. 20, 1998) and 60/098,230 (filed Aug. 28, 1998), both hereby incorporated by reference. The operation of a promoter may also vary depending on its location in the genome. Thus, a developmentally-regulated promoter may become fully or partially constitutive in certain locations. A developmentally-regulated promoter can also be modified, if necessary, for weak expression.

In one embodiment, the nucleic acids encoding the KCP-like polypeptides of the invention are operably linked to a promoter as part of an expression cassette, and introduced into a crop plant such that a transgenic plant is formed. Where a high level of expression is desired, a strong constitutive promoter, such as the ubiquitin promoter is utilized. In this manner, the gene's expression is constitutively high and disease- or stress-resistance is constitutively enhanced. In another embodiment, the gene may be linked to a tissue-preferred promoter to direct expression to one or more tissues particularly known to be susceptible to a pathogen that is sought to be controlled. Tissue-preferred promoters can also be used to circumvent expression in tissues that are susceptible to food safety concern. The timing of expression can also be manipulated. For example, by judicious choice of promoter, the expression of the transgene can be enhanced earlier than that of the native gene in response to pathogen attack; thereby resulting in enhanced disease resistance. For pathogens that do not cause induced expression of the native gene, again judicious choice of promoter, may result in induced expression of this gene's coding region in response to that pathogen.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up- or down-regulate expression of a polynucleotide of the present invention. For example, endogenous promoters can be altered in vivo by mutation, deletion, and/or substitution (see U.S. Pat. No. 5,565,350 and PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3' end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene. It may also be synthetically designed and constructed.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has bee shown to increase gene expression at both the mRNA and protein levels up to 1000-fold. See Buchman and Berg (1988) *Mol. Cell. Biol.* 8:4395-4405; Callis et al. (1987) *Genes Dev.* 1:1183-1200. Such intron enhancement of gene expression is typically greatest when placed near the 5' end of the transcription unit. Use of the maize introns Adh1-S intron 1, 2, and 6, and the Bronze-1 intron are known in the art. See generally, *The Maize Handbook*, Chapter 116, Freeling and Walbot, Eds., Springer, New York (1994).

The vector comprising the sequences of a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron. The above list of selectable marker genes is not meant to be limiting. Any selectable marker gene can be used in the present invention.

Typical vectors useful for expression of genes in higher plants are well known in the art and include vectors derived from the tumor-induced (Ti) plasmid of *Agrobacterium tumefaciens*, described by Rogers et al. (1987) *Meth. Enzymol.* 153:253-277. These vectors are plant integrating vectors; upon transformation, the vectors integrate a portion of vector DNA into the genome of the host plant. Exemplary *A. tumefaciens* vectors useful herein are plasmids pKYLX6 and pKYLX7 of Schardl et al. (1987) *Gene* 61:1-11 and Berger et al. (1989) *Proc. Natl. Acad. Sci. U.S.A.* 86:8402-8406. Another useful vector herein is plasmid pBI101.2 that is available from Clontech Laboratories, Inc. (Palo Alto, Calif.).

It is recognized that with these nucleotide sequences, antisense constructions, complementary to at least a portion of the messenger RNA (mRNA) for the KCP-like sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. For an example of the use of this method to modulate expression of endogenous genes, see Sheehg et. al. (1988) *Proc. Natl. Acad. Sci.* 85:8805-8809, and U.S. Pat. No. 4,801,340.

The nucleotide sequences of the present invention may also be used in the sense orientation to suppress the expression of endogenous genes in plants.

Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See Napul et al. (1990) *The Plant Cell* 2:279-289, and U.S. Pat. Nos. 5,283,184 and 5,034,323; herein incorporated by reference.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al. (1988) *Nature* 334:585-591.

A variety of cross-linking agents, alkylating agents and radical generating species as pendant groups on polynucleotides of the present invention can be used to bind, label, detect, and/or cleave nucleic acids. For example, Vlassov et al. (1986) *Nucleic Acids Res.* 14:4065-4076 describe covalent bonding of a single-stranded DNA fragment with alkylating derivatives of nucleotides complementary to target sequences. (A report of similar work by the same group may be found in Knorre et al. (1985) *Biochimie* 67:785-789). Iverson and Dervan also showed sequence-specific cleavage of single-stranded DNA mediated by incorporation of a modified nucleotide which was capable of activating cleavage (Iverson and Dervan (1987) *J. Am. Chem. Soc.* 109:1241-1243). Meyer et al. ((1989) *J. Am. Chem. Soc.* 111:8517-8519) effect covalent crosslinking to a target nucleotide using an alkylating agent complementary to the single-stranded target nucleotide sequence. A photoactivated crosslinking to single-stranded oligonucleotides meditated by psoralen was disclosed by Lee et al. (1988) *Biochemistry* 27:3197-3203. Use of crosslinking in triple-helix forming probes was also disclosed by Home et al. ((1990) *J. Am. Chem. Soc.* 112:435-2437). Use of N4, N4-ethanocytosine as an alkylating agent to crosslink to single-stranded oligonucleotides has also been described by Webb and Matteucci ((1986) *J. Am. Chem. Soc.* 108:2764-2765); (1986) *Nucleic Acids Res.* 14:7661-7674; Feteritz et al. (1991) *J. Am. Chem. Soc.* 113:4000. Various compounds to bind, detect, label, and/or cleave nucleic acids are known in the art. See, for example, U.S. Pat. Nos. 5,543,507; 5,672,593; 5,484,908; 5,256,648; and 5,681,941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 16, 17, 18, 19, 20, 21, 22, 23, 24, 25, 26, 27, 28, 29, 30, 31, 32, 33, 34, 35, 37, 38, 39, or 40 amino acids in length, often at least 50, 55, 60, 65, 70, 75, 80, 85, 90, 95, or 100 amino acids in length.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, KCP-like activity as described herein. Such variants may result from, for example, genetic polymorphism or from human manipulation. Biologically active variants of a native KCP-like protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

As contemplated herein, the proteins of the present invention are also intended to include KCP-like sequences wherein the signal or transit peptide has been removed. As discussed elsewhere herein, most of the KCP-like proteins of the present invention are predicted to have such sequences using standard techniques such as, for example, PSORT ("Prediction of Protein Translocation Sites"), or SIGNALP ("Signal Peptide Prediction Analysis") or other known methods. Thus as a group these proteins have signal or transit peptides and are targeted for the extracellular space. It may be advantageous to use matured polypeptides in some instances, that is polypeptides where the signal or transit peptide sequence has been cleaved or otherwise removed. For example, candidate anti-microbial proteins are expected to be targetted to the extracellular space, since this is the most likely area where a pathogen will be encountered. Thus the present invention is intended to encompass such sequences.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed infra. Thus, the proteins of the present invention can be employed as immunogens for constructing antibodies immunoreactive to a protein of the present invention for such exemplary utilities as immunoassays or protein purification techniques.

The proteins of the invention may be altered in various ways including amino acid substitutions, deletions, truncations, and insertions. Methods for such manipulations are generally known in the art. For example, amino acid sequence variants of the KCP-like proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired KCP-like activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by determining the KCP-like properties of the sequence or polypeptide which has been deleted, inserted or substituted as described herein. Such properties include, for example, anti-microbial activity. Assays for measuring anti-microbial or anti-pathogenic activity are described elsewhere herein. As discussed elsewhere herein, variant nucleotide sequences and proteins also encompass sequences and proteins derived from a mutagenic and recombinogenic procedure such as DNA shuffling. With such a procedure, one or more different KCP-like coding sequences can be manipulated to create a new KCP-like possessing the desired properties. In this manner, libraries of recombinant polynucleotides are generated from a population of related sequence polynucleotides comprising sequence regions that have substantial sequence identity and can be homologously recombined in vitro or in vivo.

Expression of Proteins in Host Cells

Using the nucleic acids of the present invention, one may express a protein of the present invention in a recombinantly engineered cell such as bacterial, yeast, insect, mammalian, or preferably plant cells. The cells produce the protein in a non-natural condition (e.g., different from the natural condition in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill will recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences (which are defined herein to include promoters for transcription initiation, optionally with an operator and ribosome binding sequences) include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda-derived P L promoter and N-gene ribosome binding site (Shimatake et al. (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* spp. and *Salmonella* (Palva et al. (1983) *Gene* 22:229-235; Mosbach, et al. (1983) *Nature* 302: 543-545).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al (*Methods in Yeast Genetics*, Cold Spring Harbor Laboratory (1982)) is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences such as promoters (including 3-phosphoglycerate kinase or alcohol oxidase) and an origin of replication, termination sequences and the like as desired.

A protein of the present invention, once expressed, can be isolated from yeast by lysing the cells and applying standard protein isolation techniques to the lysate. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative cell cultures useful for the production of the peptides are mammalian cells. Mammalian cell systems often will be in the form of monolayers of cells, although mammalian cell suspensions may also be used. A number of suitable host cell lines capable of expressing intact proteins have been developed in the art and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T-ag polyA addition site), and transcriptional terminator sequences. Other animal cells useful for production of proteins of the present invention are available from, for instance, the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773-781). Additionally, gene sequences to control replication in the host cell may be incorporated into the vector such as those found in bovine papilloma virus type-vectors (see Saveria-Campo, "Bovine Papilloma Virus DNA: A Eukaryotic Cloning Vector," in *DNA Cloning Vol. II a Practical Approach*, D. M. Glover, ed., IRL Press, Arlington, Va., pp. 213-238 (1985)).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation and/or transfection may be employed.

A. Plant Transformation

The genes of the present invention can be used to transform any plant. In this manner, genetically modified plants, plant cells, plant tissue, seed, and the like can be obtained. Transformation protocols may vary depending on the type of plant cell targeted for transformation, i.e. monocot or dicot. Suitable methods of transforming plant cells include microinjection (Crossway et al. (1986) *BioTechniques* 4:320-334), electroporation (Riggs et al. (1986) *Proc. Natl. Acad. Sci. USA* 83:5602-5606), *Agrobacterium* mediated transformation (Hinchee et al. (1988) *Biotechnology* 6:15-921; U.S. Pat. No. 5,981,840 (maize); U.S. Pat. No. 5,932,782 (sunflower), European Patent No. 0486233 (sunflower); PCT Application No. WO 98/49332 (sorghum)), direct gene transfer (Paszkowski et al. (1984) *EMBO J.* 3:2717-2722), and ballistic particle acceleration (see, for example, Sanford et al., U.S. Pat. No. 4,945,050; Tomes et al., "Direct DNA Transfer into Intact Plant Cells via Microprojectile Bombardment" in Gamborg and Phillips (eds.) *Plant Cell, Tissue and Organ Culture: Fundamental Methods*, Springer-Verlag, Berlin (1995); McCabe et al. (1988) *Biotechnology* 6:923-926); U.S. Pat. No. 5,990,387 (maize), U.S. Pat. No. 5,886,244 (maize); U.S. Pat. No. 5,322,783 (sorghum)). Also see, Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al., (1990) *Biotechnology* 8:736-740 (rice); Klein et al., (1988) *Proc. Natl. Acad. Sci. USA* 85:4305-4309 (maize); Klein et al. (1988) *Biotechnology* 6:559-563 (maize); Tomes et al., "Direct DNA Transfer into Intact Plant Cells via Microprojectile Bombardment," in Gamborg and Phillips (eds.) *Plant Cell, Tissue and Organ Culture: Fundamental Methods*, Springer-Verlag, Berlin (1995) (maize); Klein et al. (1988) *Plant Physiol.* 91:440-444 (maize); Fromm et al. (1990) *Biotechnology* 8:833-839 (maize); Hooydaas-Van Slogteren & Hooykaas (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, G. P. Chapman et al., eds., pp. 197-209, Longman, N.Y. (pollen); Kaeppler et al. (1990) *Plant Cell Reports* 9:415-418; and Kaeppler et al. (1992) *Theor. Appl. Genet.* 84:560-566 (whisker-meditated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:745-750 (maize via *Agrobacterium tumefaciens*); all of which are hereby incorporated by reference.

The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the a KCP-like protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by cuttings or by tissue culture techniques to produce multiple identical plants. Selection of desirable transgenics is made and new varieties are obtained and propagated vegetatively for commercial use. In seed-propagated crops, mature transgenic plants can be self-crossed to produce a homozygous inbred plant. The inbred plant produces seed containing the newly introduced heterologous nucleic acid. These seeds can be grown to produce plants having the selected phenotype.

Parts obtained from the regenerated plant, such as flowers, seeds, leaves, branches, fruit, and the like are included in the invention, provided that these parts comprise cells comprising the isolated nucleic acid of the present invention. Progeny, variants, and mutants of the regenerated plants are also included within the scope of the invention, provided that these parts comprise the introduced nucleic acid sequences.

A preferred embodiment is a transgenic plant that is homozygous for the added heterologous nucleic acid, i.e., a transgenic plant that contains two added nucleic acid sequences, one gene at the same locus on each chromosome of a chromosome pair. A homozygous transgenic plant can be obtained by sexually mating ("selfing") a heterozygous transgenic plant that contains a single added heterologous nucleic acid, germinating some of the seed produced, and analyzing the resulting plants produced for altered expression of a polynucleotide of the present invention relative to a control plant (i.e., native, non-transgenic). Backcrossing to a parental plant and out-crossing with a non-transgenic plant are also contemplated.

B. Transfection of Prokaryotes, Lower Eukaryotes, and Animal Cells

Animal and lower eukaryotic host cells (e.g., yeast) are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE-dextran, electroporation, biolistics, and micro-injection of the DNA directly into the cells. The transfected cells are cultured by means well known in the art. See Kuchler, R. J., *Biochemical Methods in Cell Culture and Virology*, Dowden, Hutchinson and Ross, Inc (1997).

Modulating Polypeptide Levels and/or Composition

The present invention further provides a method for modulating (i.e., increasing or decreasing) the concentration or composition of the polypeptides of the present invention in a plant or part thereof. Increasing or decreasing the concentration and/or the composition of polypeptides in a plant can effect modulation. For example, increasing the ratio of polypeptides of the invention to native polypeptides can affect modulation. The method comprises: introducing a polynucleotide of the present invention into a plant cell with a recombinant expression cassette as described above to obtain a transformed plant cell, culturing the transformed plant cell under appropriate growing conditions, and inducing or repressing expression of a polynucleotide of the present invention in the plant for a time sufficient to modulate concentration and/or composition of polypeptides in the plant or plant part.

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See U.S. Pat. No. 5,565,350 and PCT/US93/03868. In some embodiments, an isolated nucleic acid comprising a promoter sequence (e.g., a vector) is transfected into a plant cell. Subsequently, a plant cell comprising the promoter operably linked to a polynucleotide of the present invention is identified and selected by means known to those of skill in the art (such as, but not limited to, Southern blot, DNA sequencing, or PCR analysis using primers specific to the promoter and to the gene and detecting amplicons produced therefrom). A plant or plant part altered or modified by the foregoing embodiments is grown under appropriate conditions for a time sufficient to modulate the concentration and/or composition of polypeptides of the present invention in the plant. Appropriate growth conditions for transformed plant cells, plant parts, and plants are well known in the art and are discussed briefly elsewhere herein.

In general, concentration or composition is increased or decreased by at least 5%, 10%, 15%, 20%, 25%, 30%, 35%, 40%, 45%, 50%, 55%, 60%, 65%, 70%, 75%, 80%, 85%, 90%, 95%, or 100% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail elsewhere herein. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for exemplary applications such as phylogenetic studies, characterizing genetic relationships among crop varieties, identifying crosses or somatic hybrids, localizing chromosomal segments affecting monogenic traits, map-based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, *The DNA Revolution*, Andrew H. Paterson (1996) (Chapter 2) in: Genome Mapping in Plants (Andrew H. Paterson, ed.) by Academic Press/R. G. Lands Company, Austin, Tex., pp. 7-21.

The particular method of genotyping in the present invention may employ any number of molecular marker analytic techniques such as, but not limited to, restriction fragment length polymorphism's (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single-copy probes are preferred. Restriction fragments from homologous chromosomes are thereby revealed. Differences in fragment size among alleles represent an RFLP; thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 4, 3, 2, or 1 cM of a gene of the present invention.

In the present invention, the nucleic acid probes employed for molecular marker mapping of plant nuclear genomes selectively hybridize (under selective hybridization conditions) to a gene encoding a polynucleotide of the present invention. In certain embodiments, the probes are selected from polynucleotides of the present invention. Typically, these probes are cDNA probes or restriction-enzyme-treated genomic clones. The length of the probes is discussed in greater detail elsewhere herein, but is typically at least 15 bases in length, more preferably at least 20, 25, 30, 35, 40, or 50 bases in length. Generally, however, the probes are less than about 1 kilobase in length. Preferably, the probes are single-copy probes that hybridize to a unique locus in the haploid chromosome compliment. Some exemplary restriction enzymes employed in RFLP mapping are EcoRI, EcoRV, and Sstl. As used herein, the term "restriction enzyme" includes reference to a composition that recognizes and cleaves at a specific nucleotide sequence, either alone or in conjunction with another composition.

The method of detecting an RFLP comprises the steps of: (a) digesting genomic DNA of a plant with a restriction enzyme; (b) hybridizing a nucleic acid probe, under selective hybridization conditions, to a sequence of a polynucleotide of the present invention comprised by said genomic DNA; (c) detecting thereby an RFLP. Other methods of differentiating polymorphic (allelic) variants of polynucleotides of the present invention can be performed by utilizing molecular marker techniques well known to those of skill in the art, including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE), heteroduplex analysis (HA), and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample. For example, the plant sample may be a sample suspected of comprising a maize polynucleotide of the present invention (e.g., gene or mRNA). The nucleic acid probe selectively hybridizes under stringent conditions to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In certain embodiments, the nucleic acid probe comprises a polynucleotide of the present invention.

UTRs and Codon Preference

In general, translational efficiency has been found to be regulated by specific sequence elements in the 5' non-coding or nontranslated or untranslated region (5' UTR) of the RNA. Positive sequence motifs include translational initiation consensus sequences (Kozak (1987) *Nucleic Acids Res.* 15:8125) and the 7-methylguanosine cap structure (Drummond et al. (1985) *Nucleic Acids Res.* 13:7375). Negative elements include stable intramolecular 5' UTR stem-loop structures (Muesing et al. (1987) *Cell* 48:691) and AUG sequences or short open reading frames preceded by an appropriate AUG in the 5' UTR (Kozak, supra, Rao et al. (1988) *Mol. Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages, such as "Codon Preference," available from the University of Wisconsin Genetics Computer Group (see Devereaux et al. (1984) *Nucleic Acids Res.* 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT Publication No. WO 96/19256. See also, Zhan et al. (1997) *Proc. Natl. Acad. Sci. USA* 94:4504-4509. Generally, sequence shuffling provides a means for generating libraries of polynucleotides having a desired characteristic for which one of skill can select or screen. Libraries of recombinant polynucleotides are generated from a population of related sequence polynucleotides which comprise sequence regions which have substantial identity and can be homologously recombined in vitro or in vivo. The population of sequence-recombined polynucleotides comprises a sub-population of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand-binding affinity greater than the non-shuffled wild-type polynucleotide. The increase in such properties can be at least 110%, 120%, 130%, 140%, or at least 150% of the wild-type value.

Chimeraplasty

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731, 181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference.

Generic and Consensus Sequences

Polynucleotides and polypeptides of the present invention further include those having: (a) a generic sequence of at least two homologous polynucleotides or polypeptides, respectively, of the present invention; and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or about at least 20, 30, 40, 50, 100, or 150 nucleotides in length. As those of skill in the art will recognize, a conservative amino acid substitution can be used to derive a consensus or generic amino acid sequence. Optionally, no more than 1 or 2 conservative amino acids are substituted for each 10 amino acid length of consensus sequence.

Similar sequences used for generation of a consensus or generic sequence include any number and combination of allelic variants of the same gene, including orthologous or paralogous sequences as provided herein. Optionally, similar sequences used in generating a consensus or generic sequence are identified using the BLAST algorithm's smallest sum probability (P(N)). Various suppliers of sequence-analysis software are listed in *Current Protocols in Molecular Biology*, (F. M. Ausubel et al., eds., Current Protocols, Greene Publishing Associates, Inc. and John Wiley & Sons, Inc. (Supplement 30)). A polynucleotide sequence is considered similar to a reference sequence if the smallest sum probability in a comparison of the test nucleic acid to the reference nucleic acid is less then about 0.1, preferably less than about 0.01, or 0.001, and more preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCER. Conveniently, default parameters of such software can be used to generate consensus or generic sequences.

Methods for Identifying KCP-Like Proteins

Methods are presented for identifying KCP-like proteins. Such methods entail, generally, searching a protein database with a pattern, selecting among the protein sequences identified or retrieved and, optionally, further characterizing the selected protein or proteins as KCP-like using other sequence analysis methods, or using biological assays such as have been described previously herein.

As used herein, "searching" refers to comparing an amino acid sequence pattern with a database of amino acid sequences. Such searches may be performed with a variety of well-known techniques, such as those presented in Example 7 of the Experimental section. For example, searching may be performed utilizing PHI-BLAST or PHI-PSI-BLAST under parameters comprising a default Expectation value (E) of 10, a gap opening cost with a default value of 11, and a gap extension cost with a default value of 1, or, additionally, with BLOSUM62 substitution matrix.

"Pattern" refers to an amino acid consensus sequence pattern, as exemplified by SEQ ID NO:97 and SEQ ID NO:98. "Database" refers to a protein database such as would be well-known to one of ordinary skill, and includes a database of amino acid sequences obtained from protein sequencing as well as presumptive protein sequences obtained by in silico translation of nucleotide sequences. "Selecting," as used herein refers to choosing one or more of the proteins obtained in the search which contain the pattern of interest. As used herein, "further characterizing" refers to further analysis of a selected sequence, which the skilled artisan would know would include a variety of methods, including both computer methods to look for other sequence characteristics indicative of a KCP-like protein, or biological methods, such as assaying the protein corresponding to the identified sequence for KCP-like activity. Such assays have been described elsewhere herein.

An exemplar of a method for identifying a KCP-like protein is a method for identifying KCP-like proteins, said method comprising: (a) searching at least one protein database with a pattern selected from the group consisting of: i) a pattern representing a compound having the formula (SEQ ID NO:97) C-X(2)-C-C-X(2)-[CS]-X(1,2)-C-V-P-[PSATK]-[GR]-X(2)-[GAQR], wherein: C is cysteine; X(2) is any two amino acids selected independently from one another; [CS] is one amino acid selected from the group consisting of cysteine and serine; X(1,2) is X(1) or X(2) wherein X(1) is any one amino acid, and X(2) is any two amino acids selected independently from one another; V is valine; P is proline; [PSATK] is one amino acid selected from the group consisting of proline, serine, alanine, threonine, and lysine; [GR] is one amino acid selected from the group consisting of glycine and arginine; and [GAQR] is one amino acid selected from the group consisting of glycine, alanine, glutamine and arginine; and ii) a pattern for a compound having the formula (SEQ ID NO:98) [CS]-[PSQAG]-X(0,2)-C-Y-X(4)-[TNSM]-X(5,8)-K, wherein [CS] is one amino acid selected from the group consisting of cysteine and serine; [PSQAG] is one amino acid selected from the group consisting of proline, serine, glutamine, alanine, and glycine; X(0,2) is X(0) or X(1) or X(2) wherein X(0) is no amino acid, X(1) is any one amino acid, and X(2) is any two amino acids selected independently from one another; C is cysteine; Y is tyrosine; X(4) is any four amino acids selected independently from one another;

[TNSM] is one amino acid selected from the group consisting of threonine, asparagine, serine, and methionine; X(5,8) is X(5) or X(6) or X(7) or X(8) wherein X(5) is any five amino acids selected independently from one another, X(6) is any six amino acids selected independently from one another, X(7) is any seven amino acids selected independently from one another, and X(8) is any eight amino acids selected independently from one another; and K is lysine; and (b) selecting among retrieved proteins at least one protein comprising at least one amino acid sequence represented by at least one formula selected from said group.

The invention also contemplates a computer device capable of implementing the aforementioned methods, and a system for implementing the methods. Specifically the invention contemplates a computer device comprising a processing portion capable of searching at least one protein database with a pattern, and a processing portion capable of selecting among retrieved proteins at least one protein comprising at least one amino acid sequence represented by at least one formula selected from said group. Optionally, this computer device may also include a processing portion for further characterizing the selected protein. The skilled artisan would be familiar with the meaning of the terms "computer device" and "processing portion" as used in the preceding description.

As a specific example of the preceding discussion, the present invention is directed to a computer device capable of implementing a method for identifying KCP-like proteins, said computer device comprising: (a) a processing portion capable of searching at least one protein database with a pattern selected from the group consisting of: i) a pattern representing a compound having the formula (SEQ ID NO:97) C-X(2)-C-C-X(2)-[CS]-X(1,2)-C-V-P-[PSATK]-[GR]-X(2)-[GAQR], wherein: C is cysteine; X(2) is any two amino acids selected independently from one another; [CS] is one amino acid selected from the group consisting of cysteine and serine; X(1,2) is X(1) or X(2) wherein X(1) is any one amino acid, and X(2) is any two amino acids selected independently from one another; V is valine; P is proline; [PSATK] is one amino acid selected from the group consisting of proline, serine, alanine, threonine, and lysine; [GR] is one amino acid selected from the group consisting of glycine and arginine; and [GAQR] is one amino acid selected from the group consisting of glycine, alanine, glutamine and arginine; and ii) a pattern for a compound having the formula (SEQ ID NO:98) [CS]-[PSQAG]-X(0,2)—C—Y-X(4)-[TNSM]-X(5,8)-K, wherein [CS] is one amino acid selected from the group consisting of cysteine and serine; [PSQAG] is one amino acid selected from the group consisting of proline, serine, glutamine, alanine, and glycine; X(0,2) is X(0) or X(1) or X(2) wherein X(0) is no amino acid, X(1) is any one amino acid, and X(2) is any two amino acids selected independently from one another; C is cysteine; Y is tyrosine; X(4) is any four amino acids selected independently from one another; [TNSM] is one amino acid selected from the group consisting of threonine, asparagine, serine, and methionine; X(5,8) is X(5) or X(6) or X(7) or X(8) wherein X(5) is any five amino acids selected independently from one another, X(6) is any six amino acids selected independently from one another, X(7) is any seven amino acids selected independently from one another, and X(8) is any eight amino acids selected independently from one another; and K is lysine; and (b) a processing portion capable of selecting among retrieved proteins at least one protein comprising at least one amino acid sequence represented by at least one formula selected from said group.

The present invention is also directed to a system for implementing the preceding methods, said system comprising: a reference protein database; and a computer device in communication with the reference protein database and comprising a processing portion capable of searching at least one protein database with a pattern, and a processing portion capable of selecting among retrieved proteins at least one protein comprising at least one amino acid sequence represented by at least one formula selected from said group. Optionally, the computer device in this system may also include a processing portion for further characterizing the selected protein. The skilled artisan would be familiar with the meaning of the term "reference protein database," examples of which are presented elsewhere herein. An example of such a system is one for implementing a method for identifying KCP-like proteins, said system comprising: a reference protein database; and a computer device in communication with the reference protein database and comprising: (a) a processing portion capable of searching at least one protein database with a pattern selected from the group consisting of: i) a pattern representing a compound having the formula (SEQ ID NO:97) C-X(2)-C-C-X(2)-[CS]-X(1,2)-C-V-P-[PSATK]-[GR]-X(2)-[GAQR], wherein: C is cysteine; X(2) is any two amino acids selected independently from one another; [CS] is one amino acid selected from the group consisting of cysteine and serine; X(1,2) is X(1) or X(2) wherein X(1) is any one amino acid, and X(2) is any two amino acids selected independently from one another; V is valine; P is proline; [PSATK] is one amino acid selected from the group consisting of proline, serine, alanine, threonine, and lysine; [GR] is one amino acid selected from the group consisting of glycine and arginine; and [GAQR] is one amino acid selected from the group consisting of glycine, alanine, glutamine and arginine; and ii) a pattern for a compound having the formula (SEQ ID NO:98) [CS]-[PSQAG]-X(0,2)—C—Y-X(4)-[TNSM]-X(5,8)-K, wherein [CS] is one amino acid selected from the group consisting of cysteine and serine; [PSQAG] is one amino acid selected from the group consisting of proline, serine, glutamine, alanine, and glycine; X(0,2) is X(0) or X(1) or X(2) wherein X(0) is no amino acid, X(1) is any one amino acid, and X(2) is any two amino acids selected independently from one another; C is cysteine; Y is tyrosine; X(4) is any four amino acids selected independently from one another; [TNSM] is one amino acid selected from the group consisting of threonine, asparagine, serine, and methionine; X(5,8) is X(5) or X(6) or X(7) or X(8) wherein X(5) is any five amino acids selected independently from one another, X(6) is any six amino acids selected independently from one another, X(7) is any seven amino acids selected independently from one another, and X(8) is any eight amino acids selected independently from one another; and K is lysine; and (b) a processing portion capable of selecting among retrieved proteins at least one protein comprising at least one amino acid sequence represented by at least one formula selected from said group.

Further, the present invention is directed to a method for identifying a member of a family of polypeptides, said method comprising: (a) aligning a reference dataset consisting of preselected members of said family; (b) determining a consensus sequence pattern that identifies all said preselected members; (c) searching at least one protein database with said consensus sequence pattern; (d) selecting among retrieved proteins at least one protein comprising at least one amino acid sequence represented by said pattern; and (e) identifying the selected protein as a member of said family.

Other methods contemplated by the present invention include a computer device capable of implementing a method for identifying a member of a family of polypeptides, said computer device comprising: (a) a processing portion capable of aligning a reference dataset consisting of preselected members of said family; (b) a processing portion capable of determining a consensus sequence pattern that identifies all said preselected members; (c) a processing portion capable of searching at least one protein database with said consensus sequence pattern; (d) a processing portion capable of selecting among retrieved proteins at least one protein comprising at least one amino acid sequence represented by said pattern; and (e) a processing portion capable of identifying the selected protein as a member of said family.

Another contemplated method of the present invention is directed to a system for implementing a method for identifying a member of a family of polypeptides, said system comprising: a reference dataset; and a computer device in communication with the reference dataset and comprising: (a) a processing portion capable of aligning said reference dataset consisting of preselected members of said family; (b) a processing portion capable of determining a consensus sequence pattern that identifies all said preselected members; (c) a processing portion capable of searching at least one protein database with said consensus sequence pattern; (d) a processing portion capable of selecting among retrieved proteins at least one protein comprising at least one amino acid sequence represented by said pattern; and (e) a processing portion capable of identifying the selected protein as a member of said family.

Although the present invention has been described in some detail by way of illustration and example for purposes of clarity of understanding, it will be obvious that certain changes and modifications may be practiced within the scope of the appended claims.

The following examples are offered by way of illustration and not by way of limitation.

EXPERIMENTAL

Example 1

Transformation and Regeneration of Transgenic Plants

Immature maize embryos from greenhouse donor plants are bombarded with a plasmid containing a KCP-like nucleotide sequence operably linked to a ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the KCP-like gene operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension while vortexing is maintained on the multitube vortexer. The final mixture is sonicated briefly and allowed to incubate under constant vortexing for 10 minutes. After the precipitation period, the tubes are centrifuged briefly, liquid is removed, and the pellet is washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 psi, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of KCP-like protein. Assays to monitor expression of KCP-like sequences include, for example, Northern and Western analysis and phenotypic assays including enhanced disease resistance.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 2

Soybean Embryo Transformation

Soybean embryos are bombarded with a plasmid containing a KCP-like nucleic acid operably linked to an ubiquitin promoter as follows. To induce somatic embryos, cotyledons 3-5 mm in length are dissected from surface-sterilized, immature seeds of the soybean cultivar A2872 and cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml of liquid media on a rotary shaker at 150 rpm and 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) Nature 327:70-73); U.S. Pat. No. 4,945,050). A DuPont Biolistic PDS1000/HE instrument (helium retrofit) can be used for these transformations.

A selectable marker gene that can be used to facilitate soybean transformation is a transgene composed of the $^{35}S$ promoter from Cauliflower Mosaic Virus (Odell et al. (1985) Nature 313:810-812), the hygromycin phosphotransferase gene from plasmid pJR225 (from E. coli; Gritz et al. (1983) Gene 25:179-188), and the 3' region of the nopaline synthase gene from the T-DNA of the Agrobacterium tumefaciens Ti plasmid. The expression cassette comprising the KCP-like sequence operably linked to the promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macrocarrier disk.

Approximately 300-400 mg of a two-week-old suspension culture is placed in an empty 60×15 mm Petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 3

*Agrobacterium*-Mediated TRANSFORMATION

For *Agrobacterium*-mediated transformation of maize with KCP-like genes or nucleotide sequences of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the KCP-like genes or nucleotide sequences of interest to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 4

Construction of the cDNA Libraries

Total RNA was isolated from corn tissues with TRIzol Reagent (Life Technology Inc. Gaithersburg, Md.) using a modification of the guanidine isothiocyanate/acid-phenol procedure described by Chomczynski and Sacchi (1987) Anal. Biochem. 162:156. In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. Total RNA was recovered by precipitation with isopropyl alcohol from the aqueous phase.

The selection of poly(A)+ RNA from total RNA was performed using PolyATact system (Promega Corporation, Madison Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed in highly stringent conditions and eluted with RNase-free deionized water.

cDNA synthesis was performed and unidirectional cDNA libraries were constructed using the SuperScript Plasmid System (Life Technology, Inc., Gaithersburg, Md.). The first strand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adaptors were removed by Sephacryl-5400 chromatography. The selected cDNA molecules were ligated into a pSPORT1 vector between the NotI and SalI sites.

Example 5 cDNA Sequencing and Library Subtraction

Individual colonies were picked and DNA was prepared either by PCR with M13 forward primers and M13 reverse primers, or by plasmid isolation. All the cDNA clones were sequenced using M13 reverse primers.

cDNA libraries subjected to the subtraction procedure were plated out on 22×22 cm$^2$ agar plate at density of about 3,000 colonies per plate. The plates were incubated in a 37° C. incubator for 12-24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of each filter was placed into Proteinase K solution and incubated at 37° C. for 40-50 minutes. The filters were placed on dry filter papers to dry overnight. DNA was then cross-linked to the nylon membrane by UV light treatment.

Colony hybridization was conducted as described by Sambrook, Fritsch, and Maniatis (in Molecular Cloning: A Laboratory Manual, 2$^{nd}$ Edition). The following probes were used in colony hybridization:

1. First strand cDNA from the same tissue as that from which the library was made in order to identify and remove the most redundant clones.
2. 48-192 most redundant cDNA clones from the same library based on previous sequencing data.
3. 192 most redundant cDNA clones in the entire corn sequence database.
4. A Sal-A20 oligo nucleotide TCG ACC CAC GCG TCC GAA AAA AAA AAA AAA AAA AAA (set forth in SEQ ID NO:99), which can be used to identify and remove clones containing a poly A tail but no cDNA.
5. cDNA clones derived from rRNA.

The image of the autoradiography was scanned into an analysis computer and the signal intensity and "cold colony" addresses of each colony was analyzed. Re-arraying of cold colonies from 384 well plates to 96 well plates was conducted using Q-bot.

Example 6

Identification of the Gene from a Computer Homology Search

Gene identities can be determined by conducting BLAST searches (Basic Local Alignment Search Tool; Altschul et al. (1993) *J. Mol. Biol.* 215:403-410; see also the National Center for Biotechnology Information site located on the world wide web: ncbi.nlm.nih.gov/BLAST/) under default parameters for similarity to sequences contained in the BLAST "nr" database. The publicly-available NCBI nr database comprises all non-redundant GenBank CDS translations, sequences derived from the 3-dimensional structure Brookhaven Protein Data Bank, the last major release of the SWISS-PROT protein sequence database, and the EMBL and DDBJ databases. The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish and States (1993) *Nature Genetics* 3:266-272). In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the CLUSTAL method of alignment (Higgins and Sharp (1989) *CABIOS* 5:151-153) with default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

A search of publicly available databases revealed that a petunia sequence (Q43615) shares 54% identity and 63% similarity with the Zm-KCP1 predicted peptide, and a cotton sequence (W15751) shares 44% identity and 52% similarity with the Zm-KCP1 predicted peptide.

Example 7

Computer-Implemented Methods, and Consensus Patterns (Regular Expressions) that Specifically Identify KCP Gene Family Members As set forth above, the invention encompasses the discovery and analysis of 36 crop plant genes in the KCP family, which are related to the potato antimicrobial peptide snakin. The invention additionally provides computer-implemented methods, and two amino acid consensus sequence patterns (regular expressions 1 and 2) that specifically identify KCP-like gene family members. Thus, these regular expressions are useful for identifying a subset of KCP related proteins that are within the family of the KCP-like proteins of the invention.

Regular expression 1 has the amino acid sequence consensus pattern: C-x(2)-C-C-x(2)-[CS]-x(1,2)-C-V-P-[PSATK]-[GR]-x(2)-[GAQR] (SEQ ID NO:97). The notation of this expression follows a standard protocol (Bairoch (1991) *Nucleic Acids Research.* 19:2241-2245) and designates the following sequence pattern: cysteine--two amino acids of any type--cysteine--cysteine--two amino acids of any type--cysteine or serine--one or two amino acids of any type--cysteine--valine--proline--proline or serine or alanine or threonine or lysine--glycine or arginine--two amino acids of any type--glycine or alanine or glutamine or arginine.

Regular expression 2 has the amino acid sequence consensus pattern: [CS]PSQAG]-x(0,2)-C-Y-x(4)-[TNSM]-x(5, 8)-K (SEQ ID NO:98). This notation of this expression also follows the protocol referred to above, and designates the following sequence pattern: cysteine or serine--proline or serine or glutamine or alanine or glycine--zero or one or two amino acids of any type--cysteine--tyrosine--four amino acids of any type--threonine or asparagine or serine or methionine--five or six or seven or eight amino acids of any type--lysine.

KCP-Like Reference Dataset:

A reference dataset of KCP-like polypeptide sequences was constructed to test the effectiveness of various candidate regular expressions in identifying KCP-like proteins. This reference dataset consisted of the KCP-like polypeptides of the invention set forth in SEQ ID NO:37-72, a KCP polypeptide set forth in SEQ ID NO:73 a novel KCP-like polypeptide (sequence not shown), as well as a set of KCP-like polypeptides identified from public databases by a combination of BLAST and PSI-BLAST. The set of KCP-like polypeptides identified from public databases correspond to those identified in TABLE 1 and set forth in SEQ ID NOS:74-96 respectively.

TABLE 1

AF014396, Potato snakin-1.
gi_5102600 _emb_CAB45241.1_ (AJ005206) GEG protein [*Gerbera hybrida*].
gi_6539267 _gb_AAF15937.1_AC011765_33 (AC011765) GAST1-like protein [*Arabidopsis thaliana*].
gi_405585 gb_AAA20129.1_ RSI-1 protein [*Solanum lycopersicum*]
gi_405587_gb_AAA20130.1_ RSI-1 protein [*Solanum lycopersicum*] pir_S43910_S43910 gibberellin-regulated protein RSI-1 precursor - tomato sp_P47926_RSI1_LYCES RSI-1 Protein precursor (TR132).
gi_2764941 emb_CAA66909.1_ transcriptionally stimulated by gibberellins expressed in meristematic region, and style [*Arabidopsis thaliana*] sp_O49593_O49593 GASA4 GENE.
gi_950099 gb_AAA74480.1_ gibberellin-regulated [*Arabidopsis thaliana*]
sp_P46690_GAS4_ARATH gibberellin-regulated protein 4 precursor.
gi_1289320 gb_AAA98520.1_ GASA5 [*Arabidopsis thaliana*] pir_S71371_S71371 gibberellin-regulated protein GASA5 precursor - *Arabidopsis thaliana* sp_Q38939_Q38939 GASA5.
gi_19247 emb_CAA44807.1_ gast1 [*Lycopersicon esculentum*] pir_S22151_S22151 gibberellin-regulated protein GAST1 - tomato sp_P27057_GST1_LYCES GAST1 protein precursor.
gi_887935 gb_AAB06308.1_ GAST1 protein homolog [*Arabidopsis thaliana*] pir_S60231_S60231 gibberellin-regulated protein GASA3 precursor - *Arabidopsis thaliana* sp_P46687_GAS3_ARATH Gibberellin-regulated protein 3 precursor.
gi_887937 gb_AAB06309.1_ GAST1 protein homolog [*Arabidopsis thaliana*] pir_S60230_S60230 gibberellin-regulated protein GASA2 precursor - *Arabidopsis thaliana* sp_P46688_GAS2_ARATH gibberellin-regulated protein 2 precursor.
gi_887939 gb_AAB06310.1_ GAST1 protein homolog [*Arabidopsis thaliana*]
sp_P46689_GAS1_ARATH gibberellin-regulated protein 1 precursor.
gi_825524 emb_CAA60677.1_ gip1 [*Petunia* x *hybrida*]pir_S54832_S54832 gip1 protein - garden petunia sp_Q43615_Q43615 GIP1 protein.
gi_2253442 gb_AAB62947.1_ (AF007784) LTCOR11 [*Lavatera thuringiaca*]
sp_O24040_O24040 LTCOR11.
gi_2792297 gb_AAB97006.1_ (AF039183) GAST-like gene product [*Fragaria* x *ananassa*]
sp_O49134_O49134 GAST-like gene product.
gi_3094012 gb_AAC15460.1_ (AF060569) cold-regulated LTCOR12 [*Lavatera thuringiaca*]
sp_O65313_O65313 cold-regulated LTCOR12.
gi_3201610 gb_AAC20716.1_ (AC004669) unknown protein [*Arabidopsis thaliana*]
sp_O80848_O80848 F7F1.2 protein.
gi_3355483 gb_AAC27845.1_ (AC004218) gibberellin-regulated protein (GASA5)-like [*Arabidopsis thaliana*] pir_T00564_T00564 gibberellin-regulated protein (GASA5)-like protein - *Arabidopsis thaliana* sp_080641_080641 gibberellin-regulated protein (GASA5)-like.
gi_2982285 gb_AAC32128.1_ (AF051227) GASA5-like protein [*Picea mariana*]
sp_065066_065066 GASA5-like protein.
gi_3650032 gb_AAC61287.1_ (AC005396) gibberellin-regulated protein GAST1-like [*Arabidopsis thaliana*] sp_082328_082328 gibberellin-regulated protein GAST1-like.
gi_4309725 gb_AAD15495.1_ (AC006439) putative gibberellin-regulated protein [*Arabidopsis thaliana*] sp_AAD15495_AAD15495 Putative gibberellin-regulated protein.
pir_S60229 S60229 gibberellin-regulated protein GASA1 precursor - *Arabidopsis thaliana*.
pir_JE0159 JE0159 gibberellin-stimulated transcript 1 like protein - rice.
pir_S60232 S60232 gibberellin-regulated protein GASA4 precursor - *Arabidopsis thaliana*.

Alignments and Generation of Regular Expressions:

All available KCP related predicted amino acid sequences were multiply aligned using AlignX (Vector NTI Suite 5.5, Informax Inc.) which is based on the ClustalW algorithm (Thompson et al. (1994) *Nucleic Acids Research* 22: 4673-4680). The conserved amino acids revealed by the alignment describe regular expressions shared by the entire gene family. Twelve conserved cysteines which are prominent conserved features of KCP related proteins were included in many of these regular expressions that were designed and tested.

Testing Regular Expressions for Effectiveness Using PHI-Blast and PSI-Blast:

The method employed for identifying all the KCP sequences was either PHI-BLAST (Pattern Hit Initiated BLAST) or a combination of PHI-BLAST and PSI-BLAST (Position Specific Iteration Blast). See Zhang et al. (1998) *Nucleic Acids Research* 26: 3986-3990. When both PHI-BLAST and PSI-BLAST were used in combination, the search was done in two rounds, with the first round using PHI-BLAST, and the second round using PSI-BLAST (PHI-PSI-BLAST). The BLOSUM62 substitution matrix was used, as was the default Expectation value (E) of 10. Cost for opening gaps was used with the default value of 11, and the cost to extend a gap was also used with the default value of 1.

In order to run the PHI-BLAST, PSI-BLAST, or the PHI-PSI-BLAST tandem routine, a designated query sequence was required. The initial default query sequence used to test various candidate regular expressions was Zm-KCP1. For those regular expressions showing promise, the routine was repeated with at least three other query sequences, namely Os-KCP1, Ta-KCP1 and Gm-KCP1, that represent breadth and diversity in the KCP-like protein family. Repeating the routine with the additional sequences indicated that the result for a regular expression was independent of the KCP-like query sequence used.

For testing the effectiveness of the regular expressions, the reference dataset stated above was used. The goal was to find a regular expression that could identify all the sequences in this reference dataset, given the parameters of PHI-BLAST or the PHI-PSI-BLAST tandem routine defined above.

In this manner, multiple regular expressions were designed and considered. Two regular expressions were found to identify all the sequences in the reference dataset using either PHI-BLAST or PHI-PSI-BLAST. These were regular expressions 1 and 2 given elsewhere herein and set forth in SEQ ID NO:97 and SEQ ID NO:98, respectively. One embodiment of regular expression 1 corresponds to amino acid positions 77 to 93 of default query sequence Zm-KCP1 (SEQ ID NO:37). One embodiment of regular expression 2 corresponds to amino acid positions 98 to 112 of default query sequence Zm-KCP1 (SEQ ID NO:37). In order to test the consistancy of the KCP regular expressions 1 and 2 and identify all members of the KCP-like protein family in the reference dataset, three additional "query" sequences were used in addition to Zm-KCP1 (SEQ ID NO:37); namely Gm-KCP1, accession NO. JE 0159, and Ta-KCP1 (SEQ ID NOS:55, 95, and 46). Using each of these query sequences by the same methods stated above, regular expressions 1 and 2 were both able to identify all of the KCP-like proteins in the reference dataset.

Subsequently, regular expressions 1 and 2 were tested against an open field dataset, namely the public NR (nonredundant) database. Using either PHI-BLAST or PHI-PSI-BLAST, regular expression 1 was able to identify 22 of the 23 of the above publicly known KCP-like sequences set forth in TABLE 1, when used with the four different query KCP-like sequences (SEQ ID NOS:37, 46, 55 and 95). It is noted that, when using PHI-BLAST, this regular expression did not identify non-KCP sequences; and identified only the 22 KCP sequences (See appendix I for the output). However, when PHI-PSI-BLAST was used, the entire 23/23 publicly known KCP-like sequences (TABLE 1) were identified. In this manner, tandem PHI-PSI-BLAST is more effective that PHI-BLAST alone for utilizing regular expression 1. Using tandem PHI-PSI-BLAST, additional sequences were also identified with E values below the threshold of 10. These other sequences included distintigrins, mucins, and metallothioproteinases, but not the hemolytic protein kistrin. It should be noted however that their E value scores were markedly less significant than any of the 23 core public KCP-like sequences of TABLE 1. The least significant E value score from the PSI-BLAST portion was 1e-17, and the most significant non-KCP E value score was 0.014 (see appendix II for output). This wide range in the output E value scores indicates that by using PHI-PSI-BLAST as described and in conjunction with regular expression 1, all or nearly all members of the KCP-like family can be identified to the exclusion of non-members of this family.

For KCP regular expression 2, both PHI-BLAST and tandem PHI-PSI-BLAST identifies all 23 of the public KCP-like genes. Initially, a regular expression was designed which was identical to that set forth above, and in SEQ ID NO:98, for regular expression 2, with the exception that a -[TNS]- position was used in place of a -[TNSM]-position. This initial version of regular expression 2 identified all 23 of the public KCP-like genes in the reference dataset. For tandem PHI-PSI-BLAST, the gulf in E value scores between the output E value scores was also large. The least significant KCP E value score from the PSI-BLAST portion was 1e-18, and the most significant non-KCP E value score was 0.003. See appendices III and IV for outputs.

However, Ta-KCP1 sequence of the invention (SEQ ID NO:46) did not exactly match this initial KCP regular expression 2. This Ta-KCP1 sequence had a methionine at the corresponding -[TNS]- position. Inclusion of methionine as an option at this position does allow for identification of Ta-KCP1 by regular expression 2 set forth above, and in SEQ ID NO:98. Thus, both KCP regular expressions 1 and 2 employed with the methods described here are specific identifiers of members of the KCP gene family. Numerous other regular expressions; including those designed based on twelve conserved cysteines and those including terminal lysine, cysteine, and proline residues. These other regular expressions failed to identify all of the KCP-like sequences in the reference dataset.

Therefore, it was concluded that KCP regular expressions 1 and 2 are useful for identifying KCP-like protein family members using tandem PHI-PSI-BLAST. These regular expressions can be used alone or in combination to effect a complete or near complete identification of members of KCP-like family of proteins.

The methods of the present invention could be used to identify members of any family of proteins. That is, the methods of the invention can be used to align a reference dataset consisting of known or preselected members of a family, determining a consensus sequence pattern that identifies all of the known or preselected members, searching at least one protein database with this consensus sequence pattern, selecting among the retrieved proteins at least one protein comprising at least one amino acid sequence represented by the pattern; and identifying the selected protein as a member of this family.

Furthermore, in this manner, the methods of the present invention can be used to identify one or more subsets of a known family, wherein the subset consists of members the family that are identified by a consensus sequence that identifies all members of the subset and excludes other members of the family.

APPENDIX I

Output of PHI-BLAST search versus NR database using KCP Regular Expression 1.

BLASTP 2.0.9
Reference: Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs", Nucleic Acids Res. 25: 3389-3402.
Query = Zm-KCP1, p0118.chsbd73r, FL, Zea mays, proofed     (114 letters)
Database: nr     485,275 sequences; 152,116,570 total letters
Searching
1 occurrence(s) of pattern in query
   Pattern for KCP identification
   pattern C-x(2)-C-C-x(2)-[CS]-x(1,2)-C-V-P-[PSATK]-[GR]-x(2)-[GAQR]
   at position 77 of query sequence
effective database length = 1.4e+08
   pattern probability = 3.8e-13
   length × probability = 5.5e-05
. . . . . . . . . . . . . . . . . . . . . . . . . . . . . . . . . . . .
Number of occurrences of pattern in the database is 22
done

| | Score (bits) | E Value |
|---|---|---|
| Significant matches for pattern occurrence 1 at position 77 | | |
| pir\|\|S54832   gip1 protein - garden *petunia* >gi\|825524\|emb\|CAA606 . . . | 82 | 4e-24 |
| sp\|P27057\|GST1__LYCES   GAST1 PROTEIN PRECURSOR >gi\|100217\|pir\|\|S2 . . . | 79 | 3e-23 |
| pir\|\|S71371   gibberellin-regulated protein GASA5 - *Arabidopsis t* . . . | 75 | 6e-22 |
| emb\|CAA66909.1\|   (X98255) transcriptionally stimulated by gibber . . . | 74 | 2e-21 |
| pir\|\|S60232   GAST1 protein homolog (clone GASA4) - *Arabidopsis t* . . . | 74 | 2e-21 |
| sp\|P46690\|GAS4__ARATH   GIBBERELLIN-REGULATED PROTEIN 4 PRECURSOR . . . | 74 | 2e-21 |
| gb\|AAC32128.1\|   (AF051227) GASA5-like protein [*Picea mariana*] | 72 | 5e-21 |
| gb\|AAF15937.1\|AC011765__33   (AC011765)   GAST1-like protein [*Arabid* . . . | 70 | 1e-20 |
| gb\|AAC20716.1\|   AC004669 putative gibberellinregulated protei . . . | 70 | 2e-20 |
| sp\|P47926\|RSI1__LYCES   RSI-1 PROTEIN PRECURSOR (TR132) >gi\|107659 . . . | 69 | 4e-20 |
| gb\|AAC32170.1\|   (AF051753) GASA5-like protein [*Picea mariana*] >g . . . | 66 | 3e-19 |
| gb\|AAC61287.1\|   AC005396 similar to gibberellinregulated prot . . . | 46 | 2e-13 |
| gb\|AAC27845.1\|   AC004218 similar to gibberellinregulated prot . . . | 44 | 1e-12 |
| sp\|P46688\|GAS2__ARATH   GIBBERELLIN-REGULATED PROTEIN 2 PRECURSOR . . . | 38 | 9e-11 |
| sp\|P46687\|GAS3__ARATH   GIBBERELLIN-REGULATED PROTEIN 3 PRECURSOR . . . | 37 | 2e-10 |
| emb\|CAB45241.1\|   (AJ005206) GEG protein [*Gerbera hybrida*] | 31 | 8e-09 |
| gb\|AAB62947.1\|   AF007784 LTCOR11 [*Lavatera thuringiaca*] | 30 | 2e-08 |
| gb\|AAC15460.1\|   (AF060569) cold-regulated LTCOR12 [*Lavatera thur* . . . | 30 | 2e-08 |
| gb\|AAB97006.1\|   (AF039183) GAST-like gene product [*Fragaria* x an . . . | 28 | 6e-08 |
| gb\|AAD01518.1\|   (AF014396) Snakin-1 [*Solanum tuberosum*] | 28 | 6e-08 |
| pir\|\|S60229   GAST1 protein homolog (clone GASA1) - *Arabidopsis t* . . . | 27 | 2e-07 |
| sp\|P46689\|GAS1__ARATH   GIBBERELLIN-REGULATED PROTEIN 1 PRECURSOR . . . | 27 | 2e-07 |
| Significant alignments for pattern occurrence 1 at position 77 | | |

APPENDIX II

Output of tandem PHI-PSI-BLAST search versus NR database.

PHI-Blast Round Output

BLASTP 2.0.9
Reference: Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs", Nucleic Acids Res. 25: 3389-3402.
Query = Zm-KCP1, p0118.chsbd73r, FL, *Zea mays*, proofed     (114 letters)
Database: nr     485,275 sequences; 152,116,570 total letters
Searching 1 occurrence(s) of pattern in query
   Pattern for KCP identification
   pattern C-x(2)-C-C-x(2)-[CS]-x(1,2)-C-V-P-[PSATK]-[GR]-x(2)-[GAQR]
   at position 77 of query sequence
effective database length = 1.4e+08
   pattern probability = 3.8e-13
   length × probability = 5.5e-05
. . . . . . . . . . . . . . . . . . . . . . . . . . . . . . . . . . . .
Number of occurrences of pattern in the database is 22
Done

APPENDIX II-continued

Output of tandem PHI-PSI-BLAST search versus NR database.

Results from round 1

| | Score (bits) | E Value |
|---|---|---|
| Significant matches for pattern occurrence 1 at position 77 | | |
| pir\|\|S54832  gip1 protein - garden *petunia* >gi\|825524\|emb\|CAA606 . . . | 82 | 4e−24 |
| sp\|P27057\|GST1__LYCES  GAST1 PROTEIN PRECURSOR >gi\|100217\|pir\|\|S2 . . . | 79 | 3e−23 |
| pir\|\|S71371  gibberellin-regulated protein GASA5 - *Arabidopsis t* . . . | 75 | 6e−22 |
| emb\|CAA66909.1\|  (X98255) transcriptionally stimulated by gibber . . . | 74 | 2e−21 |
| pir\|\|S60232  GAST1 protein homolog (clone GASA4) - *Arabidopsis t* . . . | 74 | 2e−21 |
| sp\|P46690\|GAS4__ARATH  GIBBERELLIN-REGULATED PROTEIN 4 PRECURSOR . . . | 74 | 2e−21 |
| gb\|AAC32128.1\|  (AF051227) GASA5-like protein [*Picea mariana*] | 72 | 5e−21 |
| gb\|AAF15937.1\|AC011765__33  (AC011765) GAST1-like protein [*Arabid* . . . | 70 | 1e−20 |
| gb\|AAC20716.1\|  (AC004669) putative gibberellin-regulated protei . . . | 70 | 2e−20 |
| sp\|P47926\|RSI1__LYCES  RSI-1 PROTEIN PRECURSOR (TR132) >gi\|107659 . . . | 69 | 4e−20 |
| gb\|AAC32170.1\|  (AF051753) GASA5-like protein [*Picea mariana*] >g . . . | 66 | 3e−19 |
| gb\|AAC61287.1\|  (AC005396) similar to gibberellin-regulated prot . . . | 46 | 2e−13 |
| gb\|AAC27845.1\|  (AC004218) similar to gibberellin-regulated prot . . . | 44 | 1e−12 |
| sp\|P46688\|GAS2__ARATH  GIBBERELLIN-REGULATED PROTEIN 2 PRECURSOR . . . | 38 | 9e−11 |
| sp\|P46687\|GAS3__ARATH  GIBBERELLIN-REGULATED PROTEIN 3 PRECURSOR . . . | 37 | 2e−10 |
| emb\|CAB45241.1\|  (AJ005206) GEG protein [*Gerbera hybrida*] | 31 | 8e−09 |
| gb\|AAB62947.1\|  (AF007784) LTCOR11 [*Lavatera thuringiaca*] | 30 | 2e−08 |
| gb\|AAC15460.1\|  (AF060569) cold-regulated LTCOR12 [*Lavatera thur* . . . | 30 | 2e−08 |
| gb\|AAB97006.1\|  (AF039183) GAST-like gene product [*Fragaria* x an . . . | 28 | 6e−08 |
| gb\|AAD01518.1\|  (AF014396) Snakin-1 [*Solanum tuberosum*] | 28 | 6e−08 |
| pir\|\|S60229  GAST1 protein homolog (clone GASA1) - *Arabidopsis t* . . . | 27 | 2e−07 |
| sp\|P46689\|GAS1__ARATH  GIBBERELLIN-REGULATED PROTEIN 1 PRECURSOR . . . | 27 | 2e−07 |
| Significant alignments for pattern occurrence 1 at position 77 | | |

PSI-Blast Round Output

Searching . . . done
Results from round 2 - Using PSI-BLAST based on the PHI-Blast output

| | Score (bits) | E Value |
|---|---|---|
| Sequences producing significant alignments: | | |
| Sequences used in model and found again: | | |
| pir\|\|S54832  gip1 protein-garden *petunia* >gi\|825524\|emb\|CAA606 . . . | 156 | 5e−38 |
| gb\|AAC61287.1\|  (AC005396) similar to gibberellin-regulated prot . . . | 145 | 1e−34 |
| sp\|P27057\|GST1__LYCES  GAST1 PROTEIN PRECURSOR >gi\|100217\|pir\|\|S2 . . . | 139 | 1e−32 |
| gb\|AAC32128.1\|  (AF051227) GASA5-like protein [*Picea mariana*] | 132 | 1e−30 |
| gb\|AAF15937.1\|AC011765__33  (AC011765) GAST1-like protein [*Arabid* . . . | 131 | 3e−30 |
| gb\|AAC20716.1\|  (AC004669) putative gibberellin-regulated protei . . . | 130 | 5e−30 |
| pir\|\|S71371  gibberellin-regulated protein GASA5 - *Arabidopsis t* . . . | 130 | 7e−30 |
| gb\|AAC32170.1\|  (AF051753) GASA5-like protein [*Picea mariana*] >g . . . | 126 | 7e−29 |
| sp\|P47926\|RSI1__LYCES  RSI-1 PROTEIN PRECURSOR (TR132) >gi\|107659 . . . | 124 | 3e−28 |
| pir\|\|S60232  GAST1 protein homolog (clone GASA4) - *Arabidopsis t* . . . | 121 | 3e−27 |
| sp\|P46690\|GAS4__ARATH  GIBBERELLIN-REGULATED PROTEIN 4 PRECURSOR . . . | 120 | 4e−27 |
| emb\|CAA66909.1\|  (X98255) transcriptionally stimulated by gibber . . . | 120 | 4e−27 |
| gb\|AAB62947.1\|  (AF007784) LTCOR11 [*Lavatera thuringiaca*] | 115 | 2e−25 |
| gb\|AAB97006.1\|  (AF039183) GAST-like gene product [*Fragaria* x an . . . | 114 | 4e−25 |
| sp\|P46687\|GAS3__ARATH  GIBBERELLIN-REGULATED PROTEIN 3 PRECURSOR . . . | 113 | 7e−25 |
| gb\|AAC15460.1\|  (AF060569) cold-regulated LTCOR12 [*Lavatera thur* . . . | 112 | 9e−25 |
| sp\|P46688\|GAS2__ARATH  GIBBERELLIN-REGULATED PROTEIN 2 PRECURSOR . . . | 112 | 9e−25 |
| sp\|P46689\|GAS1__ARATH  GIBBERELLIN-REGULATED PROTEIN 1 PRECURSOR . . . | 112 | 1e−24 |
| pir\|\|S60229  GAST1 protein homolog (clone GASA1) - *Arabidopsis t* . . . | 112 | 1e−24 |
| emb\|CAB45241.1\|  (AJ005206) GEG protein [*Gerbera hybrida*] | 110 | 6e−24 |
| gb\|AAC27845.1\|  (AC004218) similar to gibberellin-regulated prot . . . | 109 | 1e−23 |
| gb\|AAD01518.1\|  (AF014396) Snakin-1 [*Solanum tuberosum*] | 90 | 1e−17 |
| Sequences not found previously or not previously below threshold: | | |
| gb\|AAD15495.1\|  (AC006439) similar to gibberellin-regulated prot . . . | 89 | 1e−17 |
| gb\|AAC67545.1\|  (AF086604) mucin [*Homo sapiens*] | 39 | 0.014 |
| emb\|CAA06167.1\|  (AJ004862) mucin [*Homo sapiens*] | 37 | 0.090 |
| gb\|AAB93766.1\|  (U66246) von Willebrand factor [*Canis familiaris*] | 36 | 0.15 |
| sp\|Q28295\|VWF__CANFA  VON WILLEBRAND FACTOR PRECURSOR >gi\|1478046 . . . | 36 | 0.15 |
| gb\|AAD04919.1\|  (AF099154) von Willebrand factor [*Canis familiaris*] | 36 | 0.15 |
| emb\|CAA70525.1\|  (Y09353) von Willebrand factor [*Bos taurus*] | 35 | 0.20 |
| gb\|AAC06229.1\|  (AF052036) von Willebrand factor precursor [*Sus* . . . | 35 | 0.20 |
| gb\|AAD39266.1\|AC007842__1  (AC007842) Human Fc gamma BP [AA 1-284 . . . | 35 | 0.27 |
| ref\|NP__003881.1\|\|  IgG Fc binding protein >gi\|1944352\|dbj\|BAA195 . . . | 35 | 0.27 |
| ref\|NP__031426.1\|\|  a disintegrin and metalloproteinase domain 12 . . . | 35 | 0.27 |
| gb\|AAB71835.1\|  (AF008583) metallothionein [*Ambystoma mexicanum*] | 35 | 0.27 |
| pir\|\|S38539  gene MDC protein - human >gi\|455835\|gb\|AAB29191.1\| . . . | 35 | 0.35 |
| ref\|NP__002381.2\|\|  metalloproteinase-like, disintegrin-like, cys . . . | 35 | 0.35 |

APPENDIX II-continued

Output of tandem PHI-PSI-BLAST search versus NR database.

| | | |
|---|---|---|
| pir\|\|I52965  disintegrin-like metalloproteinase (EC 3.4.24.—) - . . . | 35 | 0.35 |
| dbj\|BAA06670.1\|  (D31872) metalloprotease/disintegrin-like prote . . . | 35 | 0.35 |
| ref\|NP_033743.1\|\|  a disintegrin and metalloprotease domain (ADA . . . | 35 | 0.35 |
| prf\|\|1101271B  metallothionein MT Ipg [Homo sapiens] | 34 | 0.46 |
| pir\|\|S60258  meltrin beta - mouse (fragment) >gi\|1584289\|prf\|\|21 . . . | 34 | 0.46 |
| ref\|NP_002441.1\|\|  metallothionein 1L >gi\|462637\|sp\|P80297\|MT1L_ . . . | 34 | 0.46 |
| ref\|NP_033746.1\|\|  a disintegrin and metalloproteinase domain 19 . . . | 34 | 0.46 |
| sp\|P17816\|GRP_HORVU  GLYCINE-RICH CELL WALL STRUCTURAL PROTEIN P . . . | 34 | 0.46 |
| emb\|CAA07188.1\|  (AJ006692) ultra high sulfer keratin [Homo sapi . . . | 34 | 0.46 |
| dbj\|BAA18923.1\|  (D50410) meltrin beta [Mus musculus] | 34 | 0.46 |
| emb\|CAA09979.1\|  (AJ012287) alpha tectorin [Gallus gallus] | 34 | 0.60 |
| emb\|CAB04626.1\|  (Z81573) M02G9.3 [Caenorhabditis elegans] | 34 | 0.60 |
| ref\|NP_003465.1\|\|  Meltrin-alpha, mouse, homolog of >gi\|2677839\| . . . | 34 | 0.60 |
| pir\|\|S43534  integrin beta3 - chicken >gi\|474039\|emb\|CAA51069.1\| . . . | 34 | 0.60 |

Note:
There were additional hits of even less significance not shown here.

APPENDIX III

Output of PHI-BLAST search versus NR database using KCP Regular Expression 2.

BLASTP 2.0.9
Reference: Altschul, Stephen F., Thomas L. Madden, Alejandro A. Schäffer,
Jinghui Zhang, Zheng Zhang, Webb Miller, and David J. Lipman (1997), "Gapped BLAST
and PSI-BLAST: a new generation of protein database search programs", Nucleic Acids
Res. 25: 3389-3402.
Query = Zm-KCP1, p0118.chsbd73r, FL, Zea mays, proofed     (114 letters)
Database: nr     485,275 sequences; 152,116,570 total letters
Searching
1 occurrence(s) of pattern in query
    Pattern for KCP identification
    pattern [CS]-[PSQAG]-x(0,2)-C-Y-x(4)-[TNS]-x(5,8)-K
    at position 98 of query sequence
effective database length = 1.4e+08
    pattern probability = 1.0e−06length × probability = 1.5e+02
. . . . . . . . . . . . . . . . . . . . . . . . . . . . . . . . . . .
Number of occurrences of pattern in the database is 291
done

| | Score (bits) | E Value |
|---|---|---|
| Significant matches for pattern occurrence 1 at position 98 | | |
| emb\|CAA66909.1\|  (X98255) transcriptionally stimulated by gibber . . . | 80 | 2e-22 |
| pir\|\|S60232  GAST1 protein homolog (clone GASA4) - Arabidopsis t . . . | 80 | 2e-22 |
| sp\|P46690\|GAS4_ARATH  GIBBERELLIN-REGULATED PROTEIN 4 PRECURSOR . . . | 80 | 2e-22 |
| pir\|\|S54832  gip1 protein - garden petunia >gi\|825524\|emb\|CAA606 . . . | 79 | 5e-22 |
| sp\|P27057\|GST1_LYCES  GAST1 PROTEIN PRECURSOR >gi\|100217\|pir\|\|S2 . . . | 78 | 1e-21 |
| pir\|\|S71371  gibberellin-regulated protein GASA5 - Arabidopsis t . . . | 73 | 3e-20 |
| gb\|AAC32128.1\|  (AF051227) GASA5-like protein [Picea mariana] | 73 | 4e-20 |
| gb\|AAF15937.1\|AC011765_33  (AC011765) GAST1-like protein [Arabid . . . | 73 | 4e-20 |
| gb\|AAC32170.1\|  (AF051753) GASA5-like protein [Picea mariana] >g . . . | 69 | 7e-19 |
| gb\|AAC20716.1\|  (AC004669) putative gibberellin-regulated protei . . . | 69 | 7e-19 |
| sp\|P47926\|RSI1_LYCES  RSI-1 PROTEIN PRECURSOR (TR132) >gi\|107659 . . . | 68 | 9e-19 |
| gb\|AAC61287.1\|  (AC005396) similar to gibberellin-regulated prot . . . | 57 | 2e-15 |
| sp\|P46688\|GAS2_ARATH  GIBBERELLIN-REGULATED PROTEIN 2 PRECURSOR . . . | 54 | 2e-14 |
| gb\|AAC27845.1\|  (AC004218) similar to gibberellin-regulated prot . . . | 51 | 1e-13 |
| sp\|P46687\|GAS3_ARATH  GIBBERELLIN-REGULATED PROTEIN 3 PRECURSOR . . . | 50 | 2e-13 |
| gb\|AAB62947.1\|  (AF007784) LTCOR11 [Lavatera thuringiaca] | 49 | 5e-13 |
| pir\|\|S60229  GAST1 protein homolog (clone GASA1) - Arabidopsis t . . . | 44 | 1e-11 |
| sp\|P46689\|GAS1_ARATH  GIBBERELLIN-REGULATED PROTEIN 1 PRECURSOR . . . | 44 | 1e-11 |
| emb\|CAB45241.1\|  (AJ005206) GEG protein [Gerbera hybrida] | 43 | 3e-11 |
| gb\|AAB97006.1\|  (AF039183) GAST-like gene product [Fragaria x an . . . | 41 | 2e-10 |
| gb\|AAC15460.1\|  (AF060569) cold-regulated LTCOR12 [Lavatera thur . . . | 40 | 2e-10 |
| gb\|AAD01518.1\|  (AF014396) Snakin-1 [Solanum tuberosum] | 37 | 2e-09 |
| gb\|AAD15495.1\|  (AC006439) similar to gibberellin-regulated prot . . . | 29 | 6e-07 |
| ref\|NP_037530.1\|\|  zinc finger protein 224 >gi\|6715532\|gb\|AAF041 . . . | 6 | 3.3 |
| emb\|CAA84663.1\|  (Z35600) cDNA EST yk222a6.3 comes from this gen . . . | 6 | 4.2 |
| gb\|AAC97073.1\|  (AF042838) MEK kinase 1 [Homo sapiens] | 5 | 6.6 |
| gb\|AAF53381.1\|  (AE003643) CG15288 gene product [Drosophila mela . . . | 5 | 8.3 |
| gb\|AAD31714.1\|AF135118_1  (AF135118) laminin alpha1,2 [Drosophil . . . | 5 | 8.3 |
| Significant alignments for pattern occurrence 1 at position 98 | | |

APPENDIX IV

Output of PHI-PSI-BLAST search versus NR database using KCP
Regular Expression 2.

First PHI-BLAST Round Output

BLASTP 2.0.9
Reference: Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs", Nucleic Acids Res. 25: 3389-3402.
Query = Zm-KCP1, p0118.chsbd73r, FL, *Zea mays*, proofed      (114 letters)
Database: nr     485,275 sequences; 152,116,570 total letters
Searching
1 occurrence(s) of pattern in query
    Pattern for KCP identification
    pattern [CS]-[PSQAG]-x(0,2)-C-Y-x(4)-[TNS]-x(5,8)-K
    at position 98 of query sequence
effective database length = 1.4e+08
    pattern probability = 1.0e−06length × probability = 1.5e+02
. . . . . . . . . . . . . . . . . . . . . . . . . . . . . . . . . . . . . . . .
Number of occurrences of pattern in the database is 291 done Results from round 1

| | Score (bits) | E Value |
|---|---|---|
| Significant matches for pattern occurrence 1 at position 98 | | |
| emb\|CAA66909.1\|   (X98255) transcriptionally stimulated by gibber . . . | 80 | 2e−22 |
| pir\|\|S60232   GAST1 protein homolog (clone GASA4) - *Arabidopsis t* . . . | 80 | 2e−22 |
| sp\|P46690\|GAS4__ARATH   GIBBERELLIN-REGULATED PROTEIN 4 PRECURSOR . . . | 80 | 2e−22 |
| pir\|\|S54832   gip1 protein-garden *petunia* >gi\|825524\|emb\|CAA606 . . . | 79 | 5e−22 |
| sp\|P27057\|GST1__LYCES   GAST1 PROTEIN PRECURSOR >gi\|100217\|pir\|\|S2 . . . | 78 | 1e−21 |
| pir\|\|S71371   gibberellin-regulated protein GASA5 - *Arabidopsis t* . . . | 73 | 3e−20 |
| gb\|AAC32128.1\|   (AF051227) GASA5-like protein [*Picea mariana*] | 73 | 4e−20 |
| gb\|AAF15937.1\|AC011765__33   (AC011765) GAST1-like protein [*Arabid* . . . | 73 | 4e−20 |
| gb\|AAC32170.1\|   (AF051753) GASA5-like protein [*Picea mariana*] >g . . . | 69 | 7e−19 |
| gb\|AAC20716.1\|   (AC004669) putative gibberellin-regulated protei . . . | 69 | 7e−19 |
| sp\|P47926\|RSI1__LYCES   RSI-1 PROTEIN PRECURSOR (TR132) >gi\|107659 . . . | 68 | 9e−19 |
| gb\|AAC61287.1\|   (AC005396) similar to gibberellin-regulated prot . . . | 57 | 2e−15 |
| sp\|P46688\|GAS2__ARATH   GIBBERELLIN-REGULATED PROTEIN 2 PRECURSOR . . . | 54 | 2e−14 |
| gb\|AAC27845.1\|   (AC004218) similar to gibberellin-regulated prot . . . | 51 | 1e−13 |
| sp\|P46687\|GAS3__ARATH   GIBBERELLIN-REGULATED PROTEIN 3 PRECURSOR . . . | 50 | 2e−13 |
| gb\|AAB62947.1\|   (AF007784) LTCOR11 [*Lavatera thuringiaca*] | 49 | 5e−13 |
| pir\|\|S60229   GAST1 protein homolog (clone GASA1) - *Arabidopsis t* . . . | 44 | 1e−11 |
| sp\|P46689\|GAS1__ARATH   GIBBERELLIN-REGULATED PROTEIN 1 PRECURSOR . . . | 44 | 1e−11 |
| emb\|CAB45241.1\|   (AJ005206) GEG protein [*Gerbera hybrida*] | 43 | 3e−11 |
| gb\|AAB97006.1\|   (AF039183) GAST-like gene product [*Fragaria* x an . . . | 41 | 2e−10 |
| gb\|AAC15460.1\|   (AF060569) cold-regulated LTCOR12 [*Lavatera thur* . . . | 40 | 2e−10 |
| gb\|AAD01518.1\|   (AF014396) Snakin-1 [*Solanum tuberosum*] | 37 | 2e−09 |
| gb\|AAD15495.1\|   (AC006439) similar to gibberellin-regulated prot . . . | 29 | 6e−07 |
| ref\|NP__037530.1\|\|   zinc finger protein 224 >gi\|6715532\|gb\|AAF041 . . . | 6 | 3.3 |
| emb\|CAA84663.1\|   (Z35600) cDNA EST yk222a6.3 comes from this gen . . . | 6 | 4.2 |
| gb\|AAC97073.1\|   (AF042838) MEK kinase 1 [*Homo sapiens*] | 5 | 6.6 |
| gb\|AAF53381.1\|   (AE003643) CG15288 gene product [*Drosophila mela* . . . | 5 | 8.3 |
| gb\|AAD31714.1\|AF135118__1   (AF135118) laminin alpha1, 2 [*Drosophil* . . . | 5 | 8.3 |

Significant alignments for pattern occurrence 1 at position 98

Second, PSI-Blast Round.

Searching . . . done
Results from round 2

| | Score (bits) | E Value |
|---|---|---|
| Sequences producing significant alignments: | | |
| Sequences used in model and found again: | | |
| pir\|\|S54832   gip1 protein - garden *petunia* >gi\|825524\|emb\|CAA606 . . . | 160 | 4e−39 |
| gb\|AAC61287.1\|   (AC005396) similar to gibberellin-regulated prot . . . | 148 | 2e−35 |
| sp\|P27057\|GST1__LYCES   GAST1 PROTEIN PRECURSOR >gi\|100217\|pir\|\|S2 . . . | 142 | 9e−34 |
| gb\|AAC32128.1\|   (AF051227) GASA5-like protein [*Picea mariana*] | 135 | 1e−31 |
| gb\|AAF15937.1\|AC011765__33   (AC011765) GAST1-like protein [*Arabid* . . . | 134 | 3e−31 |
| gb\|AAC20716.1\|   (AC004669) putative gibberellin-regulated protei . . . | 133 | 6e−31 |
| pir\|\|S71371   gibberellin-regulated protein GASA5 - *Arabidopsis t* . . . | 133 | 7e−31 |
| gb\|AAC32170.1\|   (AF051753) GASA5-like protein [*Picea mariana*] >g . . . | 130 | 6e−30 |
| sp\|P47926\|RSI1__LYCES   RSI-1 PROTEIN PRECURSOR (TR132) >gi\|107659 . . . | 128 | 2e−29 |
| pir\|\|S60232   GAST1 protein homolog (clone GASA4) - *Arabidopsis t* . . . | 124 | 4e−28 |
| emb\|CAA66909.1\|   (X98255) transcriptionally stimulated by gibber . . . | 123 | 5e−28 |
| sp\|P46690\|GAS4__ARATH   GIBBERELLIN-REGULATED PROTEIN 4 PRECURSOR . . . | 123 | 5e−28 |
| gb\|AAB62947.1\|   (AF007784) LTCOR11 [*Lavatera thuringiaca*] | 118 | 2e−26 |

APPENDIX IV-continued

| | | | |
|---|---|---|---|
| gb\|AAB97006.1\| | (AF039183) GAST-like gene product [*Fragaria* x an . . . | 117 | 4e−26 |
| sp\|P46687\|GAS3__ARATH | GIBBERELLIN-REGULATED PROTEIN 3 PRECURSOR . . . | 116 | 8e−26 |
| sp\|P46688\|GAS2__ARATH | GIBBERELLIN-REGULATED PROTEIN 2 PRECURSOR . . . | 116 | 8e−26 |
| sp\|P46689\|GAS1__ARATH | GIBBERELLIN-REGULATED PROTEIN 1 PRECURSOR . . . | 116 | 1e−25 |
| gb\|AAC15460.1\| | (AF060569) cold-regulated LTCOR12 [*Lavatera thur* . . . | 116 | 1e−25 |
| pir\|\|S60229 | GAST1 protein homolog (clone GASA1) - *Arabidopsis t* . . . | 116 | 1e−25 |
| emb\|CAB45241.1\| | (AJ005206) GEG protein [*Gerbera hybrida*] | 114 | 4e−25 |
| gb\|AAC27845.1\| | (AC004218) similar to gibberellin-regulated prot . . . | 112 | 1e−24 |
| gb\|AAD15495.1\| | (AC006439) similar to gibberellin-regulated prot . . . | 95 | 3e−19 |
| gb\|AAD01518.1\| | (AF014396) Snakin-1 [*Solanum tuberosum*] | 93 | 1e−18 |
| Sequences not found previously or not previously below threshold: | | | |
| gb\|AAC67545.1\| | (AF086604) mucin [*Homo sapiens*] | 42 | 0.003 |
| emb\|CAA06167.1\| | (AJ004862) mucin [*Homo sapiens*] | 39 | 0.018 |
| ref\|NP__002441.1\|\| | metallothionein 1L >gi\|462637\|sp\|P80297\|MT1L__ . . . | 37 | 0.052 |
| gb\|AAB71835.1\| | (AF008583) metallothionein [*Ambystoma mexicanum*] | 37 | 0.052 |
| gb\|AAD04919.1\| | (AF099154) von Willebrand factor [*Canis familiaris*] | 37 | 0.068 |
| sp\|Q28295\|VWF__CANFA | VON WILLEBRAND FACTOR PRECURSOR >gi\|1478046 . . . | 37 | 0.068 |
| prf\|\|1101271B | metallothionein MT Ipg [*Homo sapiens*] | 37 | 0.068 |
| gb\|AAB93766.1\| | (U66246) von Willebrand factor [*Canis familiaris*] | 37 | 0.068 |
| gb\|AAC06229.1\| | (AF052036) von Willebrand factor precursor [*Sus* . . . | 37 | 0.090 |
| ref\|NP__003881.1\|\| | IgG Fc binding protein >gi\|1944352\|dbj\|BAA195 . . . | 37 | 0.090 |
| emb\|CAA70525.1\| | (Y09353) von Willebrand factor [*Bos taurus*] | 37 | 0.090 |
| gb\|AAC39446.1\| | (AF060485) MEDEA [*Arabidopsis thaliana*] >gi\|4185 . . . | 37 | 0.090 |
| gb\|AAD39266.1\|AC007842__1 | (AC007842) Human Fc gamma BP [AA 1-284 . . . | 37 | 0.090 |
| sp\|P04732\|MT1E__HUMAN | METALLOTHIONEIN-IE (MT-1E) >gi\|625332\|pir\| . . . | 36 | 0.12 |
| pir\|\|S43534 | integrin beta3 - chicken >gi\|474039\|emb\|CAA51069.1\| . . . | 36 | 0.12 |
| sp\|P09579\|MT2__BOVIN | METALLOTHIONEIN-II (MT-II) >gi\|89654\|pir\|\|B . . . | 36 | 0.12 |
| ref\|NP__033746.1\|\| | a disintegrin and metalloproteinase domain 19 . . . | 36 | 0.15 |
| pir\|\|S38539 | gene MDC protein - human >gi\|455835\|gb\|AAB29191.1\| . . . | 36 | 0.15 |
| pir\|\|I52965 | disintegrin-like metalloproteinase (EC 3.4.24.—) - . . . | 36 | 0.15 |
| dbj\|BAA06670.1\| | (D31872) metalloprotease/disintegrin-like prote . . . | 36 | 0.15 |
| sp\|P14425\|MT2__STECO | METALLOTHIONEIN-II (MT-II) >gi\|225981\|prf\| . . . | 36 | 0.15 |
| pir\|\|S60258 | meltrin beta-mouse (fragment) >gi\|1584289\|prf\|\|21 . . . | 36 | 0.15 |
| ref\|NP__031426.1\|\| | a disintegrin and metalloproteinase domain 12 . . . | 36 | 0.15 |
| dbj\|BAA18923.1\| | (D50410) meltrin beta [*Mus musculus*] | 36 | 0.15 |
| emb\|CAA07188.1\| | (AJ006692) ultra high sulfer keratin [*Homo sapi* . . . | 36 | 0.15 |
| emb\|CAA09979.1\| | (AJ012287) alpha tectorin [*Gallus gallus*] | 36 | 0.15 |
| ref\|NP__033743.1\|\| | a disintegrin and metalloprotease domain (ADA . . . | 36 | 0.15 |
| ref\|NP__002381.2\|\| | metalloproteinase-like, disintegrin-like, cys . . . | 36 | 0.15 |
| sp\|P02801\|MT1B__HORSE | METALLOTHIONEIN-IB (MT-IB) | 36 | 0.15 |
| ref\|NP__005944.1\|\| | metallothionein 2A; MT-II >gi\|127397\|sp\|P0279 . . . | 35 | 0.20 |
| ref\|NP__038631.1\|\| | metallothionein 3 >gi\|127405\|sp\|P28184\|MT3__MO . . . | 35 | 0.20 |
| pir\|\|SMHO1A | metallothionein 1A - horse | 35 | 0.20 |
| sp\|P17816\|GRP__HORVU | GLYCINE-RICH CELL WALL STRUCTURAL PROTEIN P . . . | 35 | 0.20 |
| sp\|P42124\|EZ__DROME | ENHANCER OF ZESTE PROTEIN >gi\|404864\|gb\|AAC4 . . . | 35 | 0.20 |
| sp\|P02800\|MT1A__HORSE | METALLOTHIONEIN-IA (MT-1A) | 35 | 0.20 |
| dbj\|BAA19183.1\| | (AB000794) metallothionein isoform [*Sus scrofa*] | 35 | 0.20 |
| sp\|O19000\|MT1__CANFA | METALLOTHIONEIN-I (MT-I) >gi\|2564070\|dbj\|BA . . . | 35 | 0.20 |
| prf\|\|1201189A | metallothionein [*Canis familiaris*] | 35 | 0.20 |
| prf\|\|1101271A | metallothionein MT IIpg [*Homo sapiens*] | 35 | 0.20 |
| gb\|AAF50149.1\| | (AE003547) E(z) gene product [*Drosophila melanog* . . . | 35 | 0.20 |
| sp\|P04733\|MT1F__HUMAN | METALLOTHIONEIN-IF (MT-1F) >gi\|72161\|pir\| . . . | 35 | 0.26 |
| sp\|P80294\|MT1H__HUMAN | METALLOTHIONEIN-IH (MT-1H) (METALLOTHIONEI . . . | 35 | 0.26 |
| gb\|AAF44843.1\|AE003406__48 | (AE003416) symbol = BG: DS00180.10; cDNA . . . | 35 | 0.26 |
| sp\|P07438\|MT1B__HUMAN | METALLOTHIONEIN-IB (MT-1B) >gi\|625334\|pir\| . . . | 35 | 0.26 |
| pir\|\|I46414 | metallothionein-Ia - sheep | 35 | 0.26 |
| gb\|AAB51591.1\| | (U93207) metallothionein [*Liza aurata*] | 35 | 0.26 |
| ref\|NP__003465.1\|\| | Meltrin-alpha, mouse, homolog of >gi\|2677839\| . . . | 35 | 0.26 |
| gb\|AAC08703.1\| | (AF023477) meltrin-S [*Homo sapiens*] | 35 | 0.26 |
| sp\|P52727\|MTA__SPAAU | METALLOTHIONEIN A (MT A) >gi\|1289282\|emb\|CA . . . | 35 | 0.26 |
| emb\|CAB46832.1\| | (AJ388530) metallothionein isoform 2 [*Canis fam* . . . | 35 | 0.26 |
| gb\|AAF23355.1\|AF078844__1 | (AF078844) hqp0376 protein [*Homo sapiens*] | 35 | 0.26 |
| sp\|Q93083\|MT1R__HUMAN | METALLOTHIONEIN-IR (MT-1R) >gi\|1495464\|emb . . . | 35 | 0.26 |
| emb\|CAB63401.1\| | (Z98877) cDNA EST yk385a5.3 comes from this gen . . . | 35 | 0.26 |
| emb\|CAB04626.1\| | (Z81573) M02G9.3 [*Caenorhabditis elegans*] | 35 | 0.26 |
| gb\|AAF53364.1\| | (AE003642) BG: DS00180.10 gene product [*Drosophil* . . . | 35 | 0.26 |
| sp\|P80295\|MT1I__HUMAN | METALLOTHIONEIN-1I (MT-1I) | 35 | 0.26 |
| ref\|NP__033606.1\|\| | zona pellucida glycoprotein 1 >gi\|2137874\|pir . . . | 35 | 0.35 |
| sp\|Q92145\|MT__TREBE | METALLOTHIONEIN (MT) >gi\|1322388\|emb\|CAA9656 . . . | 35 | 0.35 |

Note:
other sequences were left off for sake of brevity that had even less significant scores.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a polynucleotide selected from the group consisting of:
   a. a polynucleotide that encodes the polypeptide of SEQ ID NO:57;
   b. a polynucleotide having at least 95% sequence identity to SEQ ID NO:21, wherein said polynucleotide encodes a polypeptide having antifungal or nematicidal activity, and wherein the final three amino acids of said polypeptide are lysine, cysteine and proline, respectively;
   c. a polynucleotide comprising the sequence set forth in SEQ ID NO:21; and
   d. a polynucleotide fully complementary to the polynucleotide of any one of (a) through (c).

2. A vector comprising at least one nucleic acid molecule of claim 1.

3. A recombinant expression cassette comprising a nucleic acid molecule having the polynucleotide sequence of the nucleic acid molecule of claim 1 operably linked to a promoter.

4. A host cell comprising the recombinant expression cassette of claim 3.

5. A transgenic plant cell comprising the recombinant expression cassette of claim 3.

6. A transgenic plant comprising the recombinant expression cassette of claim 3.

7. The transgenic plant of claim 6, wherein the plant is maize, soybean, sunflower, sorghum, canola, wheat, alfalfa, cotton, rice, barley, or millet.

8. A transgenic seed from the transgenic plant of claim 6.

* * * * *